United States Patent [19]
Kilburn et al.

[11] Patent Number: 5,874,308
[45] Date of Patent: Feb. 23, 1999

[54] COMPOSITIONS AND METHODS FOR MODULATING CELL PROLIFERATION USING GROWTH FACTOR-POLYSACCHARIDE BINDING FUSION PROTEINS

[75] Inventors: Douglas G. Kilburn; Keith R. Humphries; James G. Doheny; Eric Jervis; Judie Alimonti, all of Vancouver, Canada

[73] Assignee: University of British Columbia, Canada

[21] Appl. No.: 585,585

[22] Filed: Jan. 16, 1996

[51] Int. Cl.[6] .............................. C07K 14/00; C12N 5/02
[52] U.S. Cl. ...................... 435/395; 435/383; 435/384; 435/385; 435/386; 435/387; 530/350; 530/351; 530/387.1; 530/399; 514/2
[58] Field of Search .................................. 435/179, 200, 435/325, 395, 383, 386, 375, 387, 385, 384; 530/350, 387.1, 399, 351; 514/2

[56] References Cited

U.S. PATENT DOCUMENTS

| | | | |
|---|---|---|---|
| 5,137,819 | 8/1992 | Kilburn et al. | 435/179 |
| 5,202,247 | 4/1993 | Kilburn et al. | 435/195 |
| 5,340,731 | 8/1994 | Kilburn et al. | 435/179 |
| 5,474,687 | 12/1995 | Van Vlasselaer | 210/782 |

FOREIGN PATENT DOCUMENTS

| | | |
|---|---|---|
| WO 93/21331 | 10/1993 | WIPO . |
| WO 94/24158 | 10/1994 | WIPO . |
| 97/26358 A1 | 7/1997 | WIPO . |

OTHER PUBLICATIONS

Lappi et al. Expression and activities of a recombinant basic fibroblast growth factor–saporin fusion protein. The Journal of Biological Chemistry. vol. 269, No. 17, pp. 12552–12558, Apr. 29, 1994.

Miyagishima et al. Expression, purification and binding to the receptor of human insulin–like growth factor II. Biochimica et Biophysica Acta. vol. 1203, pp. 155–161, 1993.

Weber et al. Immunoaffinity purification of the epidermal growth factor receptor. The Journal of Biological Chemistry. vol. 259, No. 23, pp. 14631–14636, Dec. 10, 1984.

Weich et al. Interleukin–3/erythropoietin fusion proteins: in vitro effects on hematopoietic cells. Experimental Hematology. vol. 21, pp. 647–655, 1993.

Vadhan–Raj et al. In vivo biological effects of PIXY321, a synthetic hybrid protein of recombinant human granulocyte–macrophage colony–stimulating factor and interleukin–3 in cancer patients with normal hematopoiesis: a phase I study. Blood. vol. 86, No. 6, pp. 2098–2105, Sep. 15, 1995.

Ong et al. The cellulose–binding domains of cellulases: tools for biotechnology. Trends in Biotechnology. vol. 7, pp. 239–243, 1989.

Wierzba et al. Adhesion of mammalian cells to a recombinant attachment factor, CBD/RGD, analyzed by image analysis. Biotechnology and Bioengineering. vol. 46, No. 3, pp. 185–193, May 5, 1995.

Jervis et al *Cellulose Binding Domain Cytokine Fusion Proteins As A Means of Supplying Surface Localized Growth Factors to Cells* 211th American Chemical Society National Meeting, Abstract of Paper (1996) BIOT 222.

(List continued on next page.)

*Primary Examiner*—Elizabeth C. Kemmerer
*Attorney, Agent, or Firm*—Barbara Rae-Venter; Viola T. Kung; Rae-Venter Law Group, P.C.

[57] ABSTRACT

Methods and compositions are provided for in vitro expansion of growth factor dependent cells. Expansion is effected through the use of growth factor conjugates that include a growth factor such as a steel factor and a polysaccharidase substrate binding region. The conjugates are immobilized by binding of the substrate binding region to a substrate of the polysaccharidase in a growth chamber for the cells.

27 Claims, 31 Drawing Sheets

OTHER PUBLICATIONS

Long et al *Human hematopoietic stem cell adherence to cytokines and matrix molecules*, J. Clin. Invest. (1992) 90:251–255.

Ong et al *Purification of human interleukin–2 using the cellulose–binding domain of a prokaryotic cellulase* Bioseparation (1995) 5:95–104.

Tomme et al *Cellulose–binding Domains* Ann. N.Y. Acad. Sci. (1996) 799:418–424.

FIG. 1

A) Native SLF:

B) Cex:

C) SLF-CBD fusion protein:

(HHHHHHHIEGRARKEI)                    (PPVASIEGR)*

D) Recombinant SFL control:

18.6 kDa (non-glycosylated)

```
                                                                    NcoI  EcoRI                       MCS                                    HindIII
              g10 leader                                rbs          M  E  F  E  L  G  T  R  G  S  S  R  V  D  L  Q  A  C  K  L
  XbaI
AtctagaAATAATTTTGTTTAACTTTAAGAaggaGATATATccatggaattcGAGCTCGGTACCCGGGATCCTCTAGAGTCGACCTGCAGGCATGCaagctt
TagatctTTATTAAAACAAATTGAAATTCTcctCTATATAgtaccttaagCTCGAGCCATGGGCCCCTAGGAGATCTCAGCTGGACGTCCGTACGttcgaa
```

FIG. 3A

```
                                                       FXa    StuI    EcoRI                   mcs                                    HindIII
  g10       SacI   M  E  T  F  (CBDPT) I  E  G  R  P  E  F  Q  L  G  T  R  G  S  S  R  V  D  L  Q  A  C  K  L
   rbs
GAaggagctcCTTGATGTCCACCGC......ATCGAGGGCaggcctgaattcCAGCTCGGTACCCGGGATCCTCTAGAGTCGACCTGCAGGCATGCaagctt
CTtcctcgagGAACTACAGGTGGCG......TAGCTCCCGtccggacttaagGTCGAGCCATGGGCCCCTAGGAGATCACAGCTGGACGTCCGTACGttcgaa
```

FIG. 4A

COMPOSITIONS AND METHODS FOR MODULATING CELL PROLIFERATION USING GROWTH FACTOR-POLYSACCHARIDE BINDING FUSION PROTEINS

INTRODUCTION

1. Technical Field

This invention relates to compositions and methods for modulating cell proliferation using fusion proteins composed of a growth factor and a binding domain derived from a polysaccharidase. The invention is exemplified by the use of a fusion protein that includes hematopoietic growth factor steel factor (SLF) and a binding domain derived from a bacterial cellulase to stimulate proliferation of bone marrow cells in vitro.

2. Background

A major objective in bioprocess engineering is the development of cell culture methods which provide the environmental conditions necessary for maximum cell densities and specific cell derived product recovery. In vivo, growth factors for various target cells are often associated with the extracellular matrix (ECM). The major extracellular matrix components are proteoglycans of which there are four major forms: heparin sulfate, chondritin sulfate, keratan sulfate and hyaluronic acid. The binding properties of these ECM proteins are primarily determined by the form of the glycosaminoglycan carried on the proteoglycan. These molecules appear to protect the growth factors from proteolytic degradation and are thought to be an important reservoir of growth factors in the ECM. Proteoglycans are an abundant and ubiquitous tissue component and are likely to capture a majority of intercellular growth factors for which they have affinity. It has been suggested that the combined action of diffusable factors and nondiffusable matrix signals may be an important mechanism for localizing responses of cells to a cytokine that is widely distributed within an organism. Several cytokines, including basic fibroblast growth factor (bFGF), granulocyte-macrophage colony stimulating factor (GM-CSF), and interleukin-3 (IL-3), have been shown to function when bound to proteoglycans of the ECM.

Of particular interest for culturing in vitro are cells of the hematopoietic system. The culture and expansion of bone marrow cells in vitro has required the use of irradiated preformed stromal-cell feeder layers. Dexter et al. ((1993) Nature, 360:709–710) demonstrated that this technique maintained cell populations which were able to regenerate hematopoiesis in irradiated mice. Since these initial studies, various combinations of cytokines added to the culture medium have been reported to effectively replace the stromal layer for maintenance of human hematopoiesis in culture. As an example, Matrigel, a commercially available artificial ECM, has been used to immobilize IL-3 and GM-CSF for growing factor-dependent (IL-3 and GM-CSF) cell lines. Immobilized heparin sulfate can be used to replace the Matrigel. In addition, several factors or combinations of factors can substitute for one another to obtain similar target cell responses. As an example, Steel factor (SLF) or granulocyte colyny stimulating factor (G-CSF) plus IL-3 can be substituted for feeder layers in supporting LTC-IC maintenance, although relatively high concentrations of the factors are required. However, surface expression of IL-3 receptors is downregulated in response to high concentrations of soluble IL-3. Genetically engineered stromal cells transfected to produce G-CSF, GM-CSF and IL-3 alone or in combination have also been shown to enhance the maintenance of LTC-IC cultures significantly.

The in vitro expansion of T-cells for adoptive immunotherapy has achieved tumor regression in some patients with advanced cancer. With this technique, T-cells are removed from a cancer patient and expanded in culture. Once a sufficient number of cells have been produced, they are reintroduced into the patient. A major obstacle in the expansion of activated T-cells in vitro has been the complexity and the expense of processing cultures using conventional tissue culture procedures. Furthermore, when high concentrations of growth factors such as IL-2 are added to IL-2 dependent cells, receptors on the cell surface for IL-2 are down regulated as the IL-2 concentration increases. To counteract this problem, liposomes have been used to increase the IL-2 dependent proliferation of CTLL cells. Use of 20 nM lipids with recombinant human IL-2 greatly increased cell proliferation; proliferation was the most pronounced at low dosages of IL-2. At saturating dosages of IL-2, the liposomes had no significant effect. Additionally, lipid concentrations above 120 nM were found to inhibit proliferation. Thus, another hematopoietic cell for which efficient ex vivo expansion techniques are required is the T-lymphocyte. A dialysis perfusion bioreactor for the expansion of lymphokine-activated killer T-cells for adoptive immunotherapy also has been used. The doubling times, surface molecule phenotype and cytolytic activities were similar for cells produced in the perfusion bioreactor or in standard tissue-culture plates.

SLF, as well as a number of other growth factors, can act as attachment factors when adsorbed non-specifically to plastic, and have been reported to stimulate the proliferation of primitive progenitor cells (Long et al. (1992) J. Clin. Invest. 90:251–255). Such methods of immobilization, however, do not ensure that the growth factor is presented in the correct orientation. A polar affinity tag might facilitate attachment in the correct orientation but most of the commonly used affinity tags, such as hexahistidine (Smith et al. (1988) J. Biol. Chem. 263:7211–7215), streptavidin (Kasher et al. (1986) Mol. Cell. Biol. 6:3117–3127), or GST (Smith and Johnson (1988) Gene 67:31–40) rely on matrices which could interfere with the in vitro culture conditions. Therefore, it is of interest to develop a system for the in vitro cultivation of cells for therapeutic reinfusion to the body which can provide for continuous expansion of stem cells and other factor dependent cell populations. Of particular interest is the development of a system which uses a single recoverable growth factor so as to avoid the necessity of preparing customized growth factor cocktails for each cell type of interest and to decrease the cost of using the systems.

Relevant Literature

Artificial matrices, such as surface hydrolyzed poly (methyl methacrylate) films (Ito et al. (1992) Biomaterials 13:789–794), or glass beads (Ito et al. (1992) Biotechnology and Bioengineering 40:1271–1276) with adsorbed or covalently attached growth factors have been used to replace extracellular matrices (ECMs) for growing cells in vitro. Immobilized insulin (Liu et al. (1992) Biomaterials 13:50–58), transferrin (Liu et al. (1993) International J. Biological Macromolecules 12:449–453), and insulin, transferrin, and collagen (Ito et al. (1991) Biomaterials 12:449–453) have been used with varying degrees of success.

Compositions and methods relating to cellulose and 1,4-, β-glycan binding domains are described in the following US patents: U.S. Pat. No. 5,340,731; U.S. Pat. No. 5,202,247; and U.S. Pat. No. 5,137,819. Also see PCT application WO 94/24158, which describes cellulose binding domain proteins ("scaffolding proteins").

SUMMARY OF THE INVENTION

The present invention provides methods and compositions for isolating and/or stimulating or inhibiting proliferation of growth-factor dependent cells through use of immobilized growth factors. The compositions include a cell surface ligand binding protein and a growth factor conjugate comprising a substrate binding region derived from a polysaccharidase and a ligand that binds to the binding protein. The substrate binding region preferably is essentially lacking in hydrolytic activity of the polysaccharidase. Methods of in vitro expansion of growth factor dependent cells also are provided. The methods involve growing cells with a cell surface receptor for the growth factor in contact with the growth factor conjugate. To obtain a population of cells enriched in growth factor dependent cells, a plurality of cells are contacted with the growth factor conjugate and any cells lacking the cell surface receptor are then removed. Optionally, the cells can be removed from the conjugate or the substrate. The growth factor conjugates also can be used for enhancing healing of a wound by contacting the wound with a growth factor conjugate that is optionally bound to a wound covering.

BRIEF DESCRIPTION OF THE DRAWINGS

FIG. 1 shows a consensus sequence for the cellulose binding domain. Amino acid sequence alignments of the cellulose-binding domains (CBDs) of *C. fimi* cellulases (CenA SEQ ID NO:1 and Cex SEQ ID NO:2), and the putative binding domains of MbCelA, SEQ ID NO:3 (an endoglucanase from *Microbiospora bispora*), ClfX SEQ ID NO:4 (part of the translated open reading frame of *Cellulomonas flavigena* gene fragment), Pfeg1 SEQ ID NO:5 (an endoglucanase from *Pseudomonas fluorescens* var. cellulosa PfxynA, SEQ ID NO:6 ) and Bfegll SEQ ID NO:7 (an endoglucanase from *Butyivibria fibrisolvens*). Amino acid residues are indicated in single letter code . Bold upper case letters indicate homology with the CenA sequence; plain upper case letters indicate homologies occurring only within the other six sequences; lower case letters indicate the absence of homology. * indicates the amino terminus of the mature enzyme. *** indicates a carboxyl terminus deduced from occurrence of stop codons in corresponding DNA sequences.—indicates a gap left to improve the alignment. Numbers refer to residues at the start and end of respective lines: CenA, Cex, and PfxynA residues are numbered from the start of the unprocessed polypeptides since the sites of leader peptide processing have not been determined; ClfX is numbered from the start of the *C. flavigena* gene fragment open reading frame.

FIG. 3(A–B) shows a graphic representation of the pTugA expression vector from which the expression vector used for high level expression of SLF-CBD fusion proteins in *Escherichia coli* was derived. Use of pTugA results in high level inducible transcription, enhanced RNA translation, portability, high copy number, stability and versatility. The pTug vectors contain the mutant pMB1 ori derived from pUC13 to enhance copy number (Minton et al. *Focus* (1988) 10:56), a strong and highly inducible (by IPTG) tac promoter ($P_{tac}$) which is strongly repressed by Laclq The laclq allele is incorporated in the pTug vector to maintain a constant ratio of $P_{tac}$ to laclq, ensuring adequate levels of repressor irrespective of the *E. coli* host. The gene10 translational enhancer (Olins et al. *Gene* (1988) 73:227) is also incorporated in the pTug vector. The leader sequence of the endoglucanase A (CenA) from *C. fimi* was incorporated in the vector to allow recovery of a recombinant polypeptide from *E. coli* supernatants. FIG. 3A shows the nucleotide and (SEQ ID NO:8) encoded amino acid sequence (SEQ ID NO:9) of the NcoI-HindIII region as well as the nucleotide sequence of the region upstream of the NcoI site, including the gene 10 translational enhancer ("g10") and the CenA leader sequence ("leader").

FIG. 4(A–B) shows a graphic representation of the pTugAS. FIG. 4A shows the nucleotide (SEQ ID NO:10,11) and encoded amino acid sequence (SEQ ID NO:12) of the SacI-HindIII region as well as the nucleotide sequence of the region upstream of the SacI site.

FIG. 8A shows purification of SLF-CBD with cellulose: lane 1, markers; lane 2, conditioned growth medium; lane 3, fusion protein recovered from 5 ml of conditioned growth medium by absorption to 5 mg of Avicel; lane 4, periplasmic extract; lane 5, fusion protein extracted directly from 1 ml of periplasmic extract by 5 mg of Avicel. FIG. 8B shows purification of SLF-CBD with nickel Sepharose using the hexahistidine tag: lane 1, markers; lane 2, fusion protein elution peak.

FIG. 9A shows SDS-PAGE of SLF-CBD: (Coomassie blue stained) lane 1, markers; lane 2, prestained markers; lane 3, 1 µg purified SLF-CBD; lane 4, 20ng SLF-CBD cut by Factor Xa (not visible on gel); lane 5, 10 ng recombinant control SLF (not visible on gel, dark band is BSA); lane 6, 500 ng $CBD_{cex}$; lane 7, vector only cell extract (negative control). FIG. 9B shows a western blot with anti-SLF polyclonal antibodies (lane designations were the same as for FIG. 9A). FIG. 9C shows a western blot with anti-CBD polyclonal antibodies (lane designations are the same as for FIG. 9A).

FIG. 12 shows SLF-CBD with and without either 1 µg/m 1 BMCC or 14 µg/m 1 BMCC.

FIG. 17A compares binding the presence (+) and absence (–) of barley β-glucan; FIG. 17B compares binding in the presence (+) and absence (–) of hydroxyethyl cellulose, and FIG. 17C compares binding in the presence (+) and absence (–) of birchwood xylan.

FIG. 20A shows pTZ-JC2 containing the gene fragment encoding the whole CenC, which was used to obtain the fragment encoding $PBD_{N1}$. FIG. 20B shows vector pUC18–1.6 cenAΔPT, which was used to obtain the CenA encoding fragment.

FIG. 22A shows the results of incubating aliquots of buffer containing 25 μg (lanes 2 and 3), 100 μg (lanes 4 and 5), or 250 μg (lanes 6 and 7) of both polypeptides with bacterial microcrystalline cellulose (BMCC)(+) or without BMCC(−). FIG. 22B shows the results of incubating supernatants containing the unadsorbed fractions from the BMCC incubation mixtures with phosphoric acid swollen cellulose (PASC)(+)). Results with control samples without addition of (PASC(−)) are also shown.

DESCRIPTION OF THE SPECIFIC EMBODIMENTS

Figure 2:
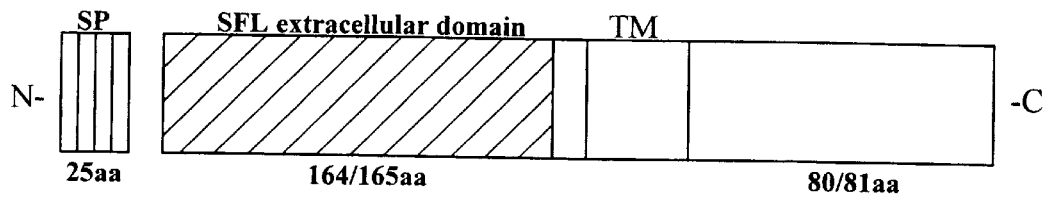
FIG. 2(A–D) shows SLF-CBD fusion protein and controls. The extracellular domain of murine steel factor (FIG. 2A) was used to replace the catalytic domain of the exoglucanase Cex (FIG. 2B) to create the fusion protein SLF-CBD (FIG. 2C). The recombinant extra cellular domain of murine steel factor was used as a positive control (FIG. 2D) and $CBD_{cex}$ was used as a negative control (not illustrated). * Details of fusion junctions. Underlined amino acids are the native SLF sequence.
Figure 2:
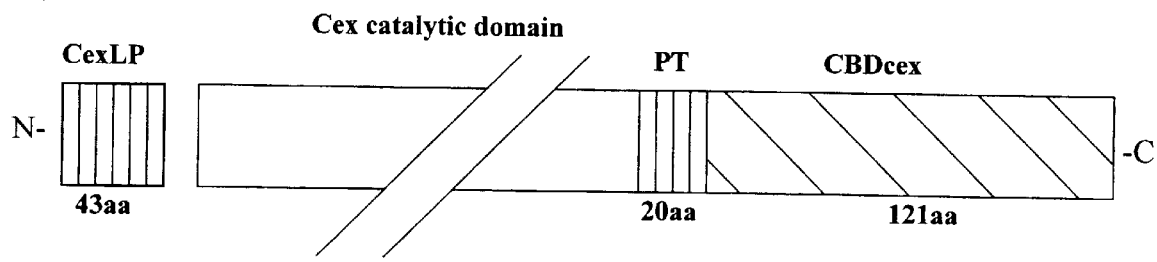
Figure 2:
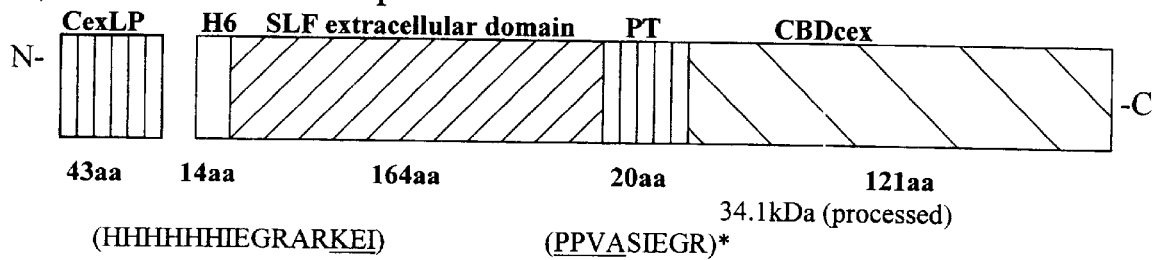
Figure 2:
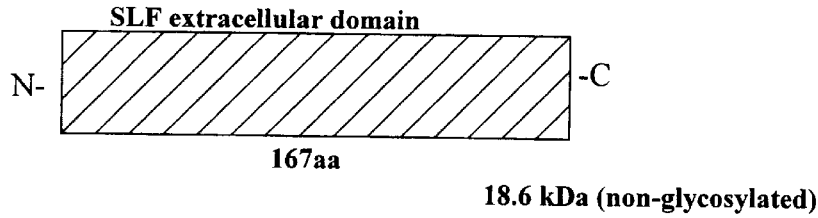

The present invention provides methods and compositions for ex vivo cultivation of growth-factor dependent cells, particularly cells of the hematopoictic system such as stem cells and T-lymphocytes. The compositions also find use for isolating growth-factor receptors and/or the cells containing them, and for promoting healing of a wound. The compositions include chimeric molecules comprising a growth factor and an amino acid sequence that is capable of binding to a polysaccharide substrate. By a growth factor is intended a factor, generally a polypeptide, which is capable of stimulating or otherwise modulating proliferation or differentiation of a target cell of interest having a cell surface receptor to which the growth factor binds. A target cell of interest is any cell which will proliferate and/or differentiate in response to stimulation by the growth factor. The amino acid sequence generally binds with high affinity to an oligosaccharide polymer, such as a β-glycan, in particular β-1,4-glycans, including cellulose and chitin. In use, the chimeric molecule is immobilized on the polysaccharide substrate, which can be either soluble or insoluble, and cells dependent upon the growth factor are grown in contact with the chimeric molecule. The methods are useful for in vitro cultivation of growth factor dependent cells including hematopoietic cells such as stem cells and megakaryocytes, other bone marrow and blood cells, nerve cells, and T cells.

The use of immobilized growth factors provides several advantages over non-immobilized growth factors and currently used methods for immobilizing growth factors and other biological molecules that modulate cell growth, differentiation, and proliferation. For example, immobilized growth factors can provide a continuous localized stimulus for cell proliferation. Unlike non-immobilized growth factors, which are often internalized and consumed by cells, immobilized growth factors remain bound to a substrate that is not consumed by cells and thus remain available to stimulate growth of additional cells. This is particularly useful in perfusion cultures in which growth medium is continuously added and removed to allow long term cell proliferation. Moreover, an immobilized growth factor is often more active than a soluble version of the growth factor.

Additional advantages provided by the subject invention include the following. Oligosaccharide polymers including carbohydrate polymers such as cellulose and other β-glucans, such as those obtained from oat and barley, are plentiful and inexpensive. Furthermore, a variety of proteins bind specifically to carbohydrate polymers and other oligosaccharides and can be used as the source of polysaccharide binding peptides (PBPs) for the subject invention. As an example, fusion proteins can be prepared which include the carbohydrate polymer-binding portion of a protein which binds to a carbohydrate as a means for immobilizing the fusion protein. Thus, use of the PBP provides a generic means for immobilization of any growth factor or related moiety by attaching it to a PBP which can bind to a polysaccharide. The selective binding of the PBP to the oligosaccharnrde polymer makes it especially suitable for the purification and/or immobilization of a wide variety of compounds.

The invention also provides methods for obtaining a population of cells enriched in growth factor dependent cells. These methods are useful for obtaining purified preparations of, for example, stem cells (including pluripotent stem cells) and other relatively rare cell types. The methods involve contacting a plurality of cells with a growth factor conjugate and then removing any cells that lack the cell surface receptor. The cells having receptors for the growth factor of interest bind specifically to the growth factor conjugates, while other non-growth factor dependent cells do not bind to the growth factor conjugates in significant amounts. The bound cells can be used while still bound to the growth factor conjugates; alternatively, the cells can be eluted from the growth factor conjugates to obtain a purified preparation of growth factor dependent cells. In some instances, enrichment also can be accomplished by the specific growth stimulation provided by the growth factor conjugate which will preferentially increase proliferation of responsive cells.

The growth factor conjugates described herein also can be used for enhancing healing of a wound. This is accomplished by contacting the wound with the growth factor conjugate that, in this instance, comprises an agent that either stimulates proliferation of cells involved in wound healing, and/or is chemotactic for such cells. The growth factor conjugate is optionally bound to a wound covering, preferably a covering that comprises a polysaccharide matrix, particularly a cellulose matrix, such as a sponge or a cotton bandage.

The invention provides novel polypeptide compositions that can include those having the following formula:

PBP-MR-X          (1)

wherein:

PBP is characterized as a consecutive sequence of amino acids from the substrate binding region of a polysaccharidase or other protein which binds to a polysaccharide substrate to provide for high affinity binding to a substrate of the polysaccharidase. The PBP, which is optionally essentially lacking in polysaccharidase activity, is at least as large as the minimum number of amino acids in a sequence required to bind a polysaccharide;

MR is the middle region, and can be a bond; a short linking group of from 2 to 30 carbon atoms, or have from about 2 to about 20 amino acids. The region can include an amino acid sequence providing for specific cleavage of the fusion protein that comprises the growth factor conjugate, usually a sequence corresponding to that recognized by a proteolytic enzyme of high specificity such as an IgA1 protease or Factor Xa; and X can be any growth factor or other moiety that stimulates or inhibits cell proliferation or activation through binding to a cell surface receptor. X is characterized as having up to the entire sequence of a polypeptide of interest; X can have only that part of the polypeptide that is required to exert the desired effect on cell proliferation. X can be, for example, a cytokine, lymphokine, or other growth factor. For example, suitable growth factors include a steel factor, an interleukin-2, an interleukin-3, an interleukin-6, an interleukin- 11, a mast cell growth factor, a granulocyte colony stimulating factor, a granulocyte-macrophage colony stimulating factor, a fibroblast growth factor, a platelet-derived growth factor, or an epidermal growth factor. X indicates only the moiety, not the stoichiometry of the moiety, which can be variable.

PBP-MR-X can be bound to an isolated receptor R for X, or to cells containing R, wherein the composition has the formula:

PBP-MR-X:R     (2)

wherein R can be any moiety that is present on a cell surface and which, when contacted bN a corresponding ligand (X), specifically binds R. R and X are the first and second members, respectively, of a specific binding pair. Generally, the interaction between X and R is noncovalent, such as electrostatic, hydrogen bonding, polar/nonpolar interactions, and the like. R can be, for example, a growth factor receptor, a T cell receptor, an immunoglobulin, or a MHC polypeptide. Specific binding of the first member to the second member of a specific binding pair generally is of high affinity, namely on the order of $10^{-8}$ to $10^{-11}$M when R is a growth factor receptor.

A characteristic of the specific binding pairs used in the subject invention is that the interaction of the second member with the first member exerts an effect either directly or indirectly on the cell upon which the first member is present. For example, interaction of a binding pair wherein the second member is a growth factor and its corresponding receptor is the first member can induce a cell to proliferate. Examples of such proliferation-inducing growth factors are steel factor, epidermal growth factor, nerve growth factor, brain derived neurotrophic factor, erythropoietin, GM-CSF, interleukins (including IL-2 and IL-3 and others), and the like. Interaction between the members of other specific binding pairs can cause activation or inactivation of a cell, or can induce a cell to differentiate. For example, an appropriate MHC polypeptide can interact with a T cell receptor to induce clonal anergy of a T cell population. Other binding pairs can serve as chemotactic signals that direct cell migration. Several growth factors have been shown to be chemotactic for their respective target cell, including platelet derived growth factor (PDGF) for neutrophylls and fibroblasts, IL-2 for T-lymphocytes (particularly activated CD4$^+$ T-lymphocytes), insulin for T-cells (both CD4$^+$, and CD8$^+$) as well as unactivated T-cells. This characteristic has been exploited in wound healing. Other examples of chemotactic moieties include cell adhesion receptors such as integrins, LAM-1, ICAM-1, LFA-3, H-CAM, ELAM-1, and their corresponding receptors or ligands.

Either or both members of a specific binding pair can comprise a polypeptide and/or a carbohydrate. Carbohydrates that are useful in the subject invention include those, such as sialyl-Lewis$^x$ (SLe$^x$) and other carbohydrate moieties involved in cell adhesion and signaling, that specifically bind ligands. For example, a conjugate that comprises a ligand for Sle$^x$ (such as ELAM-1) linked to a polysaccharidase substrate binding region is useful for purifying cells that display SLe$^x$ on their surfaces, and also for purifying SLe$^x$-containing oligosaccharides and proteins to which such oligosaccharides are linked. Alternatively, a carbohydrate ligand such as SLe$^x$ can be linked to a polysaccharidase substrate binding region (PBP); such conjugates are useful for attracting cells that display on their surfaces a ligand that binds SLe$^x$. Immobilizing these conjugates on a polysaccharide support such as a wound covering thus provides a method of directing cells involved in, for example, fighting infection, to the wound.

Growth factor conjugates need not include an entire naturally-occurring growth factor or other cell modulating agent. It is sufficient that the conjugate include a portion of the molecule that retains the desired biological activity. In the case of a polypeptide growth factor, for example, it is often advantageous to construct a growth factor conjugate that does not include a transmembrane domain that is present in the native, naturally occurring growth factor. The identification of such transmembrane domains is well known to those of skill in the art, as are methods for obtaining truncated growth factor molecules that lack the transmembrane or other undesired region. In the case of steel factor, for example, the 189 amino acid extracellular domain is of particular interest for stimulating cell proliferation. A steel factor conjugate can thus be constructed by deleting from the steel factor gene the portions that encode the 25 amino acid signal peptide, the 23 amino acid hydrophobic membrane anchor, and the 36 amino acid cytoplasmic domain (Huang et al. (1990) *Cell* 63: 225–233; Flanagan et al. (1990) *Cell* 63: 185–194; and Martin et al. (1990) *Cell* 63: 203–211).

For some applications, a conjugate that is bifunctional is used. The bifunctional conjugate includes more than one growth factor attached to the PBP, usually two growth factors. These conjugates include a second second member of a binding pair in addition to the first second memnber of a specific binding pair. The second second member generally is a different growth factor from the first second member. Both the first and second second members are attached to the PBP. An example of such a bifunctional growth factor conjugate is a PBP to which is bound steel factor and one or more growth factors, preferably a growth factor with which steel factor acts synergistically, such as IL-3, IL-11, GM-CSF, and/or EPO.

The PBPs include amino acid sequences that are derived from a substrate binding region (SBD; also referred to herein as a polysaccharide binding domain (PBD)) of a polysaccharidase. The polysaccharide binding peptide can include any amino acid sequence which binds to an oligosaccharide polymer, for example, the PBP can be derived from a SBD of a polysaccharidase, a binding domain of a polysaccharide binding protein or a protein designed and engineered to be capable of binding to a polysaccharide. The PBP can be naturally occurring or synthetic. Suitable polysaccharidases from which a PBP or SBD may be obtained include β-1,4-glucanases. In a preferred embodiment, a PBP or SBD from a cellulase is used. Typicallv, the amino acid sequence is essentially lacking in the hydrolytic activity of the polysaccharidase, but retains the substrate binding activity.

The amino acid sequence preferably has less than about 10% of the hydrolytic activity of the native polysaccharidase; more preferably less than about 5%, and most preferably less than about 1% of the hydrolytic activity of the native polysaccharidase.

The PBP can be obtained from a variety of sources, including enzymes which bind to ofigosaccharides which find use in the subject invention. In Table 5 below are listed those binding domains which bind to one or more soluble/insoluble polysaccharides including all binding domains with affinity for soluble glucans (α, β, and/or mixed linkages). The N1 cellulose-binding domain from endoglucanase CenC of *C. fimi* is the only protein known to bind soluble cellosaccharides and one of a small set of proteins which are known to bind any soluble polysaccharides. Also, listed in Tables 1 to 4 are examples of proteins containing putative β-1,3-glucan-binding domains (Table 1); proteins containing Streptococcal glucan-binding repeats (Cpl superfamily) (Table 2); enzymes with chitin-binding domains (Table 3), and starch-binding domains (Table 4). Scaffolding proteins which include a cellulose binding domain protein such as that produced by *Clostridium cellulovorans* (Shoseyov et al., PCT/US94/04132) can also be used for preparing a PBP. Several fungi, including Trichodenma species and others, also produce polysaccharidases from which PBP can be isolated.

TABLE 1

Overview of proteins containing putative β-1,3 glucan-binding domains

| Source (strain) | Protein | Accession No. | Ref[1] |
|---|---|---|---|
| Type I | | | |
| B. circulans (WL-12) | GLCA1 | P23903/M34503/JQ0420 | 1 |
| B. circulans (IAM 1165) | BglH | JN0772/D17519/S67033 | 2 |
| Type II | | | |
| Actinomadura sp. (FC7) | XynII | U08894 | 3 |
| Arthrobacter sp. (YCWD3) | GLCI | D23668 | 9 |
| O. xanthineolytica | GLC | P22222/M60826/A39094 | 4 |
| R. faecitabidus (YLM-50) | RPI | Q05308/A45053/D10753 | 5a,b |
| R. communis | Ricin | A12892 | 6 |
| S. lividans (1326) | XlnA | P26514/M64551/ JS07986 | 7 |
| T. tridentatus | FactorGa | D16622 | 8 |

B.: Bacillus, O. : Oerskovia, R. faecitabidus : Rarobacter faecitabidus, R. communis: Ricinus communis, S.: Streptomyces, T.: Tachypleus (Horseshoe Crab)

[1]References
1) Yahata et al. (1990) Gene 86, 113–117
2) Yamamoto et al. (1993) Biosci. Biotechnol. Biochem. 57, 1518–1525
3) Harpin et al. (1994) EMBL Data Library
4) Sken et al. (1991) J. Biol. Chem. 266, 1058–1063
5a) Shimoi et al. (1992) J. Biol. Chem. 267, 25189–25195
5b) Shimoi et al. (1992) J. Biochem 110, 608–613
6) Horn et al. (1989) Patent A12892
7) Shareck et al. (1991) Gene 107, 75–82
8) Seki et al. (1994) J. Biol. Chem. 269, 1370–1374
9) Watanabe et al. (1993) EMBL Data Library

TABLE 2

Overview of proteins containing Streptococcal glucan-binding repeats (Cpl superfamily)

| Source | Protein | Accession No. | Ref.[2] |
|---|---|---|---|
| S. downei (sobrinus) (0MZ176) | GTF-I | D13858 | 1 |
| S. downei (sobrinus) (MFe28) | GTF-I | P11001/M17391 | 2 |
| S. downei (sobrinus) (MFe28) | GTF-S | P29336/M30943/A41483 | 3 |
| S. downei (sobrinus) (6715) | GTF-I | P27470/D90216/A38175 | 4 |
| S. downei (sobrinus) | DEI | L34406 | 5 |
| S. mutants (Ingbritt) | GBP | M30945/A37184 | 6 |
| S. mutants (GS-5) | GTF-B | A33128 | 7 |
| S. mutants (GS-5) | GTF-B | P08987/M17361/B33135 | 8 |
| S. mutants | GTF-B[3'-ORF] | P05427/C33135 | 8 |
| S. mutants (GS-5) | GTF-C | P13470/M17361/M22054 | 9 |
| S. mutants (GS-5) | GTF-C | not available | 10 |
| S. mutants (GS-5) | GTF-D | M29296/A45866 | 11 |
| S. salivarius | GTF-J | A44811/S22726/S28809 Z11873/M64111 | 12 |
| S. salivarius | GTF-K | S22737/S22727/Z11872 | 13 |
| S. salivarius (ATCC 25975) | GTF-L | L35495 | 14 |
| S. salivarius (ATCC 25975) | GTF-M | L35928 | 14 |
| S. pneumoniae R6 | LytA | P06653/A25634/M13812 | 15 |
| S. pneumoniae | PspA | A41971/M74122 | 16 |
| Phage HB-3 | HBL | P32762/M34652 | 17 |
| Phage Cp-1 | CPL-1 | P15057/J03586/A31086 | 18 |
| Phage Cp-9 | CPL-9 | P19386/M34780/JQ0438 | 19 |
| Phage EJ-1 | EJL | A42936 | 20 |
| C. difficile (VPI 10463) | ToxA | P16154/A37052/M30307 X51797/S08638 | 21 |
| C. difficile (BARTS W1) | ToxA | A60991/X17194 | 22 |
| C. difficile (VPI 10463) | ToxB | P18177/X53138/X60984 S10317 | 23,24 |
| C. difficile (1470) | ToxB | S44271/Z23277 | 25,26 |
| C. novyi | a-toxin | S44272/Z23280 | 27 |
| C. novyi | a-toxin | Z48636 | 28 |
| C. acetobutylicum (NCIB38052) | CspA | S49255/Z37723 | 29 |
| C. acetobutylicum (NCIB38052) | CspB | Z50008 | 30 |
| C. acetobutylicum (NCIB8052) | CspC | Z50033 | 30 |
| C. acetobutylicum (NCIB8052) | CspD | Z50009 | 30 |

[2]References
1) Sato et al. (1993) DNA sequence 4, 19–27
2) Ferreti et al. (1987) J. Bacteriol 169, 4271–4278
3) Gilmore et al. (1990) J. Infect. Immun. 58, 2452–2458
4) Abo et al. (1991) J. Bacteriol. 173, 989–996
5) Sun et al. (1994) J. Bacteriol 176, 7213–7222
6) Banas et al. (1990) J. Infect. Immun. 58, 667–673
7) Shiroza et al. (1990) Protein Sequence Database
8) Shiroza et al. (1987) J. Bacteriol. 169, 4263–4270
9) Ueda et al. (1988) Gene 69, 101–109
10) Russel (1990) Arch. Oral. Biol. 35, 53–58
11) Honda et al. (1990) J. Gen. Microbiol. 136, 2099–2105
12) Giffard et al. (1991) J. Gen. Microbiol. 137, 2577–2593
13) Jacques (1992) EMBL Data Library
14) Simpson et al. (1995) J. Infect. Immun. 63, 609–621
15) Gargia et al. (1986) Gene 43, 265–272
16) Yother et al (1992) J. Bacteriol. 174, 601–609
17) Romero et al. (1990) J. Bacteriol. 172, 5064–5070
18) Garcia et al. (1988) Proc. Natl. Acad. Sci, USA 85, 914–918
19) Garcia et al. (1990) Gene 86, 81–88
20) Diaz et al (1992) J. Bacteriol. 174, 5516–5525
21) Dove et al. (1990) J. Infect. Immun. 58, 480–488
22) Wren et al. (1990) FEMS Microbiol. Lett 70, 1–6
23) Barroso et al. (1990) Nucleic Acids Res. 18, 4004–4004
24) von Eichel-Streiber et al. (1992) Mol. Gen. Genet. 233, 260–268
25) Sartinger et al. (1993) EMBL Data Library
26) von Eichel-Streiber et al. (1995) Mol. Microbiol. In Press
27) Hofmann et al. (1993) EMBL Data Library
28) Hofmann et al. (1995) Mol. Gen. Genet. 247: 670–679
29) Sanchez et al. (1994) EMBL Data Library
30) Sanchez et al. (1995) EMBL Data Library New PBPs with interesting binding characteristics and specificities can be identified and screened for in a variety of ways including spectroscopic (titration) methods such as: NMR spectroscopy (Zhu et al. (1995) *Biochemistry* 34:, Gehring et al. (1991) *Biochemistry* 30:5524–5531), UV difference spectroscopy (Beishaw et al. (1993)*Eur. J. Biochem.* 211:717–724), fluorescence (titration) spectroscopy (Miller et al. (1983) *J. Biol. Chem.* 258:13665–13672), UV or fluorescence stopped flow analysis (De Boeck et al. (1985) *Eur. J. Biochem.* 149:141–415), affinity methods such as affinity electrophoresis (Mimura et al. (1992) *J. Chronmatography* 597:345–350) or affinity chromatography on immobilized mono or oligosaccharides, precipitation or agglutination analysis including turbidimetric or nephelometric analysis (Knibbs et al. (1993) *J. Biol. Chem.* 14940–14947), competitive inhibition assays (with or without quantitative IC50 determination) and various physical or physico-chemical methods including differential scanning or isothermal titration calorimetry (Sigurskjold et al. (1992) *J. Biol. Chem.* 267:8371–8376; Sigurskjold et al. (1994) *Eur. J. Biol.* 225:133–141) or comparative protein stability assays (melts) in the absence or presence of oligosaccharides using thermal CD or fluorescence spectroscopy.

Generally, for use in constructing immobilized growth factors, the $K_a$ for binding of the PBP to oligosaccharide is at least in the range of weak antibody-antigen extractions, i.e., $\geq 10^3$, preferably $10^4$, most preferably $10^6 M^{-1}$. If the binding of the PBP to the oligosaccharide is exothermic or endothermic, then binding increases or decreases, respectively, at lower temperatures, providing a means for temperature modulation of the immobilization step.

TABLE 3

Overview of Enzymes with Chitin-binding Domains

| Source (strain) | Enzyme[a] | Accession No. | Ref.[3] |
|---|---|---|---|
| Bacterial enzymes | | | |
| Type I | | | |
| Aeromonas sp. (No10S-24) | Chi | D31818 | 1 |
| *Bacillus circulans* (WL-12) | ChiA1 | P20533/M57601/A38368 | 2 |
| *Bacillus circulans* (WL-12) | ChiD | P27050/D10594 | 3 |
| *Janthinobacterium lividum* | Chi69 | U07025 | 4 |
| *Streptomyces griseus* | ProteaseC | A53669 | 5 |
| Type II | | | |
| *Aeromonas cavia* (K1) | Chi | U09139 | 6 |
| *Alteromonas sp* (0–7) | Chi85 | A40633/P32823/D13762 | 7 |
| *Autographa californica* (C6) | NPH-128 | P41684/L22858 | 8 |
| *Serratia marcescens* | ChiA | A25090/X03657/L01455/P07254 | 9 |
| Type III | | | |
| *Rhizopus oligosporus* (IFO8631) | Chi1 | P29026/A47022/D10157/S27418 | 10 |
| *Rhizopus oligosporus* (IFO8631) | Chi2 | P29027/B47022/D10158/S27419 | 10 |
| *Saccharomyces cerevisiae* | Chi | S50371/U17243 | 11 |
| *Saccharomyces cerevisiae* (DBY939) | Chi1 | P29028/M74069 | 12 |
| *Saccharomyces cerevisiae* (DBY918) | Chi2 | P29029/M7407/B41035 | 12 |
| Plant enzymes | | | |
| Hevein superfamily | | | |
| *Allium sativum* | Chi | M94105 | 13 |
| *Amaranthus caudatus* | AMP-1[b] | P27275/A40240 | 14,15 |
| *Amaranthus caudatus* | AMP-2[b] | S37381/A40240 | 14,15 |
| *Arabidopsis thaliana* (CV. colombia) | ChiB | P19171/M38240/B45511 | 16 |
| *Arabidopsis thaliana* | PHP[c] | U01880 | 17 |
| *Brassica napus* | Chi | U21848 | 18 |
| *Brassica napus* | Chi2 | Q09023/M95835 | 19 |
| *Hevea brasiliensis* | Hev1[d] | P02877/M36986/A03770/A38288 | 20,21 |
| *Hordeum vulgare* | Chi33 | L34211 | 22 |
| *Lycopersicon esculentum* | Chi9 | Q05538/Z15140/S37344 | 23 |
| *Nicotiana tabacum* | CBP20[e] | S72424 | 24 |
| *Nicotiana tabacum* | Chi | A21091 | 25 |
| *Nicotiana tabacum* (cv. Havana) | Chi | A29074/M15173/S20981/S19855 | 26 |
| *Nicotiana tabacum* (FB7-1) | Chi | JQ0993/S0828 | 27 |
| *Nicotiana tabacum* (cv. Samsun) | Chi | A16119 | 28 |
| *Nicotiana tabacum* (cv. Havana) | Chi | P08252/X16939/S08627 | 27 |
| *Nicotiana tabacum* (cv. BY4) | Chi | P24091/X51599/X64519//S13322 | 26,27,29 |
| *Nicotiana tabacum* (cv. Havana) | Chi | P29059/X64518/S20982 | 26 |
| *Oryza sativum* (IR36) | ChiA | L37289 | 30 |
| *Oryza sativum* | ChiB | JC2253/S42829/Z29962 | 31 |
| *Oryza sativum* | Chi | S39979/S40414/X56787 | 32 |
| *Oryza sativum* (cv. Japonicum) | Chi | X56063 | 33 |
| *Oryza sativum* (cv. Japonicum) | Chi1 | P24626/X54367/S14948 | 34 |
| *Oryza sativum* | Chi2 | P25765/S15997 | 35 |
| *Oryza sativum* (cv. Japonicum) | Chi3 | D16223 | 32 |
| *Oryza sativum* | ChiA | JC2252/S42828 | 30 |
| *Oryza sativum* | Chi1 | D16221 | 32 |
| *Oryza sativum* (IR58) | Chi | U02286 | 36 |
| *Oryza sativum* | Chi | X87109 | 37 |
| *Pisum sativum* (cv. Birte) | Chi | P36907/X63899 | 38 |

TABLE 3-continued

Overview of Enzymes with Chitin-binding Domains

| Source (strain) | Enzyme[a] | Accession No. | Ref.[3] |
|---|---|---|---|
| *Pisum sativum* (cv. Alcan) | Chi2 | L37876 | 39 |
| *Populus trichocarpa* | Chi | S18750/S18751/X59995/P29032 | 40 |
| *Populus trichocarpa* (H11-11) | Chi | U01660 | 41 |
| *Phaseolus vulgaris* (cv. Saxa) | Chi | A24215/S43926/Jq0965/P36361 | 42 |
| *Phaseolus vulgaris* (cv. Saxa) | Chi | P06215/M13968/M19052/A25898 | 43,44,45 |
| *Sambucus nigra* | PR-3[f] | Z46948 | 46 |
| *Secale cereale* | Chi | JC2071 | 47 |
| *Solanum tuberosum* | ChiB1 | U02605 | 48 |
| *Solanum tuberosum* | ChiB2 | U02606 | 48 |
| *Solanum tuberosum* | ChiB3 | U02607/S43317 | 48 |
| *Solanum tuberosum* | ChiB4 | U02608 | 48 |
| *Solanum tuberosum* (cv. Maris Piper) | WIN-1[g] | P09761/X13497/S04926 | 49 |
| *Solanum tuberosum* (cv. Maris Piper) | WIN-2[g] | P09762/X13497/S04927 | 49 |
| *Triticum aestivum* | Chi | S38670/X76041 | 50 |
| *Triticum aestivum* | WGA-1[h] | P10968/M25536/S09623/S07289 | 51,52 |
| *Triticum aestivum* | WGA-2[h] | P02876/M25537/S09624 | 51,53 |
| *Triticum aestivum* | WGA-3[h] | P10969/J02961/S10045/A28401 | 54 |
| *Ulmus americana* (NPS3-487) | Chi | L22032 | 55 |
| *Urtica dioica* | AGL[i] | M87302 | 56 |
| *Vigna unguiculata* (cv. Red caloona) | Chi1 | X88800 | 57 |

[a]NHP: nuclear polynedrosis virus endochitinase like sequence; Chi: chitinase
[b]anti-microbial peptide,
[c]pre-hevein like protein,
[d]hevein,
[e]chitin-binding protein,
[f]pathogenesis related protein,
[g]wound-induced protein,
[h]wheat germ agglutinin,
[i]agglutinin (lectin)
[3]References: Chitin-binding domains
1) Udea et al. (1994) J. Ferment. Bioeng. 78, 205–211
2) Watanabe et al. (1990) J. Biol. Chem. 265, 15659–16565
3) Watanabe et al. (1992) J. Bacteriol. 174, 408–414
4) Gleave et al. (1994) EMBL Data Library
5) Sidhu et al. (1994) J. Biol. Chem. 269, 20167–20171
6) Jones et al. (1986) EMBO J. 5, 467–473
7) Sitrit et al. (1994) EMBL Data Library
8) Genbank entry only
9) Tsujibo et al. (1993) J. Bacteriol. 175, 176–181
10) Yanai et al. (1992) J. Bacteriol 174, 7398–7406
11) Pauley (1994) EMBL Data Library
12) Kuranda et al. (1991) J. Biol. Chem. 266, 19758–19767
13) van Damme et al. (1992) EMBL Data Library
14) Broekaert et al. (1992) Biochemistry 31, 4308–4314
15) de Bolle et al. (1993) Plant Mol. Physiol. 22, 1187–1190
16) Samac et al. (1990) Plant Physiol. 93, 907–914
17) Potter et al. (1993) Mol. Plant Microbe Interact. 6, 680–685
18) Buchanan-Wollaston (1995) EMBL Data Library
19) Hamel et al. (1993) Plant Physiol. 101, 1403–1403
20) Broekaert et al. (1990) Proc. Natl. Acad. Sci. USA 87, 7633–7637
21) Lee et al. (1991) J. Biol. Chem. 266, 15944–15948
22) Leah et al. (1994) Plant Physiol. 6, 579–589
23) Danhash et al. (1993) Plant Mol. Biol. 22 1017–1029
24) Ponstein et al. (1994) Plant Physiol. 104, 109–118
25) Meins et al. (1991) Patent EP0418695-A1
26) van Buuren et al. (1992) Mol. Gen. Genet. 232, 460–469
27) Shinshi et al. (1990) Plant Mol. Biol. 14, 357–368
28) Cornellisen et al. (1991) Patent EP0440304-A2
29) Fukuda et al. (1991) Plant Mol. Biol. 16, 1–10
30) Yun et al. (1994) EMBL Data Library
31) Kim et al. (1994) Biosci. Biotechnol. Biochem. 58, 1164–1166
32) Nishizawa et al. (1993) Mol. Gen. Genet. 241, 1–10
33) Nishizawa et al. (1991) Plant Sci 76, 211–218
34) Huang et al. (1991) Plant Mol. Biol. 16, 479–480
35) Zhu et al. (1991) Mol. Gen. Genet. 226, 289–296
36) Muthukrishhnan et al. (1993) EMBL Data Library
37) Xu (1995) EMBL Data Library
38) Vad et al. (1993) Plant Sci 92, 69–79
39) Chang et al. (1994) EMBL Data Library
40) Davis et al. (1991) Plant Mol. Biol. 17, 631–639
41) Clarke et al. (1994) Plant Mol. Biol. 25, 799–815
42) Broglie et al. (1989) Plant Cell 1, 599–607
43) Broglie et al. (1986) Proc. Natl. acad. Sci. USA 83, 6820–6824
44) Lucas et al. (1985) FEBS Lett. 193, 208–210

TABLE 3-continued

Overview of Enzymes with Chitin-binding Domains

Source (strain)　　　　　　　Enzyme[a]　Accession No.　　　　Ref.[3]

45) Hedrick et al. (1988) Plant Physiol. 86, 182–186
46) Roberts et al. (1994) EMBL Data Library
47) Yamagami et al. (1994) Biosci. Biotechnol. Biochem. 58, 322–329
48) Beerhues et al. (1994) Plant Mol. Biol. 24, 353–367
49) Stanford et al. (1989) Mol. Gen. Genet. 215, 200–208
50) Liao et al. (1993) EMBL Data Library
51) Smith et al. (1989) Plant Mol. Biol. 13, 601–603
52) Wright et al. (1989) J. Mol. Biol. 28, 327–336
53) Wright et al. (1984) Biochemistry 23, 280–287
54) Raikhel et al. (1987) Proc. Natl. acad. Sci. USA 84, 6745–6749
55) Hajela et al. (1993) EMBL Data Library
56) Lerner et al. (1992) J. Biol. Chem. 267, 11085–11091
57) Vo et al. (1995) EMBL Data Library

TABLE 4

Overview of Enzymes Containing Starch-binding Domains

| Source (strain) | Enzyme | Accession No. | Ref.[4] |
|---|---|---|---|
| A. awarori (var. kawachi) | AMYG | P23176/D00427/JT0479 | 1,2 |
| A. niger (T21) | AMYG | S73370 | 3 |
| A. niger -A. awamori | AMYG1/G2 | P04064/A90986/A29166/X00712/X00548 | 4,5,6 |
|  |  | K02465 | 7,8,9 |
| A. oryzae | AMYG (GLAA) | P36914/JQ1346/D01035/S75274/D01108 | 10,11 |
| A. shirousamii | AMYG (GLA) | P22832/JQ0607/D10460 | 12 |
| Bacillus sp. (B1018) | AMY[a] | P17692/M33302/D90112/S09196 | 13 |
| Bacillus sp. (TS-23) | a-AMY | U22045 | 14 |
| Bacillus sp. (1-1) | CGT | P31746/S26399 | 15 |
| Bacillus sp. (6.63) | CGT | P31747/X66106/S21532 | 16 |
| Bacillus sp. (17-1) | CGT | P30921/M28053/A37208 | 17 |
| Bacillus sp. (38-2) | CGT | P09121/M19880/D00129/S24193 | 18,19 |
| Bacillus sp. (1011) | CGT | P05618/A26678/M17366 | 20 |
| Bacillus sp. (DSM 5850) | CGT | A18991 | 21 |
| Bacillus sp. (KC 201) | CGT | D13068 | 15,22 |
| B. cereus (SPOII) | b-AMY | A48961/P36924/S54911 | 23 |
| B. circulans (8) | CGT | P30920/X68326/S23674 | 24 |
| B. circulans (251) | CGT | X78145 | 25 |
| B. licheniformis | CGTA | P14014/X15752/S15920 | 26 |
| B. macerans (IFO 3490) | CGTM (CDG1) | P04830/X5904/S31281 | 27 |
| B. macerans (IAM 1243) | CGT | M12777 | 28 |
| B. macerans | CGT (CDG2) | P31835/S26589 | 29 |
| B. ohbensis | CGT | P27036/D90243 | 30 |
| B. stearothermophilus | AMYM[b] | P19531/M36539/S28784 | 31 |
| B. stearothermophilus (NO2) | CGT | P31797/X59042/S26588/X59043/ | 32 |
|  |  | X59404/S31284 |  |
| C. rolfsii (AHU 9627) | AMYG2 | D49448 | 33 |
| D. discoideum | ORF | S15693/X51947 | 34 |
| H. grisea (var. thermoidea) | GLA1 | M89475 | 35 |
| H. resinae (ATCC 20495) | GAMP | Q03045/X68143/X67708/S31422/S33908 | 36–38 |
| K. pneumoniae (M5A 1) | CGT | P08704/M15264/A29023 | 39 |
| N. crassa (74-OR23-IA) | GLA-1 | P14804/X67291/S13711/S13710/S36364 | 40,41 |
| P. saccharophila (IAM 1504) | MTA[c] | P22963/X16732/S05667 | 42 |
|  |  | 507/M24516/A32803 | 44 |
| S. griseus (IMRU 3570) | AMY | P30270/X57568/S14063 | 45 |
| S. limosus (S. albidoflavus) | AML | P09794/M18244/B28391 | 46 |
| S. violaceus (S. venezuela) (ATCC 15068) | AML | P22998/M25263/JS0101 | 47 |
| Th. curvata (CCM 3352) | TAM[e] | P29750/X59159/JH0638 | 48 |
| Th. thermosulfurogenes (DSM3896/EM1)[f] | AMYA | P26827/X54654/X54982/S17298/S37706 | 49 |
| Th. thermosulfurogenes (ATCC 33743) | AMYB | P19584/M22471/A31389 | 50 |

[a]Raw-starch digesting amylase,
[b]Maltogenic α-amylase,
[c]Maltotetraose-forming amylase (1,4-α-maltotetrahydrolase,
[d]Maltopentaose-forming amylase,
[e]thermostable α-amylase,
[f]formerly Clostridium thermosulfurogenes.
AMYG, GAM and GLA: glucoamylase, AMY or AML: alpha-amylase, CGT: β-cyclodextrin glycosyltransferase or cyclomaltodextrin glucanotransferase, ORF: open reading frame
A.: Aspergillus, B.: Bacillus, C.: Corticium, D.: Dictiostelium, H. grisea: Humicola grisea, H. resinea: Hormoconis resinae (Amorphotheca resinae), K.: Klebsiella, N.: Neurospora, S.: Streptomyces, Th. curvata: Thermomonospora curvata, Th. Thermoanaerobacter.
[4]References Starch-binding Domains
1) Hayashida et al. (1989) Agric. Biol. Chem. 53, 135–141

TABLE 4-continued

Overview of Enzymes Containing Starch-binding Domains

Source (strain)　　　　　　　　Enzyme　　　Accession No.　　　　　　　　Ref.[4]

2) Hayashida et al. (1989) Agric. Biol. Chem. 53, 923–929
3) Zhong et al. (1994) Wei Sheng Wu Hseuh Pao 34, 184–190
4) Boel et al. (1984) EMBO J. 3, 1097–1102
5) Boel et al. (1984) EMBO J. 3, 1581–1583
6) Svensson et al. (1986) Eur. J. Biochem. 154, 497–502
7) Svensson et al. (1983) Carlsberg Res. Commun.. 48, 529–544
8) Nunberg et al. (1984) Mol. Cell. Biol. 4, 2306–2315
9) Flwer et al. (1990) Curr. Genet. 18, 537–545
10) Hata et al. (1991) Agric. biol. Chem. 55, 941–949
11) Hata et al. (1991) Gene 108, 145–150
12) Shibuya et al. (1990) Agric. Biol. Chem. 54, 1905–1914
13) Itkor et al. (1990) Biochem. Biophys. res. Commun. 166, 630–636
14) Lin et al. (1995) EMBL Data Library
15) Schimd et al. (1988) Proceedings of the fourth International symposium on cyclodextrins. Huber, O. and Szejtli, J. Eds. pp 71–76. Kluwer, Academic Publishers.
16) Akhmetzjanov (1992) EMBL Data Library
17) Kaneko et al. (1989) J. Gen. Microbiol. 135, 3447–3457
18) Kaneko et al. (1988) J. Gen. Microbiol. 134, 97–105
19) Hamamoto et al. (1987) Agric. Biol. Chem. 51, 2019–2022
20) Kimura et al. (1987) J. Bacteriol. 169, 4399–4402
21) Patent WO9114770-A1
22) Kitamoto et al. (1992) J. Ferment. Bioeng. 74, 345–351
23) Nanmori et al. (1993) Appl. Environ. Microbiol. 59, 623–627
24) Nitschke et al. (1990) Appl. Microbial. Biotechnol. 33, 542–546
25) Lawson et al. (1994) J. Mol. Biol. 236, 590–560
26) Hill et al (1990) Nucleids Acids Res. 18, 199–199
27) Fujiwara et al. (1992) Appl. Environ. Microbiol. 58, 4016–4025
28) Takano et al. (1986) J. Bacteriol. 166, 1118–1122
29) Sugimoto et al. Patent N° UK2169902
30) Sin et al. (1991) Appl. Microbiol. Biotechnol. 35, 600–605
31) Didericksen et al. (1988) FEMS Microbiol Lett. 56, 53–60
32) Fujiwara et al. (1992) Appl. Environ. Microbiol. 58, 4016–4025
33) Nagasaka et al. (1995) EMBL Data Library
34) Maniak et al. (1990) Nucleic Acids Res. 18, 3211–3217
35) Berka et al. (1992) EMBL Data Library
36) Joutsjoki et al. (1992) FEMS Microbiol Lett. 78, 237–244
37) Vainio et al. (1993) Curr. Genet. 24, 38–44
38) Fagerstrom et al. (1990) J. Gen. Microbiol. 136, 913–920
39) Binder et al. (1986) Gene 47, 269–277
40) Stone et al. (1989) Curr. Genet. 24, 205–211
41) Koh-Laur et al. (1989) Enzym. Microb. Technol. 11, 692–695
42) Zhoe et al. (1989) FEBS Lett. 255, 37–41
43) Shida et al. (1991) Biosci. Biotechnol, Biochem. 56, 76–80
44) Fujita et al. (1989) J. Bacteriol. 171, 1333–1339
45) Vigal et al. (1991) Mol. Gen. Genet. 225, 278–288
46) Long et al. (1987) J. Bacteriol. 169, 5745–5754
47) Virolle et al. (1988) Gene 74, 321–334
48) Petricek et al. (1992) Gene 112, 77–83
49) Bahl et al. (1991) Appl. Environ. Microbiol. 57, 1554–1559
50) Kitamoto et al. (1988) J. Bacteriol. 170, 5848–5854

TABLE 5

Sources of Polysaccharide Binding Domains

| Binding Domain | Proteins Where Binding Domain is Found |
|---|---|
| Cellulose Binding Domains[1] | β-glucanases (avicelases, CMCases, cellodextrinases)<br>exoglucanses or cellobiohydrolases<br>cellulose binding proteins<br>xylanases<br>mixed xylanases/glucanases<br>esterases<br>chitinases<br>β-1,3-glucanases<br>β-1,3-(β-1,4)-glucanases<br>(β-)mannanases<br>β-glucosidases/galactosidases<br>cellulose synthases (unconfirmed) |
| Starch/Maltodextrin Binding Domains | α-amylases[2,3]<br>β-amylases[4,5]<br>pullulanases<br>glucoamylases[6,7]<br>cyclodextrin glucotransferases[8–10]<br>(cyclomaltodextrin glucanotransferases)<br>maltodextrin binding proteins[11] |
| Dextran Binding Domains | (Streptococcal) glycosyl transferases[12]<br>dextran sucrases (unconfirmed)<br>Clostridial toxins[13,14]<br>glucoamylases[6]<br>dextran binding proteins |
| β-Glucan Binding Domains | β-1,3-glucanases[15,16]<br>β-1,3-(β-1,4)-glucanases (unconfirmed)<br>β-1,3-glucan binding protein[17] |

TABLE 5-continued

Sources of Polysaccharide Binding Domains

| Binding Domain | Proteins Where Binding Domain is Found |
|---|---|
| Chitin Binding Domains | chitinases |
| | chitobiases |
| | chitin binding proteins |
| | (see also cellulose binding domains) |
| | Heivein |

[1]Gilkes et al., Adv. Microbiol Reviews, (1991) 303–315.
[2]Sogaard et al., J. Biol. Chem. (1993) 268:22480.
[3]Weselake et al, Cereal Chem. (1983) 60:98.
[4]Svensson et al., J. (1989) 264:309.
[5]Jespersen et al., J. (1991) 280:51.
[6]Belshaw et al., Eur. J. Biochem. (1993) 211:717.
[7]Sigurskjold et al., Eur. J. Biochem. (1994) 225:133.
[8]Villette et al., Biotechnol. Appl. Biochem. (1992) 16:57.
[9]Fukada et al., Biosci. Biotechnol. Biochem. (1992) 56:556.
[10]Lawson et al., J. Mol. Biol. (1994) 236:590.
[11]Sharff et al., Biochemistry (1992) 31:10657.
[12]Lis et al., Appl. Environ. Microbiol. (1995) 61:2040.
[13]von Eichel-Streiber et al., J. Bacteriol. (1992) 174:6707.
[14]von Eichel-Streiber et al., Mol. Gen. Genet. (1992) 233:260.
[15]Klebl et al., J. Bacteriol (1989) 171:6259.
[16]Watanabe et al., J Bacteriol (1992) 174:186.
[17]Duvic et al., J. Biol. Chem. (1990) 265:9327.

Once the most appropriate polysaccharide binding moiety for a particular application has been identified, PBP can be prepared by transforming into a host cell a DNA construct comprising DNA encoding the appropriate polysaccharide binding moiety. The phrase "polysaccharide binding peptide" intends an amino acid sequence which comprises at least a functional portion of the polysaccharide binding region of a polysaccharidase or a polysaccharide binding protein. By "functional portion" is intended an amino acid sequence which binds to an oligosaccharide polymer of interest. Preferably, DNA encoding a growth factor moiety is ligated to the PBP DNA sequence. The fused gene encoding the composition according to formula (1), or the PBP DNA sequence alone, is expressed in a host cell, either an eukarvotic or a prokarvotic cell. Where the PBP alone has been prepared, if desired, the expressed and isolated polysaccharide binding peptide is chemically conjugated to a compound of interest, i.e., a growth factor or other moiety that stimulates or inhibits cell proliferation or activation.

Figure 1:
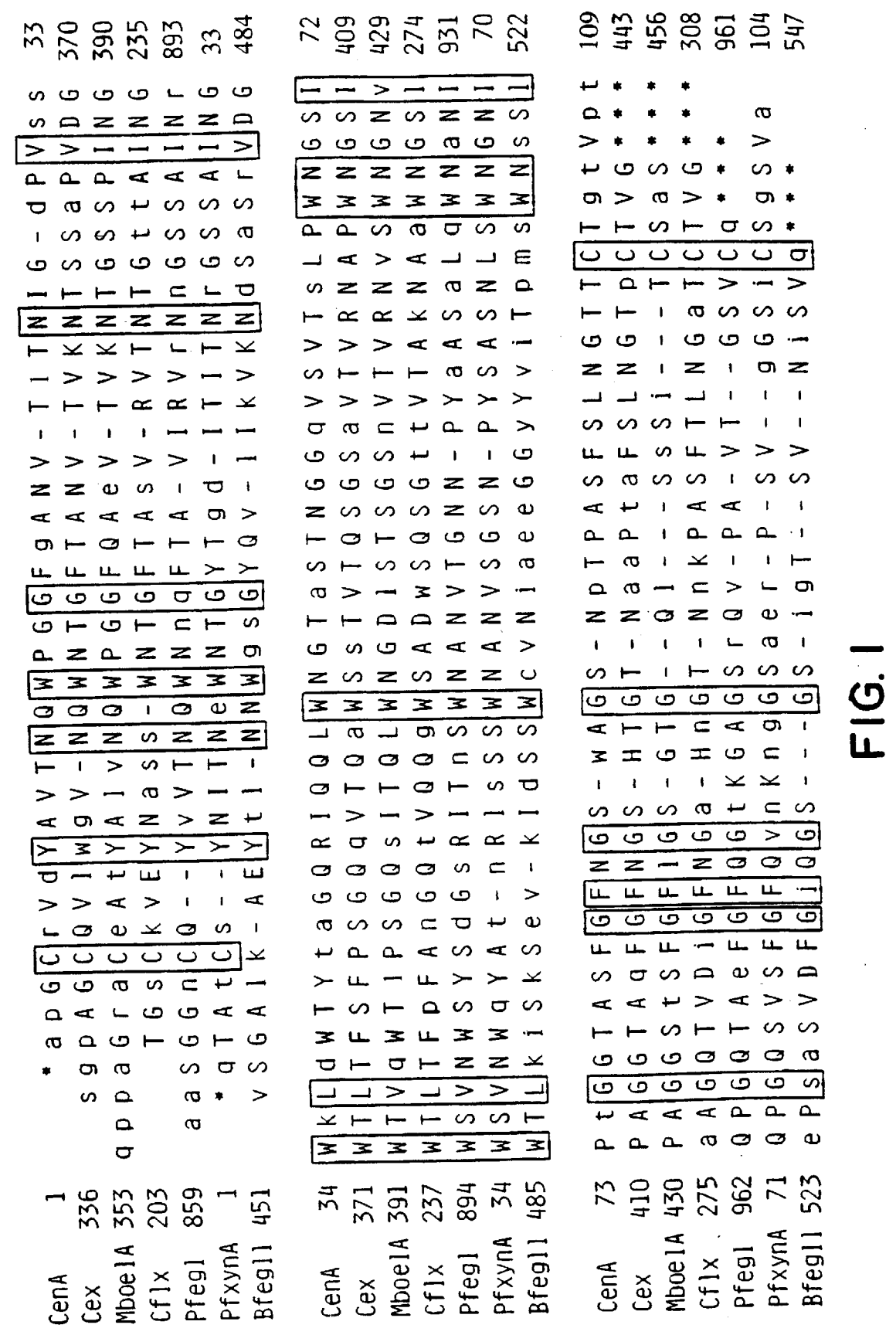

The techniques used in isolating polysaccharidase genes, such as a cellulase gene, and genes for polysaccharide binding proteins are known in the art, including synthesis, isolation from genomic DNA, preparation from cDNA, or combinations thereof. (See, U.S. Pat. Nos. 5,137,819, 5,202, 247, and 5,340,731. ) The sequences for several polypeptide binding domains, which bind to soluble oligosaccharides are known. (See, FIG. 1.) The DNAs coding for a variety of polysaccharidases and polysaccharide binding proteins also are known. Various techniques for manipulation of genes are well known, and include restriction, digestion, resection, ligation, in vitro mutagenesis, primer repair, employing linkers and adapters, and the like (see Sambrook et al., *Molecular Cloning, A Laboratory Manual*, Cold Spring Harbor Laboratory, Cold Spring Harbor, N.Y., 1989).

The amino acid sequence of a polysaccharidase also can be used to design a probe to screen a cDNA or a genomic library prepared from mRNA or DNA from cells of interest as donor cells for a polysaccharidase gene or a polypeptide-binding protein gene. By using the polysaccharidase cDNA or binding protein cDNA or a fragment thereof as a hybridization probe, structurally related genes found in other microorganisms can be easily cloned. Particularly contemplated is the isolation of genes from organisms that express polysaccharidase activity using oligonucleotide probes based on the nucleotide sequences of genes obtainable from an organism wherein the catalytic and binding domains of the polysaccharidase are discrete, although other polysaccharide binding proteins also can be used (see, for example, Shoseyev et al. (1992) *Proc. Nat'l. Acad. Sci.* (*USA*) 89:3483–3487).

Probes developed using consensus sequences for the binding domain of a polysaccharidase or polysaccharide-binding protein are of particular interest. The β-1,4-glycanases from *C. fimi* characterized to date are endoglucanases A, B, C and D (CenA, CenB, CenC and CenD, respectively), exocellobiohydrolases A and B (CbhA and CbhB, respectively), and xylanases A and D (Cex and XylD, respectively) (see Wong et al. (1986) *Gene*, 44:315; Meinke et al. (1991) *J. Bacteriol.*, 173:308; Coutinho et al., (1991) *Mol. Microbiol.* 5:1221; Meinke et al., (1993) *Bacteriol.*, 175:1910; Meinke et al., (1994) *Mol. Microbiol.*, 12:413; Shen et al., *Biochem. J.*, in press; O'Neill et al., (1986) *Gene*, 44:325; and Millward-Sadler et al., (1994) *Mol. Microbiol.*, 11:375). All are modular proteins of varying degrees of complexity (FIG. 1), but with two features in common: a catalytic domain (CD) and a cellulose-binding domain (CBD) which can function independently (see Millward-Sadler et al. (1994) *Mol. Microbiol.* 11:375; Gilkes et al. (1988) *J. Biol. Chem.* 263:10401; Meinke et al. (1991) *J. Bacteriol.* 173:7126; and Coutinho et al. (1992) *Mol. Microbiol.* 6:1242). In four of the enzymes (CenB, CenD, CbhA and CbhB), fibronectin type III (Fn3) repeats separate the N-terminal CD from the C-terminal CBD. The CDs of the enzymes come from six of the families of glycoside hydrolases (see Henrissat (1991) *Biochem. J.* 280:309; and Henrissat et al. (1993) *Biochem. J.* 293:781); all of the enzymes have an N- or C-terminal CBD or CBDs (see Tomme et al., *Adv. Microb. Physiol.*, in press); CenC has tandem CBDs from family IV at its N-terminus; CenB and XylD each have a second, internal CBD from families III and II, respectively. Cex and XylD are clearly xylanases; however, Cex, but not XylD, has low activity on cellulose. Nonetheless, like several other bacterial xylanases (see Gilbert et al. (1993) J. Gen. Microbiol. 139:187), they have CBDs. *C. fimi* probably produces other β-1,4-glycanases. Similar systems are produced by related bacteria (see Wilson (1992) *Crit. Rev. Biotechnol.* 12:45; and Hazlewood et al. (1992) *J. Appl. Bacteriol.* 72:244). Unrelated bacteria also produce glycanases; *Clostridium thermocellum*, for example, produces twenty or more β-1,4-glycanases (see Béguin et al. (1992) *FEMS Microbiol. Lett.* 100:523). For solid phase recovery systems, CBDs that bind insoluble polysaccharides are of particular use. For use in phase separation purification of growth factor conjugates, a particularly useful CBD is the binding domain of *C. fimi* endoglucanase C N1, which is the only protein known to bind soluble cellosaccharides and one of a small set of proteins that are known to bind any soluble polysaccharides.

Examples of suitable binding domains are shown in FIG. 1, which presents an alignment of binding domains from various enzymes that bind to polysaccharides and identifies amino acid residues that are conserved among most or all of the enzymes. This information is used to derive a suitable oligonucleotide probe using methods known to those of skill in the art. The probes can be considerably shorter than the entire sequence but should be at least 10, preferably at least 14, nucleotides in length. Longer oligonucleotides are also useful, up to the full length of the gene, preferably no more than 500, more preferably no more than 250, nucleotides in length. RNA or DNA probes can be used. In use, the probes are typically labeled in a detectable manner, for example, with $^{32}P$, $^3H$, biotin or avidin) and are incubated with single-stranded DNA or RNA from the organism from which a gene is being sought. Hybridization is detected by means of the label after the unhybridized probe has been separated from the hybridized probe. The hybridized probe is typically immobilized on a solid support such as nitrocellulose paper. Hybridization techniques suitable for use with oligonucleotides are well known to those skilled in the art. Although probes are normally used with a detectable label that allows easy identification, unlabeled oligonucleotides are also useful, both as precursors of labeled probes and for use in methods that provide for direct detection of double-stranded DNA (or DNA/RNA). Accordingly, the term "oligonucleotide probe" refers to both labeled and unlabeled forms.

Generally, the binding domains identified by probing nucleic acids from an organism of interest will show at least about 40% identity (including as appropriate allowances for conservative substitutions, gaps for better alignment and the like) to the binding region or regions from which the probe was derived and will bind to a soluble β-1,4 glucan with a $K_a$ of $\geq 10^3 M^{-1}$. More preferably, the binding domains will be at least about 60% identical, and most preferably at least about 70% identical to the binding region used to derive the probe. The percentage of identity will be greater among those amino acids that are conserved among polysaccharidase binding domains. Analyses of amino acid sequence comparisons can be performed using programs in PC/Gene (IntelliGenetics, Inc.). PCLUSTAL can be used for multiple sequence alignment and generation of phylogenetic trees.

In order to isolate the PBP of a polysaccharidase or a polysaccharide binding domain from an enzyme or cluster enzyme that binds to a polysaccharide, several genetic approaches can be used. One method uses restriction enzymes to remove a portion of the gene that codes for portions of the protein other than the PBP. The remaining gene fragments are fused in frame to obtain a mutated gene that encodes a truncated protein. Another method involves the use of exonucleases such as Bal31 to systematically delete nucleotides either externally from the 5' and the 3' ends of the DNA or internally from a restricted gap within the gene. These gene deletion methods result in a mutated gene encoding a shortened protein molecule which can then be evaluated for substrate or polysaccharide binding ability. Appropriate substrates for evaluating and binding activity include those for the enzymes listed in Tables 1–5 above, as well as the carboxhydrates listed in Table 6 below.

Similarly, a gene that codes for a growth factor or other moiety that modulates cell proliferation, activation, or differentiation can be modified to remove coding regions for portions of the factor that are not essential for carrying out the desired biological activity, such as the trarismembrane domain, which is preferably deleted when constructing a chimeric gene that encodes a growth factor conjugate. The protein encoded by the truncated gene is tested for its ability to perform the desired biological activity.

Once nucleotide sequences encoding the polysaccharide binding region and the growth factor moiety have been identified, either as cDNA or chromosomal DNA, they can then be manipulated in a variety of ways to prepare a composition where the expression product has a structure represented by formula (1) above. The nucleotide sequence that codes for the polysaccharide binding region may be fused to a DNA sequence encoding a growth factor. It is highly desirable that the three-dimensional structure of the component polypeptides be retained. Depending upon the source of the fragments and the length of the desired polypeptide, one or more restriction sites can be designed into the synthetic genes used to construct chimeric polypeptides. If possible, the restriction site(s) leaves the amino acid sequence of the polypeptide unaltered. However, in some case incorporation of a new restriction site(s) may yield an altered amino acid sequence without changing the activity of the protein.

During the construction of the expression cassette, various fragments of the DNA are usually cloned in an appropriate cloning vector, which allows for amplification of the DNA, modification of the DNA or manipulation by joining or removing of sequences, linkers, or the like. Normally, the vectors are capable of replication in at least a relatively high copy number in bacteria. A number of vectors are readily available for cloning in gram-negative bacteria, especially *E. coli*, including such vectors as pBR322, pTZ, pUC and the like. The cloning vectors are characterized by having an efficient replication system functional in the host bacterium. The cloning vector generally has at least one unique restriction site, usually a plurality of unique restriction sites, and also can include multiple restriction sites. In addition, the cloning vector will have one or more markers which provide for selection of transformants. The markers normally provide resistance to cytotoxic agents such as antibiotics, heavy metals, toxins or the like, complementation of a mutation that renders the host auxotrophic, or immunity to a phage. By appropriate restriction of the vector and the cassette, and, as appropriate, modification of the ends, by chewing back or filling in overhangs, to provide for blunt ends, by addition of linkers, by tailing, complementary ends are provided for ligation and joining of the vector to the expression cassette or component thereof.

After each manipulation of the DNA in the development of the cassette, the plasmid is isolated and, as required, the particular cassette component analyzed as to its sequence to insure that the proper sequence has been obtained. Depending upon the nature of the manipulation, the desired fragment is excised from the plasmid and introduced into a different vector or the plasmid is restricted and the expression cassette component manipulated, as appropriate. In some instances, a shuttle vector is employed which is capable of replication in different hosts requiring different replication systems. This may or may not require additional markers that are functional in the two hosts. Where such markers are required, these can be included in the vector so that the plasmid containing the cassette, two replication systems and the marker(s) can be transferred from one host to another, as required. For selection, any useful marker can be used. Examples of suitable selectable markers include genes that confer resistance to ampicillin, tetracyline, hygromycin B, G418, and/or neomycin and the like. However, although a marker for selection is highly desirable for convenience, other procedures for screening transformed cells are known to those skilled in the art, for example, transformed cells can be screened by the specific products they make; synthesis of the desired product may be determined by immunological or enzymatic methods.

The DNA encoding the growth factor conjugate is manipulated in a variety of ways to provide for expression. For example, the gene that codes for the PBP and the growth factor moiety is operably linked to appropriate transcriptional and/or translational signals that are operable in the desired host organism. Suitable host organisms include microbes such as prokarvotes, including *E. coli*, Streptomyces, and Bacillus, and eukaryotes such as the yeasts Saccharomyces (esp. *S. cerevisiae*) and *Pichia pas-*

*toris*. Mammalian and other higher eukaryotic cells also are useful for expression of the growth factor conjugates. Illustrative transcriptional regulatory regions or promoters include, for bacteria, the lac promoter, the trp promoter, the Tac promoter (which is a hybrid of the trp and lac promoters); the lambda left and right promoters, and the like. The transcriptional regulatory region can additionally include regulatory sequences which allow the time of expression of the fused gene to be modulated, for example, by the presence or absence of nutrients or expression products in the growth medium. temperature, etc. For example, expression of the fused gene can be regulated by temperature using a regulatory sequence comprising the bacteriophage lambda PL promoter, the bacteriophage lambda OL operator and a temperature sensitive repressor. Regulation of the promoter is achieved through interaction between the repressor and the operator. A preferred promoter is the strong glucose-repression insensitive Tac promoter. Examples of high level expression vectors are described in Graham et al. (1995) *Gene* 158:51–54.

Methods for synthesis of heterologous proteins in yeast are well known. *Methods in Yeast Genetics*, Sherman et al. ((1982) Cold Spring Harbor Laboratory Press) is a well recognized work describing the various methods available to produce a growth factor conjugate in yeast. Suitable vectors for expression in yeast usually have expression control sequences, such as promoters, including 3-phosphoglycerate kinase or other glycolytic enzymes, and an origin of replication, termination sequences and the like as desired. Suitable vectors include those described in the literature (see, for example, Botstein et al. (1979) *Gene* 8:17–24; Broach et al. (1979) *Gene* 8:121–133). Expression vectors that are suitable for use in various eukaryotic host cells are produced by several commercial manufacturers of biological reagents (See, e.g., product catalogs from Stratagene Cloning Systems, La Jolla Calif.; Clontech Laboratories, Palo Alto Calif.; Promega Corporation, Madison Wis.).

A number of suitable mammalian host cell lines capable of expressing the growth factor conjugates have been developed in the art, and include the HEK293, BHK21, and CHO cell lines, and various human cells such as COS cell lines, HeLa cells, myeloma cell lines, Jurkat cells, and the like. Expression vectors for these cells can include expression control sequences. such as an origin of replication, a promoter (e.g., the CMV promoter, a HSV tk (thymidine kinase) promoter or pgk (phosphoglycerate kinase) promoter), an enhancer (Queen et al. (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Insect cells are another eukaryotic system that is useful for expressing the growth factor conjugates. Appropriate vectors for expressing growth factor conjugates in insect cells usually are derived from the SF9 baculovirus. Suitable insect cell lines include mosquito larvae, silkworm, armyworm, moth and Drosophila cell lines such as a Schneider cell line (See, Schneider (1987) *Embryol. Exp. Morphol.* 27:353–365).

The expression cassette can be included within a replication system for episomal maintenance in an appropriate cellular host or can be provided without a replication system, in which the vector can become integrated into the host genome. The DNA can be introduced into the host in accordance with known techniques, such as transformation, using calcium phosphate-precipitated DNA, transfection by contacting the cells with a virus, microinjection of the DNA into cells or the like.

Once the DNA encoding the growth factor conjugate has been introduced into the appropriate host, the host can be grown to express the conjugate. The recombinant products can be glycosylated or non-glycosylated, having the wild-type or other glycosylation. The amount of glycosylation depends in part upon the sequence of the particular peptide, as well as the organism in which it is produced. Thus, expression of the product in *E. coli* cells results in an unglycosylated product, and expression of the product in insect cells generally results in less glycosylation than expression of the product in mammalian cells. Expression in yeast can result in hyperglycosylation.

For isolation of the growth factor conjugate, where the product is retained in the host cell, the cells are harvested, lysed and the product isolated and purified using methods known to those of skill in the art. In some instances, it can be desirable to provide for a signal sequence (secretory leader) upstream of and in reading frame with the structural gene, which provides for secretion of the growth factor conjugate. Illustrative secretory leaders include the secretory leaders of penicillinase, immunoglobulins, T-cell receptors, outer membrane proteins, and the like. By fusion in proper reading frame the growth factor conjugate can be secreted into the medium or the periplasmic space of bacteria In bacterial expression systems such as *E. coli*, a significant fraction leaks into the extracellular media (Ong et al. (1993) *Biotech. Bioeng*. 42:401). Where the product is secreted, the nutrient medium can be collected and the product isolated using procedures known to those of skill in the art. To produce an active protein it can be necessary to allow the protein to refold.

In a preferred embodiment, the growth factor conjugate is purified by affinity chromatography. Substrate binding region is bound to an appropriate substrate, or a different affinity tag that is incorporated into the growth factor conjugate is used. For example, the growth factor conjugate can be constructed so as to include an affinity tag such as hexahistidine, streptavidin, or GST; such affinity tags are useful for affinity purification using, e.g., nickel-Sepharose, biotin, and glutathione respectively.

The growth factor conjugates of the invention generally are immobilized on a substrate of the polysaccharidase binding peptide. By "immobilized" is meant that the growth factor conjugates are bound to suitable substrates, either insoluble or soluble, which include, for example, insoluble polysaccharides such as: cellulose, a polysaccharide composed of D-glucopyranose units joined by $\beta$-1,4-glycosidic linkages and its esters, e.g., cellulose acetate; xylan, in which the repeating backbone unit is $\beta$-1,4-D-xylopyranose; chitin, which resembles cellulose in that it is composed of $\beta$-1,4-linked N-acetyl, 2-amino-2-deoxy-$\beta$-D-glucopyranose units. Other oligosaccharides that are of use include $\alpha$-1,4-glycans such as starch. Enzymes that are capable of binding to polysaccharides, such as those listed above, are of interest in the subject invention as a source of amino acid sequences capable of binding to such substrates. The substrates are useful in forms that include microcrystalline cellulose, cotton, paper, hollow cellulose fibers, microcarriers (e.g., Cellsnow™, Kirin Brewing Co., Japan), sponges, wound coverings, and the like. Generally, the conjugates are not internalized or consumed by cells that are placed in contact with the growth factor conjugates.

The growth factor conjugates find use immobilized on a substrate for the binding protein portion of the conjugate, for ex vivo cultivation of growth-factor dependent cells, particularly cells of the hematopoietic system such as stem cells, as well as megakaryocytes and T-lymphocytes. For example, the methods are useful for cultivation of components of bone marrow such as pre-CFU-S, BFU-E, MK, CFU-MK, GEMM, and GM. The methods involve growing cells responsive to the growth factor in contact with the immobilized growth factor conjugate. In a preferred embodiment, the growth factor conjugate is immobilized on a substrate of the polysaccharidase, for example, a β-1,4-glycan or other polysaccharide as described herein. The substrate can optionally be reversibly or irreversibly bound to a solid support or can itself comprise a solid support (e.g., cotton fabric, paper, cellulose hollow fiber, growth chamber, microcamrer, etc.). Since the immobilized factors generally are not consumed by the cell cultures, the factors provide a continuous localized stimulus for cell proliferation, activation, and/or differentiation. The cell cultures can be in culture plates, growth chambers, and the like, particularly perfusion cultures in which growth medium is continuously added and removed to allow long-termn cell proliferation and/or large scale expansion of a cell population. Cells that can be cultured in perfusion culture include specific effector T cells, stem cells obtained from bone marrow or blood, megakaryocytes or other hematopoietic cells, and the like.

The growth factors also can be bound via the PBP to an extracorporeal device that contains a substrate for the PBP, e.g., a paper filter or a hollow fiber, and the device used for the ex vivo expansion of growth factor dependent cells. For example, blood from a patient in need of expansion, activation, or differentiation of a particular growth factor dependent cell type can be passed through an extracorporeal device within which a growth factor conjugate is immobilized on a solid support that contains a substrate for the polysaccharidase from which the substrate binding domain was obtained to construct the growth factor conjugate. In one embodiment, the growth factor conjugate is bound to a cellulose matrix such as a hollow fiber that is present within the extracorporeal device. Growth factor dependent cells that are passed through the fiber thus contact the immobilized growth factor moiety, which stimulates proliferation, activation, or differentiation of the cells. An example for which this method is useful is the activation of anti-tumor T cells by passing a cancer patient's blood through a extracorporeal device that contains a polysaccharide to which is bound a growth factor conjugate that comprises interleukin-2.

The claimed methods are also useful for cultivating factor dependent cells that require specific local concentrations or gradients of factors, such as nerve cells. A gradient is generated by methods known to those of skill in the art. For example, flow techniques can be used to generate a gradient by contacting a polysaccharide matrix with a solution of a PBP-growth factor conjugate. Proximal regions of the matrix adsorb the highest amount of conjugate from the flow stream.

The growth factor conjugates can be used to obtain a population of cells that is enriched in cells that are dependent upon a particular growth factor or other moiety for proliferation or differentiation. Cells that carry a cell surface receptor for the growth factor are contacted with a growth factor conjugate that is immobilized on a substrate for the polysaccharidase from which the substrate binding domain was derived. If an insoluble substrate is used, undesired cells are removed from the immobilized growth factor dependent cells by washing.

Cells immobilized on a soluble oligosaccharide substrate can be separated from other non-bound cells using, for example, a phase separation system, in particular an aqueous two-phase extraction system. The phase separation system generally comprises two phases which are generated by the incompatibility of the components of the phase separation system upon mixing of the components. One component of the system is a phase forming oligosaccharide polymer and a second component is a phase-inducing agent, such as a second polymer, which is incompatible with the phase-forming oligosaccharide polymer, or a strong electrolyte, particularly a salt, such as a sulfate or citrate salt, which is present at a sufficiently high concentration to induce phase separation. For purification of viable cells, the phase separation conditions must be compatible with cell viability. Examples of polymer pairs capable of forming partition systems with comparable properties to, but lower cost than, the classic dextran/PEG system, including those based, like the dextran/PEG system, on the incompatibility between a carbohydrate and a poly(oxy-ether) are many (see Skuse et al. (1992) *Enzyme Microb. Technol.* 14:785.) Examples include, hydroxypropyl starch (Tjerneld et al. (1986) *Enzyme Microb. Technol.* 8:417), maltodextrins (Szlag et al. (1990) *ACS Symposium Series* 419:38–52), hydroxypropyl cellulose (Skuse et al., supra.), and carboxymethyl cellulose (Albertsson (1971) *Partition of Cell Particles and Macromolecules*, Wiley Interscience) have all been successfully used to form partition systems with PEG. In order to develop a system, phase equilibria data are obtained for the combination of the first and second components selected, using the procedure of Haynes et al. ((1989) *Fluid Phase Equilibria* 53:463) to determine the total polymer concentration, or polymer and other phase inducing agent concentration, above which a stable two-phase partition system is formed. In general, the PBP-conjugates can be bound to a phase forming oligosaccharide at neutral pH in a medium ionic strength buffer of from about $10^{-3}$M to about 1M. Binding can be performed at temperatures from 4° C. to at least 70° C. depending on the components of the phase separation system. Binding is virtually instantaneous and the temperature is not critical. Once the PBP-conjugate is bound to the phase-forming oligosaccharide, it partitions into that phase.

In use, cells bound to the soluble oligosaccharide via a polysaccharide binding peptide are added to the phase partition system which is already mixed, or the composition can be added to a dry form (e.g., lyophilized) of either of the components, generally the oligosaccharide polymer, which is thereby rehydrated, and the other component can then be added. For some applications, more than two phases can be used. After a time sufficient for the conjugate-bound to partition into the oligosaccharide polymer phase, the phases are separated. Partitioning (nonaffinity) of contaminant proteins into the polysaccharide-rich phase is minimized by adjusting the system pH, polymer concentrations, and addition of partitioning electrolytes. Under optimal conditions of operation, multistage contacting of the two aqueous phases then provides either complete or partial (but sufficient) purification of the target composition. In Table 6 below is a partial list of oligosaccharides known to form aqueous two-phase systems with either another polymer or a strong electrolyte.

Other polysaccharides which form two-phase systems include: mixtures of low-molecular weight cellosaccharides; chitosan and other chitin derivatives; water-soluble glucans (α, β, and/or mixed linkage with degree of polymerization>3), modified glucans, and/or derivatized glucans; cereal β-glucans such as barley or oat β-glucans; and mannans, glucommannans, galactomannans, and xyloglucans.

For some applications, it is desirable to release the immobilized cells after the concentration step. Several methods can be used to remove immobilized growth factor conjugates and/or attached cells from a polysaccharide substrate polymer. For example, PBP compounds bind specifically and strongly to the oligosaccharide polymer but can be removed easily by elution with a low ionic strength solution (such as water), or a high pH solution a chaotropic salt These methods can release the entire conjugate from the oligosaccharide polymer, together with any attached cell and/or receptor. The temperature for desorption is not critical and generally in the range of 10° C.–40° C., although ambient temperatures are generally preferred, i.e., about 20° C. Physiologically compatible conditions are used when viable cells are desired. For example, a low ionic strength, physiological pH solution that lacks chaotropic salts can be used to release cells from a substrate.

If viability of cells attached to the growth factor conjugate is not of concern, for example, where the receptor for the growth factor itself or the growth factor receptor pair is being purified, a pH 9.5 carbonate buffer or 6M guanidine HCl can be used for this desorption step. Dilute sodium hydroxide (about 0.1M) can be used in some cases. The nature of the PBP can be modified to alter its adherence properties so that it can, or, if desired, cannot be desorbed by water. Application of the desorption medium to the matrix causes release of the conjugate from the oligosaccharide polymer.

For isolation of the PBP-conjugate and associated cells following release from the substrate, various techniques can be used. For example, the polysaccharide surface can be washed free of the PBP-conjugate with the desorption solution as described above. The PBP-conjugate then is separated from the desorption solution, for example, by changing its ionic strength or pH and readsorbing the PBP-conjugate on an ion exchange medium or on a second polysaccharide matrix.

TABLE 6

Phase-Forming Oligosaccharides

| Uncharged Polysaccharides[5] | Charged Polysaccharides | Low Molecular Weight |
|---|---|---|
| Dextran | Na carboxymethyl dextran | Dextrins derived from cellulose (Cellotriose, cellotetraose, etc.) |
| Hydroxypropyl dextran | Na carboxymethyl xylotriose, etc. | Xylose, xylobiose, cellulose |
| Carboxymethyl dextran | Na dextran sulfate | Maltodextrins and derivatives |
| Maltodextrin | DEAE dextran | |
| Arabinogalactan | Polygalacturonic acid (pectin) | |
| Hydroxypropyl starch | | |
| Amylopectin | | |
| Methyl cellulose | | |
| Hydroxyethyl cellulose | | |
| Ethylhydroxyethyl cellulose | | |
| Carboxymethyl cellulose | | |
| Hydroxypropyl cellulose | | |
| Ficoll | | |
| Carboxymethyl starch | | |
| Hydroxyethyl starch | | |
| Pullulan | | |

[5]Polymers can be crude or purified

Alternatively, cells or other ligands immobilized on a polysaccharide substrate can be released from the substrate by cleaving the growth factor conjugate by proteolysis using either a nonspecific general protease such as proteinase K or trypsin, or a specific protease. A non-specific protease can be used to completely degrade the PBP portion of the PBP complex thus releasing it from the oligosaccharide polymer. For example, release can be effected by treatment by proteinase K at a concentration of about 50 $\mu$g/ml for about 20 minutes at about 37° C. Din et al. (1991) Bio/Technology, 9:1096–1099. A specific protease can also be used to release bound compounds and/or cells from a polysaccharide substrate to which they are bound. For example, one can include a protease recognition site or a chemical cleavage site between the growth factor moiety and the PBP. The PBP remains bound to the oligosaccharide polymer. Examples of recognition sites include those for collagenase, thrombin, enterokinase, and Factor Xa which are cleaved specifically by the respective enzymes. Suitable expression systems for Factor $X_a$ and for Factor $X_a$-CBD fusion proteins have been developed (see Assouline et al. (1993) Protein Eng., 7:787). One of the two native isoforms of steel factor (KL-1) contains a protease cleavage site within its extracelluar domain (Huang et al. (1992) Mol. Cell. Biol. 3: 349–362; Pandiella et al. (1992) J. Biol. Chem. 267: 24028–24033); cleavage at this site by a protease is thus a means for releasing the steel factor moiety of a growth factor conjugate from a PBP. Chemical cleanxage sites sensitive, for example, to low pH or cyanogen bromide, can also be used. The PBP thus provides a means of attaching cells to the oligosaccharide polymer, which cells later can be removed.

Where cleavage is used, the growth factor moiety and attached ligand and/or cell can be cleaved readily from the polysaccharide binding region by the use of a protease specific for a sequence present between the polysaccharide binding region and the growth factor moiety leaving the PBP bound to the oligosaccharide polymer. Preferably, the protease is provided in a form which will facilitate its removal following cleavage of the growth factor moiety from the PBP. As an example, the cleavage protease can be prepared as a cleavage enzyme complex, wherein the protease is bound to a second polysaccharide binding moiety having a substrate specificity different from that of the first polysaccharide binding moiety bound to the polypeptide of interest and/or having different binding characteristics (Assouline et al. (1993) supra.; Assouline et al. (1995) Biotechnol. Prog. 11: 45–49). Thus, cleavage of the binding domain from the recombinant protein of interest can be done in solution and the cleavage enzyme complex then removed by binding to a polysaccharide substrate to which the first polysaccharide binding moiety does not bind. Alternatively, the cleavage enzyme complex can be immobilized on a polysaccharide matrix to which the first polysaccharide binding moiety does not bind. (See Assouline el al (1993) supra; Assouline et al (1995) supra) The purified cells or growth factor moiety are released from the oligosaccharide polymer free of contaminating PBPs which remain bound to the polymer.

The methods for concentrating growth factor dependent cell types and/or receptors can be performed in batch mode, or by passing a cell suspension through a column. For example, the growth factor conjugates can be bound to a polysaccharide matrix contained within an affinity chromatography column or other appropriate purification system. The conjugate is contacted with a sample mixture that contains a ligand that binds to the growth factor moiety, including ligands that are cell-bound, under ionic conditions that allow binding of the ligand to the growth factor conjugate. Unbound molecules and/or cells are then removed by washing the matrix. The bound molecules and/or cells are then isolated by washing the matrix with a buffer that elutes the bound molecules.

The growth factor conjugates also can be used for enhancing wound healing by contacting a wound with a growth factor conjugate, generally one that is bound to a polysaccharide substrate to which the conjugate binds, such as cotton, for example in a bandage. The growth factor moiety used in the claimed methods is one that is chemotactic for cells involved in wound healing. Alternatively, the growth factor can stimulate proliferation of cells involved in wound healing, or inhibit proliferation of cells to prevent or minimize scar tissue formation. The growth factor conjugate is administered to the wound site in an amount effective to enhance cell migration to the wound site and/or modulation of target cell growth.

Other therapeutic applications include the enhancement of nerve regeneration. For example, a conjugate that includes brain derived neurotrophic factor and/or nerve growth factor is immobilized on a polysaccharide substrate such as a membrane via the polysaccharide binding peptide moiety of the conjugate and applied to nerve tissues damaged by injury or illness (see, e.g., U.S. Pat. No. 5,229,500). The immomibilized conjugate is then placed in the proximity of the damaged nerve for a sufficient time to result in partial or total regeneration of the nerve.

The following examples are offered by way of illustration and not by way of limitation.

EXAMPLES

Abbreviations pNPC=p-nitrophenyl-β-D-cellobioside;

HPA=hide powder axure;

gCenA and gCex=the glycosylated forms of CenA and Cex from C. fimi, ngCenA and ngCex=the non-glycosylated forms of CenA and Cex from recombinant E. coli;

RPC=reverse-phase chromatography;

SDS-PAGE=sodium dodecyl sulfate-polyacrylamide gel electrophoresis;

α-Pro/Thr=rabbit antiserum directed against synthetic Cex Pro/Thr box;

PMSF=phenyl-methylsulfonyl fluoride.

Biological Culture Deposits

The following deposits have been made with the American Type Culture Collection (ATCC), 10801 University Boulevard, Manassas, Va. 20110-2209. A derivative of the cloned gene CenA on plasmid pcEC-2 in *Escherichia coli* C600 was deposited on Apr. 23, 1986 and given ATCC Accession No. 67101. A derivative of the cloned gene Cex on plasmid pEC-1 was deposited on May 27, 1986 and given ATCC Accession No. 67120. *E. coli* JM83, pUC12-1.1 cex was deposited on Apr. 23, 1986 and given ATCC Accession No.67102. The full nucleotide sequences of pTugA (Accession Number L24193) pTugAS (Accession Number L24367), *C. fimi* CenA (Accession Number M15823), and *C. fimi* CenC (Accession Number X57858) have been deposited with GenBank.

Example 1

Construction of a Fusion Gene Encoding Steel Factor and a Cellulase Binding Domain The fusion protein SLF-CBD comprises the extracellular domain of steel factor (FIG. 2A) linked to the cellulose binding domain of the *Cellulomonas fimi* exoglucanase Cex (FIG. 2B) to create a fusion between steel factor (SLF) and the cellulose binding domain of Cex ($CBD_{Cex}$), as shown in FIG. 2C. In the native Cex enzyme the catalytic domain is separated from the binding domain by a PT linker consisting of a series of repeating proline-threonine units. This linker was included in the SLF-CBD construct to separate the two domains. A Factor Xa proteolytic cleavage site was introduced between the two domains, upstream of the PT linker, to facilitate the removal of the CBD if necessary. A hexahistidine affinity tag was added to the amino terminus of the protein so that it could be purified using either cellulose (Greenwood et al. (1990) *Cell* 63: 203–211) or nickel-Sepharose (Laemmli (1970) *Nature* 227: 680–685) as a matrix. When properly processed with the removal of the Cex signal peptide, SLF-CBD has a predicted molecular weight of 34.1 kDa. Enzymes and buffers were purchased from GIBCO BRL (Grand Island, N.Y.). All genetic manipulations were carried out in the *Escherichia coli* (*E. coli*) strain DH5a (Hanahan (1983) *J. Mol. Biol.* 166: 557–580).

Figure 3B:
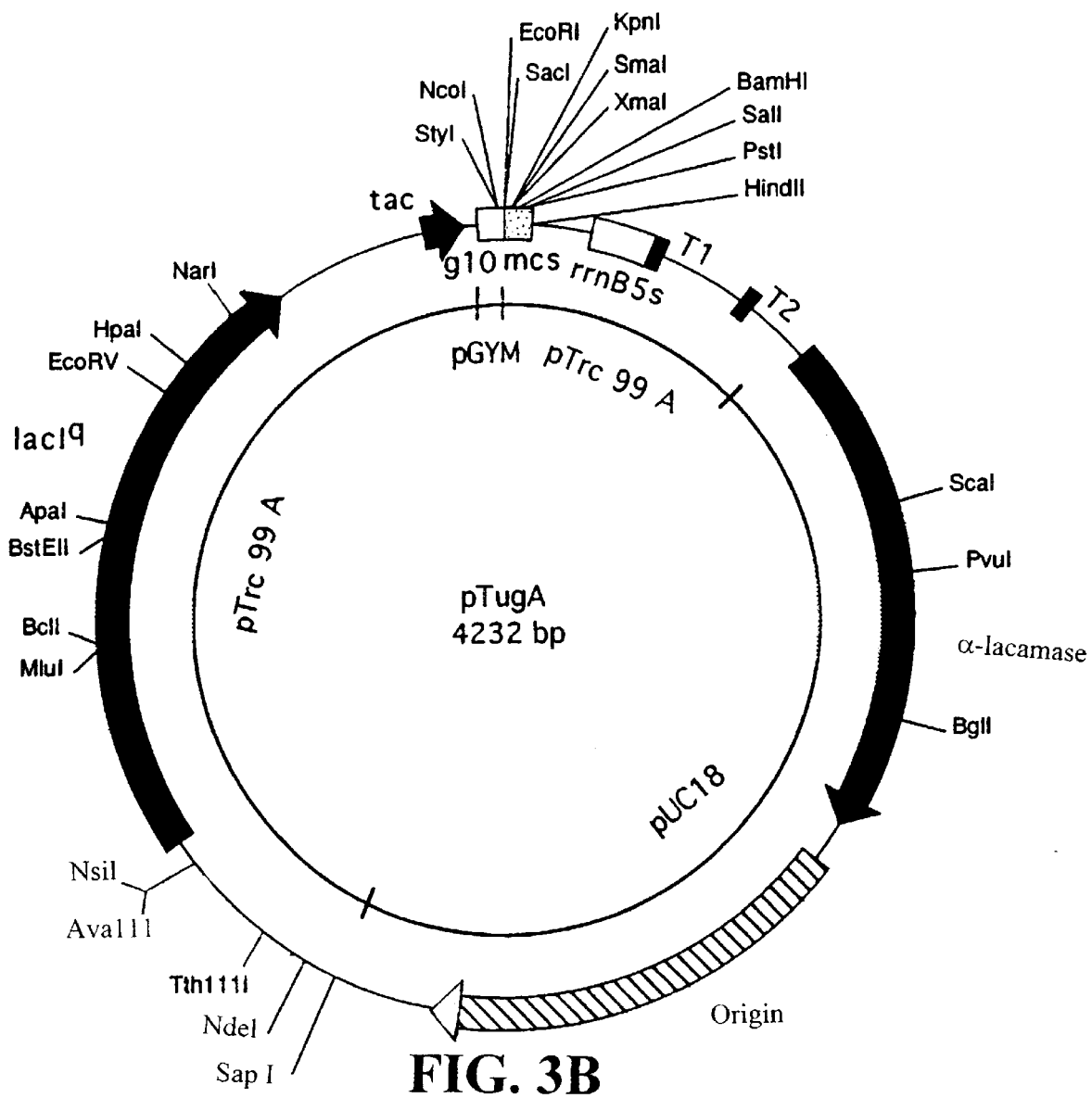
FIG. 3B shows the pTugA vector map.
Figure 4B:
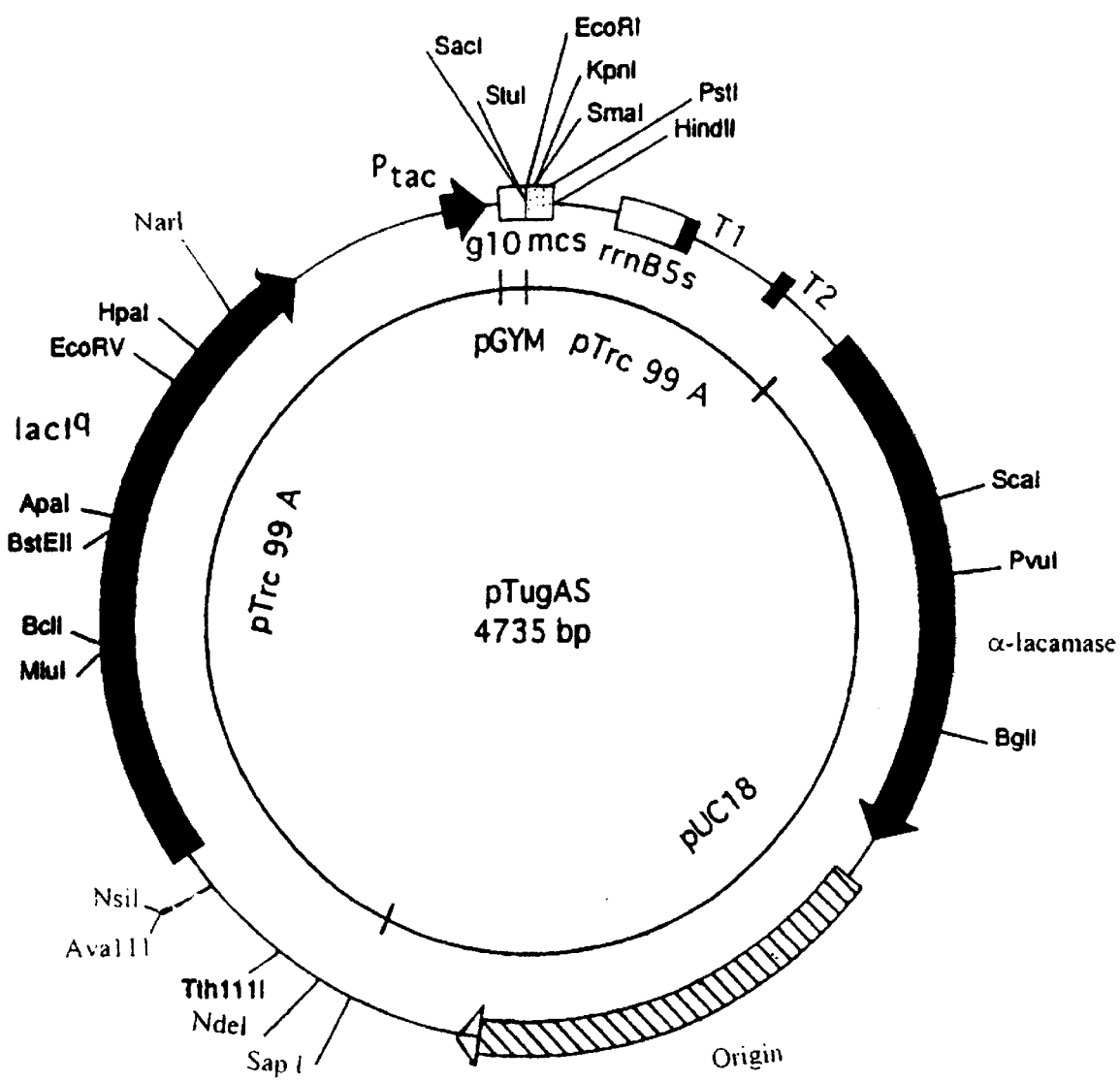
FIG. 4B shows the pTugAS vector map.
Figure 5:
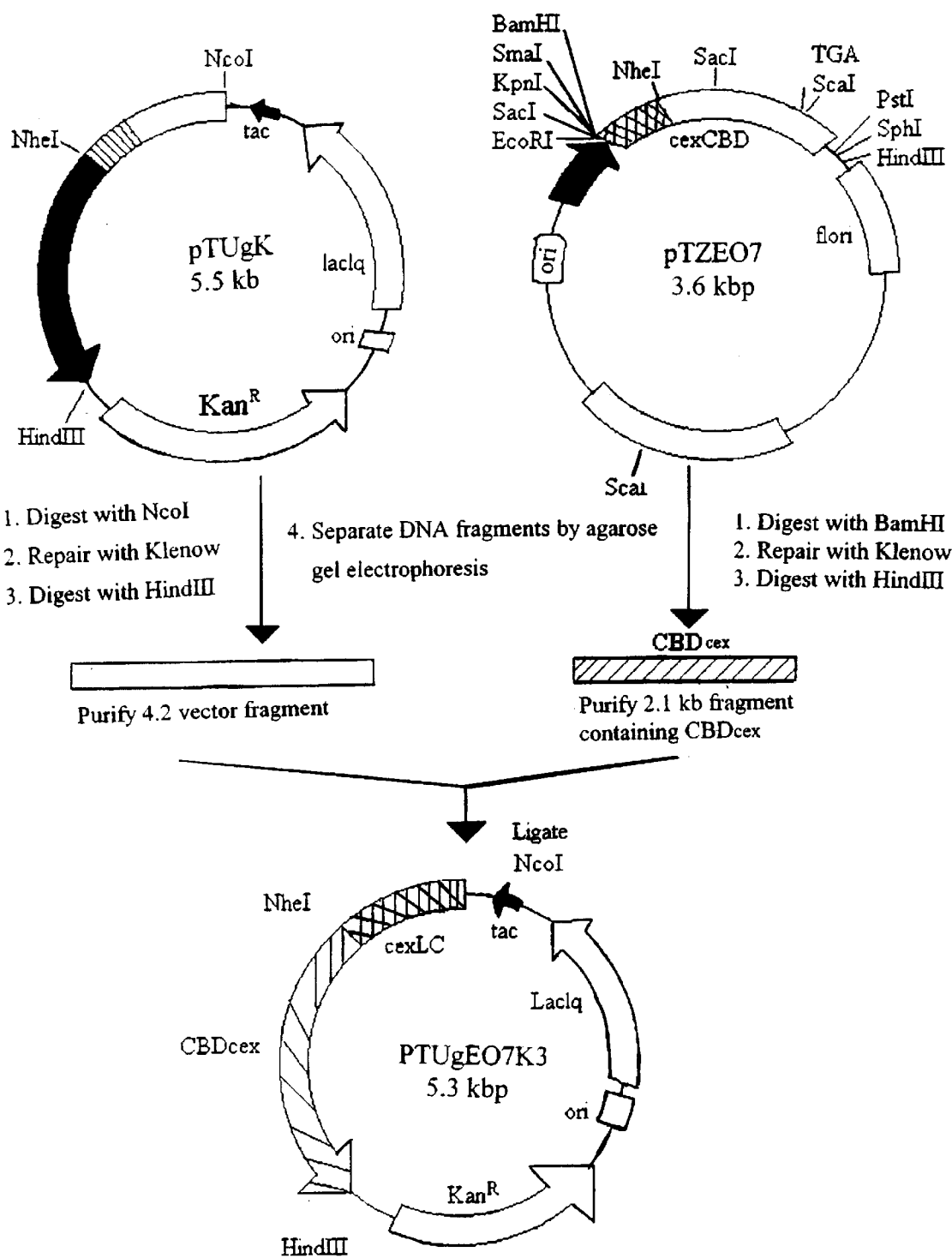
FIG. 5 shows the construction of pTugEO7K3. pTugK, a derivative of pTugA which carries the selective marker for kanamycin resistance in place of the selective marker for ampicillin resistance, was digested completely with NcoI. The staggered end was repaired with the *Escherichia coli* DNA polymerase I (Kienow fragment) to create a blunt ended restriction site. The modified pTugK vector was then digested completely with HindIII and the 4.2 kbp fragment was isolated. pTZE07 (Ong et al. *Biotechnol. Bioeng.* (1993) 42:401–409) was digested completely with BamHI and the staggered end was repaired with the *Escherichia coli* DNA polymerase I (Klenow fragment) to create a blunt ended restriction site. The modified pTZE07 was then digested completely with HindIII and the 2.1 kbp fragment was isolated. The 4.2 and 2.1 kbp fragments were ligated to give pTugEO7K3.
Figure 6:
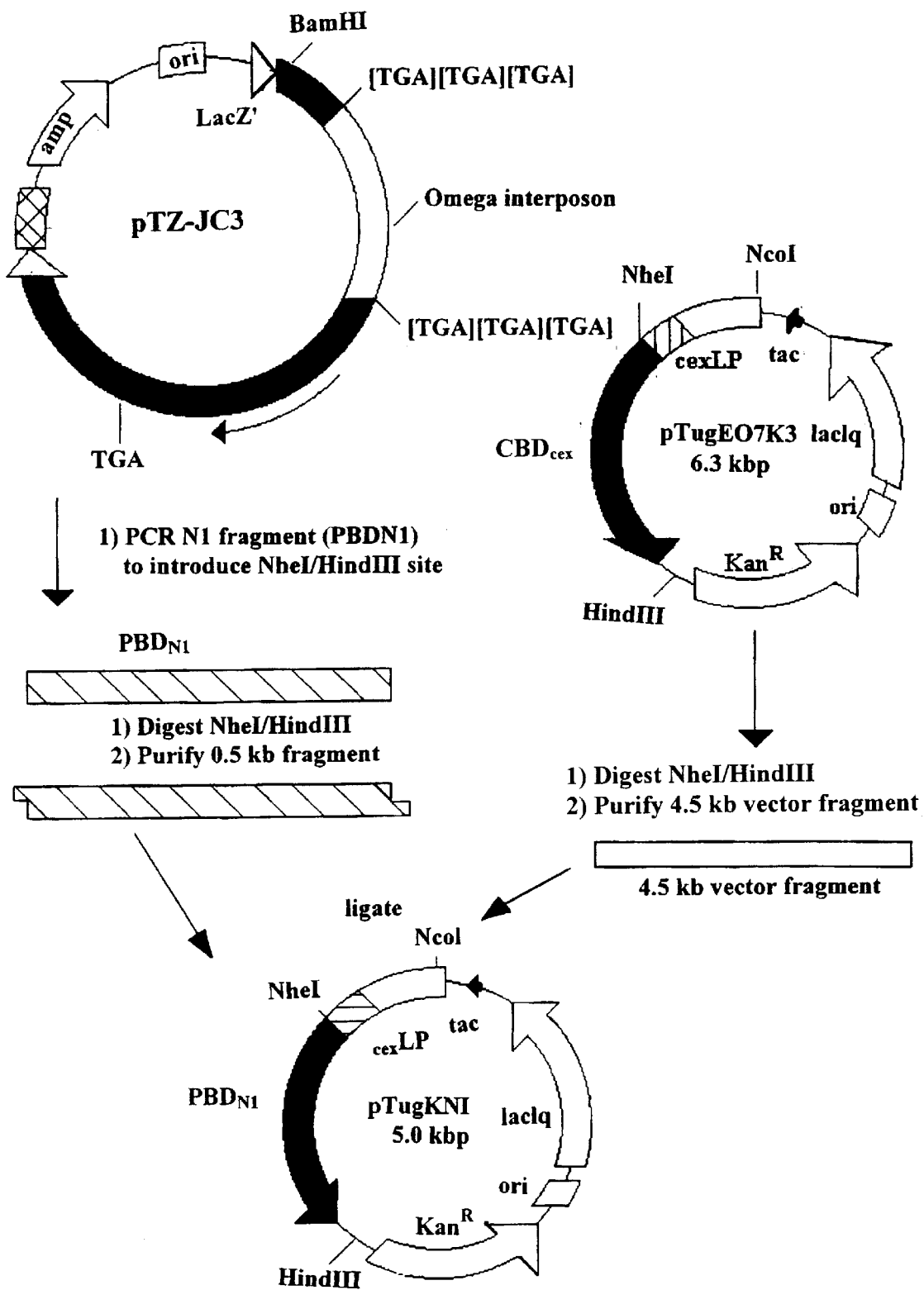
FIG. 6 shows the construction of pTugKN1. pTugEO7K3 was digested completely with NheI and HindIII to remove the 1.8 kbp fragment containing the $CBD_{Cex}$ and the 4.5 kbp fragment was isolated. PCR was used to introduce appropriate restriction sites at the 5' and 3' end of the gene fragment encoding $CBD_{N1}$. An NheI site (underlined), coinciding with the N-terminal end (ala-ser) of mature $CBD_{N1}$, was introduced as a silent mutation at the 5' end of cbdN1 using the oligonucleotide 5'-TTACCTCATAT GGCTAGCCCGATCGGGGAGGGAACG-3'. (SEQ ID NO:13) A HindIII site was introduced at the 3' end of cbdN1using the oligonucleotide 5'-AGAATGAATTC AAGCTTAGAGCTCGACCTCGGAGTC-3'(SEQ ID NO:14). A translational stop codon was also included in this primer. The polymerase reaction (PCR) mixture (50 µl total volume) contained 10–100 ng template DNA(pTZ-JC3) (Coutinho et al. *Mol. Microbiol.* (1992) 6:1243–1252), 25–50 pmole (300 ng) primers, 2 mM $MgCl_2$, 6% dimethyl sulfoxide, 0.2 mM 2'-deoxynucleotide 5'-triphosphates and 1 unit Taq DNA polymerase in 50 mM Tris-HCl buffer, pH 8.3. Twenty-eight successive cycles were performed as follows: denaturation at 94° C. for 15 sec, annealing at 57° C. for 1.4 min and primer extension at 72° C. for 1.5 min. The resulting cbdN1PCR fragment was digested completely with NheI and HindIII and the 0.5 kbp fragment was purified by precipitation. The 4.5 kbp and 0.5 kbp fragments were ligated to give pTugKN1.

A gene that encodes the SLF-CBD fusion protein was constructed as followvs. The coding sequence for the signal peptide from the cellulase Cex (O'Neill et al. (1986) *Gene* 44: 331–335) was introduced into the expression plasmid pTUG AS (FIGS. 3–5; Graham et al. (1995) *Gene* 158: 51–54) using site directed mutagenesis (Zoller and Smith (1982) *Nucleic Acids Res.* 10: 6487–6500). Coding sequences for a hexahistidine affinity tag followed by an NheI restriction site were introduced in frame at the 3' end of the Cex signal sequence coding region. The resulting fragment was subcloned into the non-expression plasmid pSL1180 (Pharmacia Ltd., Piscataway, N.J.) as an NcoI-Hind III fragment. A gene fragment that encodes the extracellular domain of murine steel factor (Anderson et al. (1990) *Cell* 63: 235–243; GenBank Accession No. M38436) was modified by polymerase chain reaction (PCR) (Kaufman and Evans (1990)BioTechniques 9: 304–306) to introduce an XbaI restriction site onto the 5' end of the gene fragment and StuI and Hind III sites onto the 3' end of the gene. This product was purified from an agarose gel using a QIAEX gel extraction kit (QIAGEN Ltd., Chatsworth, Calif.) and inserted downstream of the Cex signal peptide after cleavage of the Cex signal peptide-containing plasmid with NheI and HindIII. DNA from the original SLF gene was exchanged for the PCR product between two unique restriction sites which encompassed more than 90% of the gene, and the remaining vector junctions and flanking DNA were sequenced. The gene sequence encoding the cellulose binding domain from Cex, as well as its proline-threonine linker was then excised as a StuI-Hind III fragment from the plasmid pUC12-1.1 Cex (PTIS) (see U.S. Pat. No. 5,340,73 1) and inserted, in frame, downstream of the gene encoding the steel factor extracellular domain. The entire construct was then excised from pSL1180 as an NcoI-HindIII fragment and inserted into the high expression level plasmid pTug AS which had previously been modified to include kanamycin resistance by the insertion of a cassette. This plasmid was designated as pSLF/CBD 1.0.

Example 2

Expression and Purification of SLF-CBD

The plasmid pSLF/CBD 1.0 was transformed into *E. coli* JM101 (Yanisch-Perron et al. (1985) *Gene* 33: 103–119) for expression. Several colonies were scraped from a plate and used to inoculate a 5 ml test tube of Terrific Broth (Tartof and Hobbs, *Bethesda Res. Lab. Focus* 9: 12) containing 50 mg/ml kanamycin. This tube was incubated with shaking at 37° C. for four hours and then used to inoculate four flasks containing 500 ml of the same medium at 0.2% volume. These flasks were then incubated at 37° C. with shaking at 250 rpm until a cell culture optical density ($OD_{550}$) was reached. The cells were then induced by the addition of 0.1 mM IPTG and shifted to 30° C. with shaking at 100 rpm for a further eight hours. Cells were then harvested and the periplasmic proteins isolated by osmotic shock (Neu and Heppel (1965) *J. Biol. Chem.* 240: 3685–3692). Five mg of Avicel microcrystalline cellulose (FMC International, Cork, Ireland) was added to either 10 ml of culture supernatant or 1 ml of periplasmic extract and then removed by centrifugation. SDS-PAGE loading buffer was than added to the Avicel, which was then boiled for two minutes and loaded directly onto a gel for SDS-PAGE analysis (Laemmli, supra.) (FIG. 8A).

The periplasmic extract was buffered to a pH of 8.0 using 50 mM Tris-base (Boehringer-Mannheim, Indianapolis, Ind.) and concentrated to a volume of 2 ml by ultrafiltration through a 10 kDa pore size membrane. The sample was then purified using metal chelate affinity chromatography (MCAC) (Hochuli (1990) In *Genetic Engineering, Principles and Practice*, Vol. 12 (J. Setlow, Ed.), pp. 87–98, Plenum, N.Y.) using a 20 ml column packed with His-Bind resin (Novagen Inc., Madison, Wis., cat. no. 69670) with elution of the protein at between 100 mM and 200 mM immidazole. The peak fractions were pooled and the elution buffer was exchanged for phosphate buffered saline (PBS) and the sample concentrated again using ultra filtration. Purity of the final sample was evaluated by SDS-PAGE analysis and the protein concentration determined by absorbance at 280 nm wavelength (Scopes (1974) *Anal. Biochem.* 59: 277–282) and by the Bradford method (Bradford (1976) *Anal. Biochem.* 72: 248–254). SLF-CBD released into the culture supernatant was purified in the same way except for the addition of an initial precipitation step to reduce the volume of the sample. The supernatant was chilled to 0° C. and brought to 80% (w/v) of saturation ammonium sulfate while maintaining the pH at 6.05 (the predicted isoelectric point of the fusion protein) by the addition of 1N $NH_4OH$. The precipitated protein was collected by centrifugation at 10,000 g and resuspended in MCAC loading buffer. The protein was analyzed by both SDS-PAGE and by western blotting (Burnette (1981) *Anal. Biochem.* 112: 195–203) using either anti-murine steel factor polyclonal neutralizing antibodies (R&D systems, Minneapolis, Minn., cat. no. AB-455-NA) or anti-CBD antibodies.

In cultures of *E. coli* JM101 (Ong et al. (1993) *Biotechnol. Bioeng.* 42: 401–409) transformed with pTK-SLF-CBD, the SLF-CBD fusion protein was present in both the periplasm and the culture supernatant, and could be recovered from either source by binding to Avicel (FIG. 8A). Although SLF-CBD can be purified by affinity chromatography on Avicel, binding of the fusion protein to cellulose was strong and difficult to reverse. It was more convenient to use the amino terminal histidine affinity tag for purification.

Figure 8:
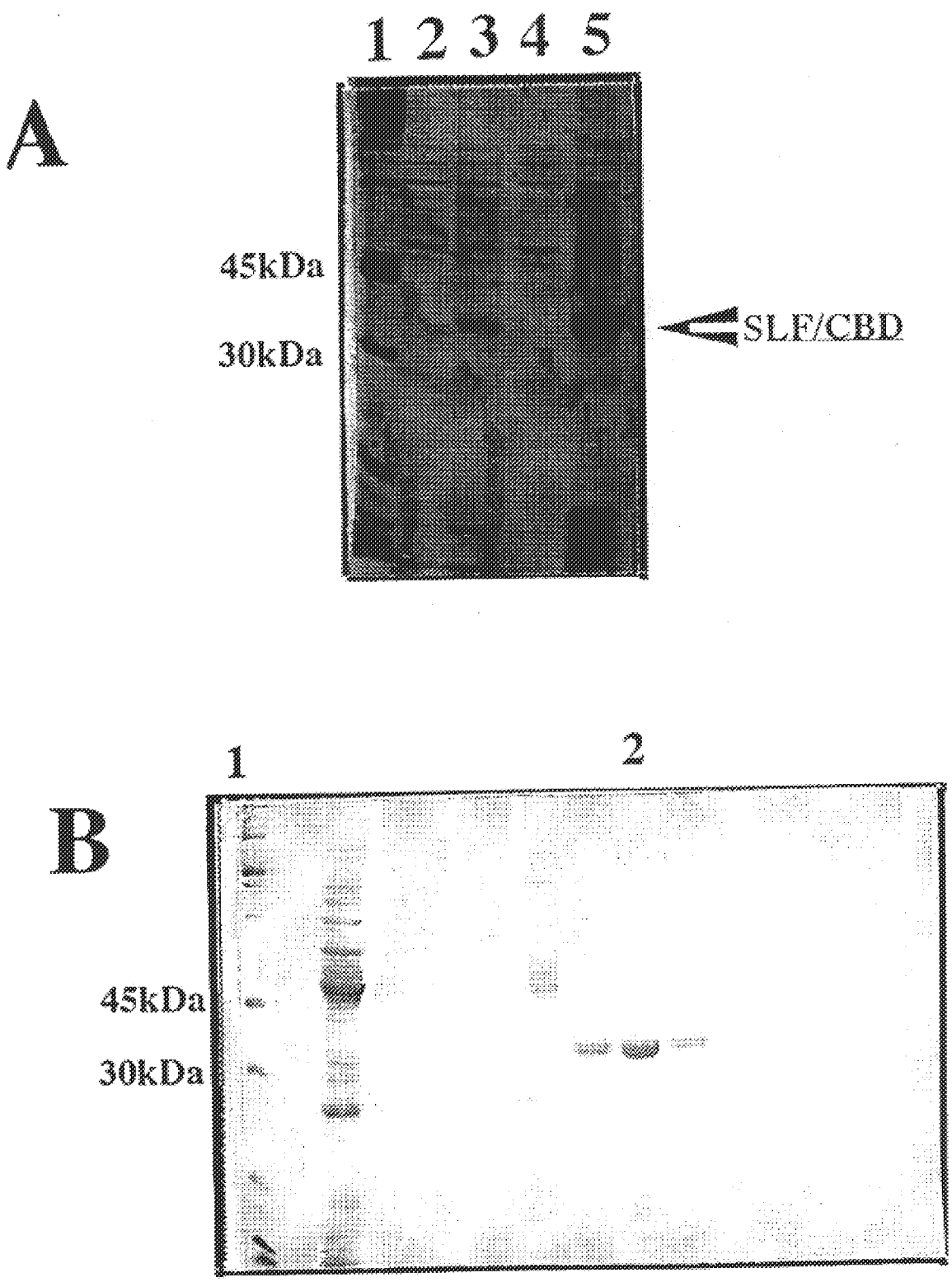
FIG. 8(A–B) shows purification of the SLF-CBD fusion protein. SLF-CBD can be purified using either of its two affinity tags.
Figure 9:
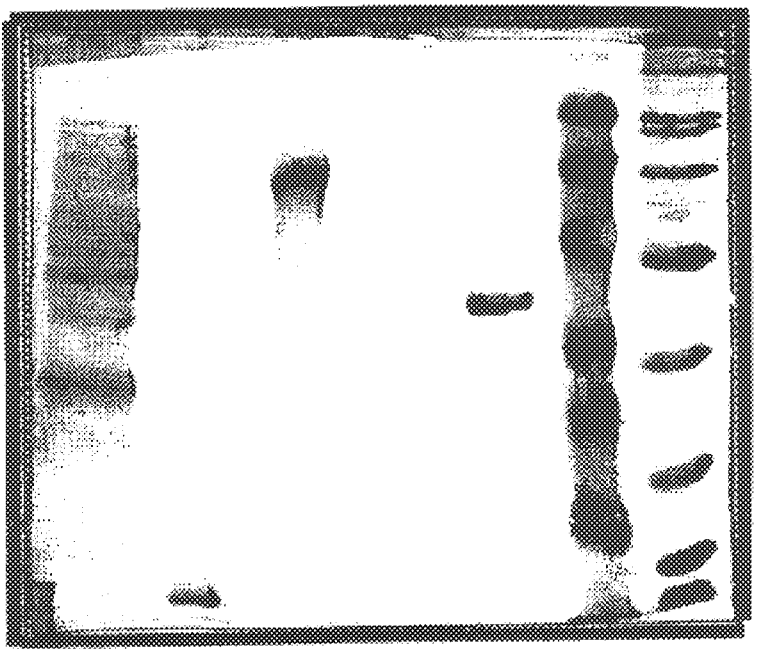
FIG. 9(A–C) shows SDS-PAGE and western blotting analysis of SLF-CBD. The identity of the purified fusion protein was confirmed by western blot analysis.
Figure 9:
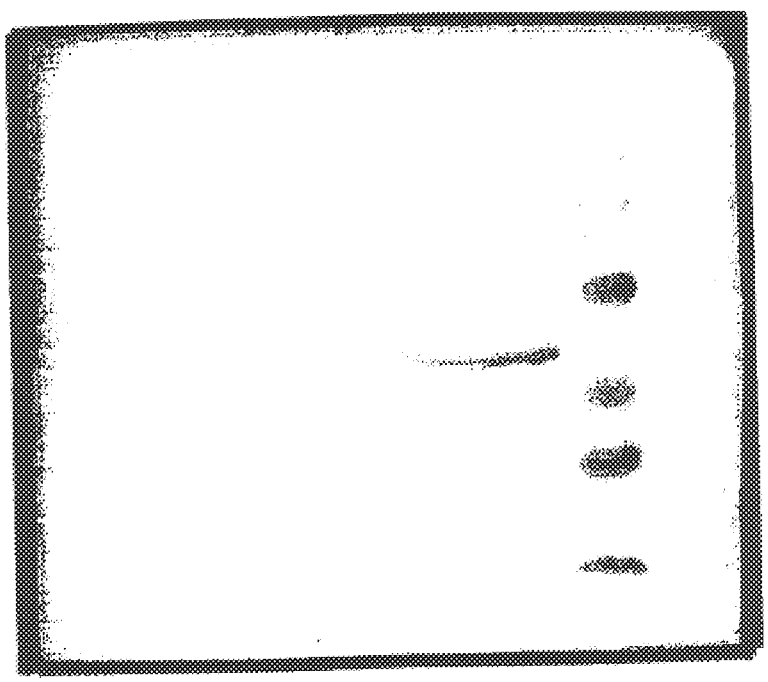
Figure 9:
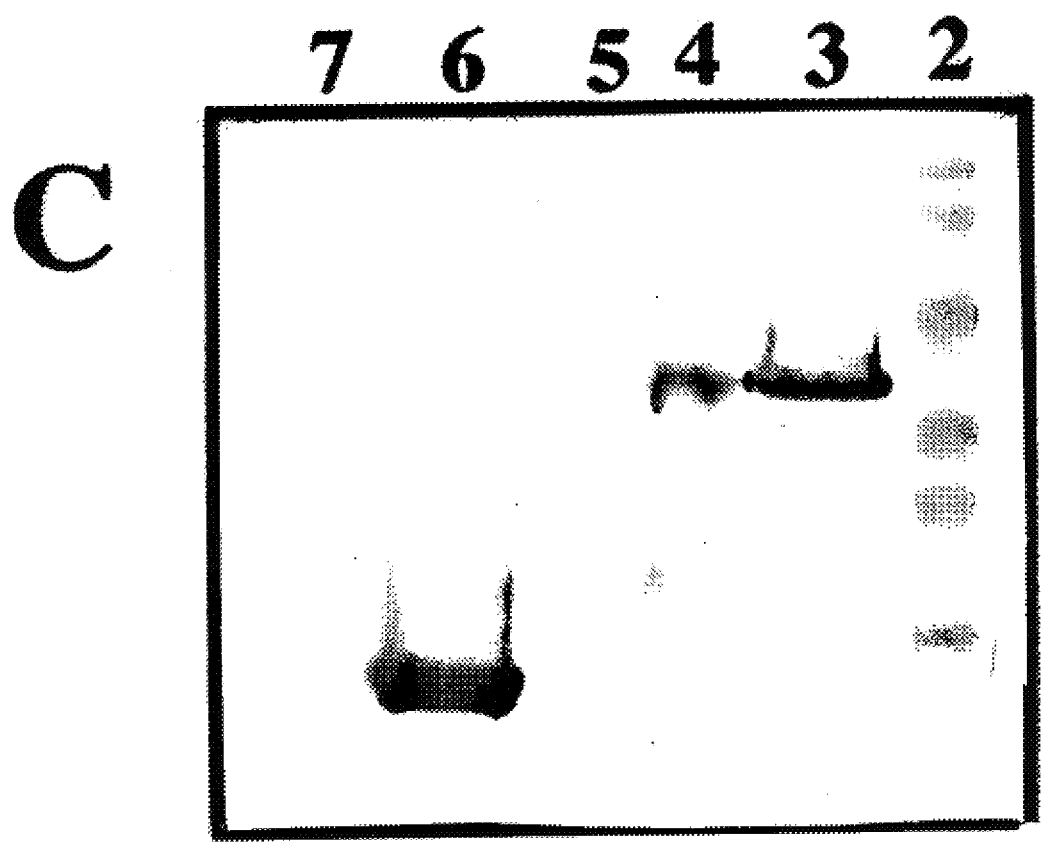

SLF-CBD from the periplasm was purified directly by high-performance liquid chromatography using a column packed with a nickel-Sepharose resin (FIG. 8B). The protein eluted as a single peak from this column at an immidazole concentration between 100 mM and 200 mM. SLF-CBD in the conditioned growth medium was purified in the same way following an initial volume reduction by ultrafiltration. A final yield of 0.7 mg/L of purified protein was obtained from the periplasm, and 1.8 mg/L from the supernatant. Amino-terminal sequence analysis of this protein confirmed that the signal peptide had been removed; and western blotting and SDS-PAGE analysis were carried out to confirm the identity of the protein (FIG. 9).

Example 3

Stimulation of Cell Proliferation using Immobilized SLF-CBD

Bacterial micro crystalline cellulose (BMCC) was prepared as described in Gilkes et al. (1992) *J. Biol. Chem.* 276: 6743–6749), sterilized, and resuspended at various concentrations in hybridoma serum free medium (H-SFM) (GIBCO BRL, Grand Island, N.Y., Cat. No. 12045-019).

Samples of purified SLF-CBD were diluted in H-SFM. Twenty $\mu$l protein test samples were placed into wells in sterile 96 well tissue culture plates (Costar corp. Cambridge, Mass., Cat. No. 3595). In experiments where BMCC was used, 50 $\mu$l of a BMCC suspension in H-SFM was added to each well, and in experiments where no BMCC was used 50 $\mu$l of H-SFM alone was added. SLF-CBD and BMCC were then incubated together for 12 hours at 37° C. with 5% $CO_2$ before the addition of 100 $\mu$l of B6SUtA cells (Greenberger et al. (1983) *Proc. Nat'l Acad. Sci. USA* 80: 2931–2935) which had been grown to one day past confluence and then resuspended in H-SFM at a concentration of $5 \times 10^{-5}$ cells/ml, to give a final assay volume of 170 $\mu$l. Cultures were then incubated for 48 hours at 37° C. and 5% $CO_2$, and cell proliferation was measured either by direct count in the hemocytometer, or by the MTT assay (Denizot and Lang (1986) *J. Immunol. Meth.* 89: 271–277). Recombinant steel factor (R&D systems, Minneapolis, Minn., Cat. No. 455-MC) was used as a positive control, while recombinant CBD was used as the negative control.

In experiments where Factor Xa was used, the assay was carried out as before except that 2.5 ng of Factor Xa (Boehringer-Mannheim, Indianapolis, Ind., Cat. No. 1179 888) were added to test wells during the 12 hour incubation step prior to the addition of the B6SUtA1 cells.

Statistical analysis of data was carried out with regression curve fitting in two iterations using non-linear regression analysis from the GraFit version 3.0 statistical analysis program (Erithacus Software Ltd., Staines, U.K.).

Figure 10A:
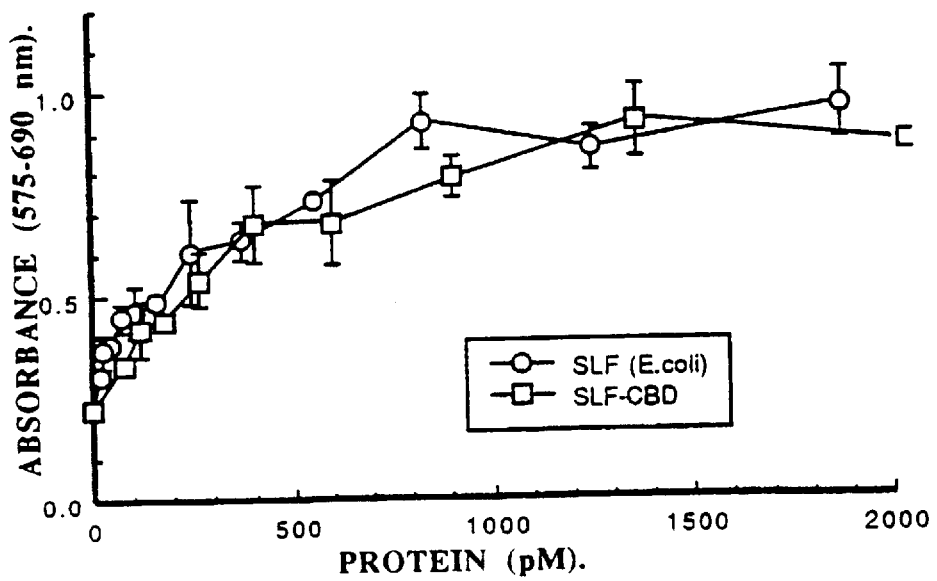
FIG. 10(A–B) shows activity and neutralization of activity of proteins in solution. The proliferative activities of the fusion protein and the control protein were analyzed (MTT assay) in the absence of an immobilization matrix (FIG. 10A). The activity of 0.6 nM SLF-CBD was neutralized by anti-SLF neutralizing polyclonal antibodies (FIG. 10B). Baseline MTT activity of 0.2 absorbance units was subtracted.
Figure 10B:
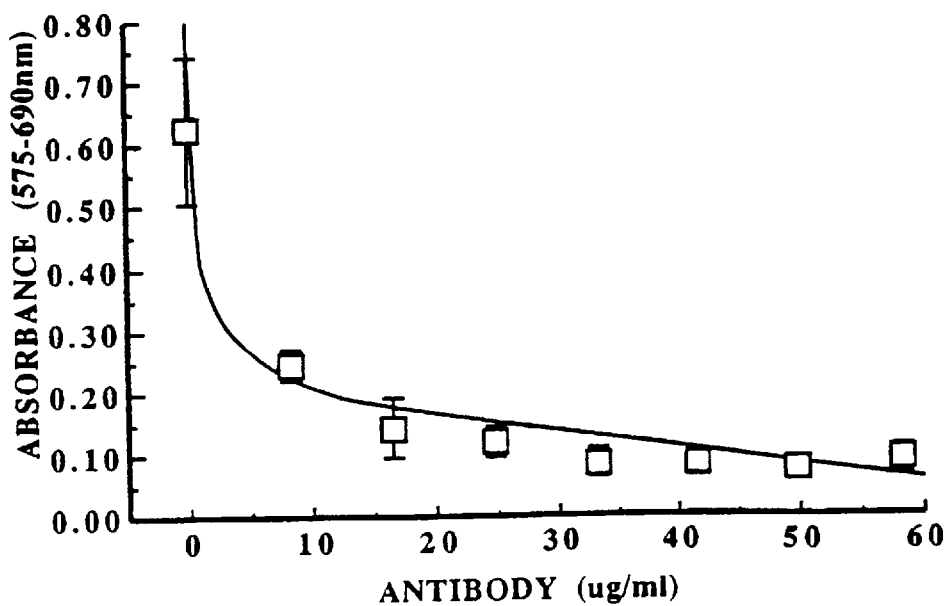

The activity of the non-immobilized SLF-CBD fusion protein was compared to that of the control SLF without an affinity tag (FIG. 10A) using the MTT test and the SLF dependent bone marrow cell line B6SUtA1. The activities of the proteins were similar and within the expected range based on the specific activity of the control SLF. The activity of SLF-CBD was neutralized by anti-SLF neutralizing polyclonal antibodies (FIG. 10B). CBD alone did not stimulate the proliferation of B6SUtA1 cells (data not shown).

Biological activity in the presence of BMCC

Bacterial microcrystalline cellulose (BMCC) is a highly crystalline form of cellulose produced by *Acetobacter xylinum* (ATCC 23769). After preparation, BMCC forms a high surface area fine suspension which does not sediment rapidly, and is therefore easily diluted to obtain the desired final concentration.

Figure 11:
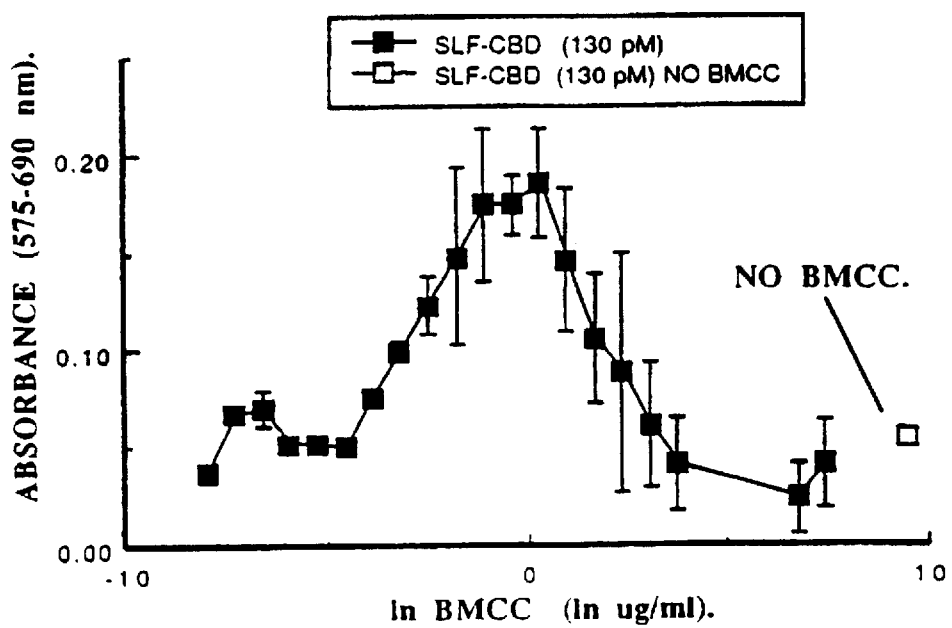
FIG. 11 shows activity of SLF-CBD as a function of BMCC concentration: the BMCC concentration was varied with SLF/CBD concentration held constant at 130 pM (FIG. 11).

A dilution series of BMCC was prepared, covering a wide range of BMCC concentrations, and each of these concentrations was tested using a constant amount of SLF-CBD. For SLF-CBD at 130 pM, maximum activity was observed with a BMCC concentration of about 1 $\mu$g/ml (FIG. 11). When the SLF-CBD concentration was increased to 1500 pM, the activity increased and the peak shifted to a higher BMCC concentration (FIG. 11), indicating that the concentrations of both SLF-CBD and BMCC affect the proliferating response of B6SUtA1 cells in this system and suggesting the need for an optimal surface concentration of SLF-CBD on the BMCC.

Influence of SLF-CBD bound to a fixed amount of BMCC

Figure 12:
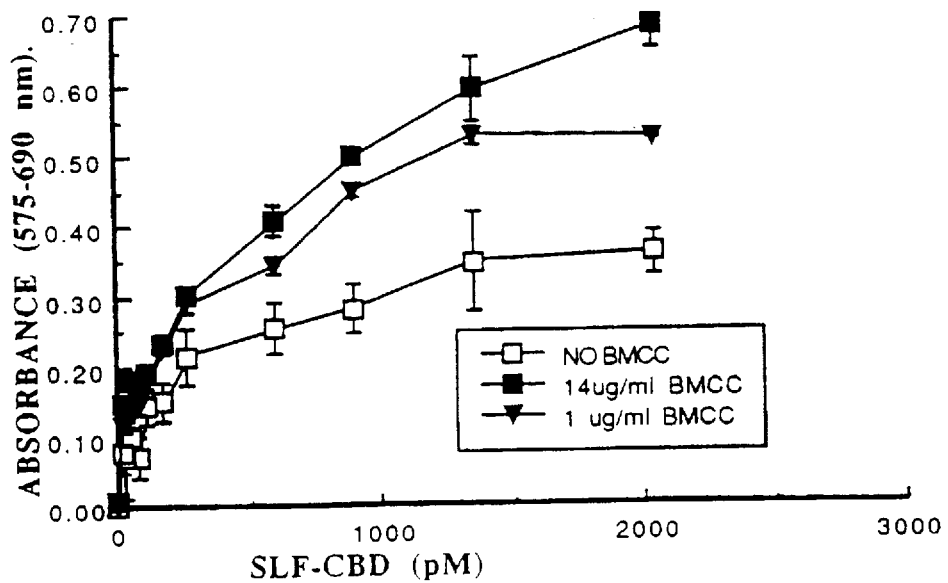
FIG. 12 shows the activity of SLF-CBD as a function of BMCC concentration. The concentration of SLF-CBD added to each well was varied while the BMCC concentration was held constant at the concentrations indicated.

The presence of BMCC had no effect on the activity generated by the non-affinity tagged control SLF. Using a fixed BMCC concentration of 1 $\mu$g/ml or 14 $\mu$g/ml a converse series of experiments was carried out in which the amount of BMCC surface available was held constant and the SLF-CBD concentration was varied. SLF-CBD was clearly more active in the presence of BMCC than in the absence of BMCC, with both an increase in total cell proliferation and a decrease in the value of its $ED_{50}$ (the protein concentration required to produce a half maximal response) being observed (FIG. 12).

Figure 13A:
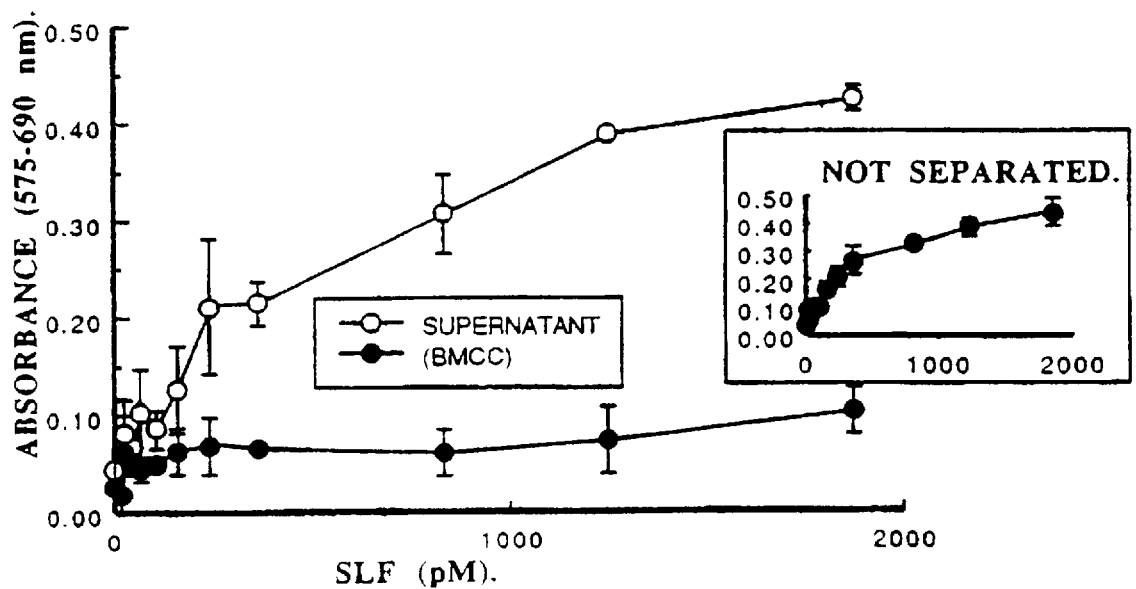
FIG. 13 (A–C) shows separation of protein bound to the matrix from protein not bound to the matrix. Various amounts of SLF-CBD were bound to 1 µg/ml of BMCC. The matrix was then removed from solution by centrifugation and resuspended in fresh medium. The activities of the original medium and the resuspended BMCC were then assayed for activity to determine how much of the protein bound to the matrix. With control SLF, most of the activity was in the supernatant (FIG. 13A), with SLF-CBD the bulk of the activity was associated with the BMCC (FIG. 13B). When the cellulose affinity tag of SLF/CBD was cleaved from the SLF by Factor Xa the activity was no longer associated with the BMCC (FIG. 13C).
Figure 13B:
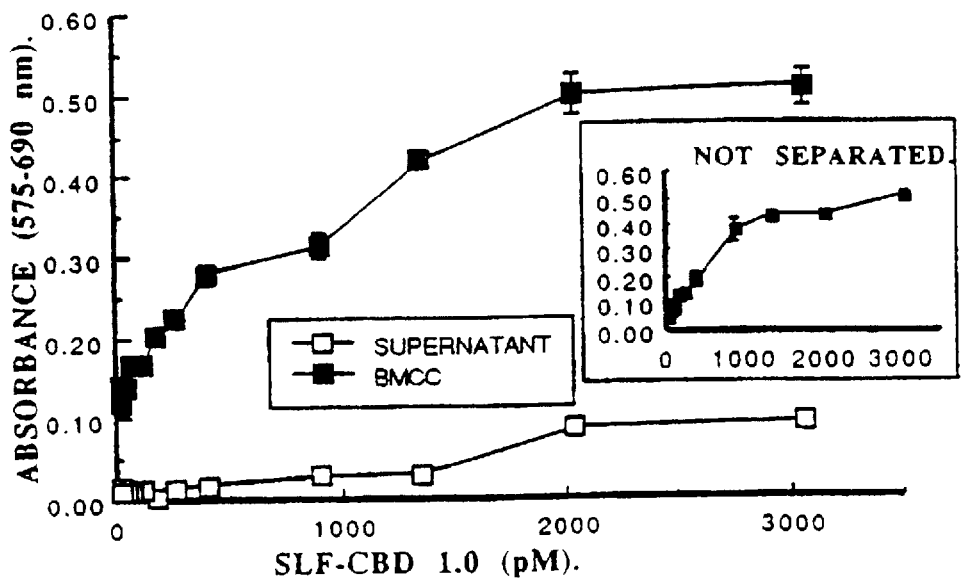
Figure 13C:
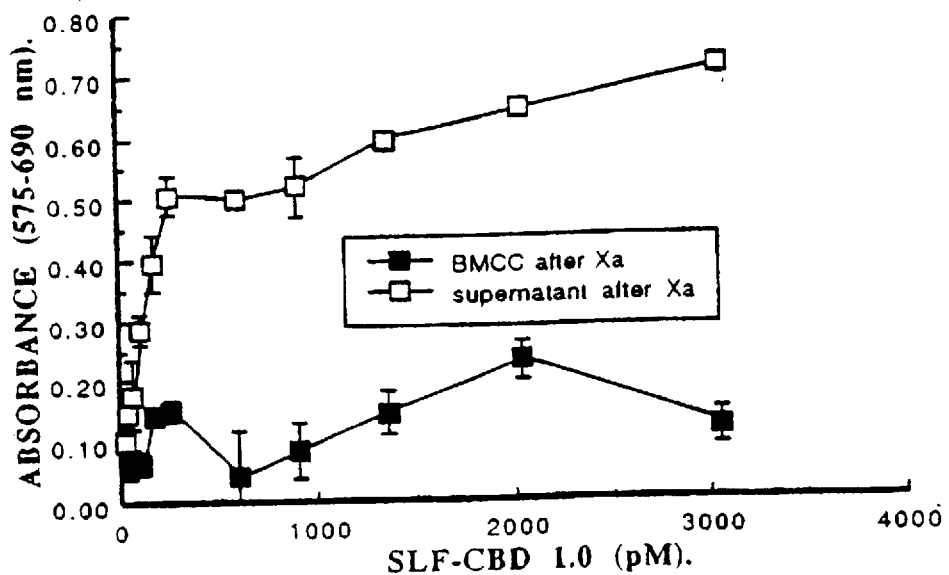

To determine the distribution of SLF-CBD, the activities of free and bound SLF-CBD were tested separately (FIGS. 13A–13C). For the non-tagged SLF control most of the activity was associated with the supematant (FIG. 13A). The reverse was seen for SLF-CBD, where most of the activity was associated with the BMCC particles (FIG. 13B). This test also demonstrates that the binding capacity of 1 μg/ml of BMCC was not exceeded even by the highest concentrations of SLF-CBD used.

SLF-CBD bound to BMCC could be released by adding Factor Xa to cleave the fusion protein at the Factor Xa site introduced between the SLF and the CBD. Following this treatment, the bulk of the activity was found in the supernatant (FIG. 13C).

These results indicate that, although the maximum cell density generated by the fusion protein in soluble form was not quite as great as that generated by the control protein, the $ED_{50}$ values were identical. When the SLF-CBD fusion protein was immobilized on cellulose, however, it was significantly more potent than SLF-CBD in solution, generating a significantly higher maximum proliferative response and exhibiting a higher specific activity. This effect was not observed for the control protein which lacked an affinity tag and could not be immobilized.

It is noteworthy that the enhanced proliferative activity of immobilized SLF-CBD was dependent on the concentration of BMCC. At a fixed SLF-CBD concentration, the proliferative response increased as the BMCC concentration increased to a maximum value, and then decreased at higher BMCC concentrations (FIG. 11). Increasing the concentration of SLF-CBD in this experiment shifted the maximum to higher BMCC concentrations. Presumably at very low BMCC concentrations the matrix surface area is limiting while at very high BMCC concentrations it is the steel factor which is limiting, with a decrease in the density of SLF-CBD on the BMCC surface. Increasing the SLF-CBD concentration counteracts this effect, providing a higher surface concentration of SLF-CBD. The specific surface concentration of steel factor molecules has a dramatic effect on the stimulation of B6SUtA cells. For a SLF-CBD concentration of 130 pM, the addition of BMCC produced a maximum at 1 μg/ml (FIG. 11), whereas at a SLF-CBD concentration of 1500 pM the maximum shifted 44 μg/ml and the level of stimulation increased. Clearly the level of stimulation in these cultures is influenced both by the surface concentration of SLF and the amount of cellulose surface. Based on the dimensions of the BMCC particles reported by Gilkes et al, supra., the available surface area is 1.22 $Cm^2$ per μg of BMCC. For both levels of BMCC, the density of SLF-CBD on the surface would be about $4 \times 10^{10}$ molecules/$cm^2$. Assuming a cell diameter of 10 mm and 35,000 c-kit receptors per cell as is the case for MO7e cells (Turner et al. (1995) *Blood* 85: 2052–2058) the receptor density on the cell surface would be $1.1 \times 10^{10}$ receptors per $cm^2$. Based on these estimates, the effect of the addition of an immobilization matrix was maximal when the relative density of SLF-CBD on was four times the density of the c-kit receptors on the cell membrane.

We also analyzed the effect of increasing SLF-CBD with surface area maintained constant at 1 μg/ml (1.22 $cm^2$/ml). In this case, maximum stimulatory activity was observed when the SLF-CBD concentration was about 2000 pM, equivalent to a SLF-CBD density of $7 \times 10^{11}$ molecules per $cm^2$. This number is about 60 times the estimate-we have used for receptor density on the cell surface. Overall, these results suggest that there is a threshold for stimulation when the density of SLF is about four times of the receptor density on the cell surface. The stimulatory activity increases with the SLF concentration reaching its maximum when the SLF surface density is 30–60 fold higher than the receptor density on the cell membrane.

Example 4

Persistence of SLF-CBD Biological Activity When Immobilized on Regenerated Cellulose Surfaces A 1% (w/v) solution of cellulose acetate was prepared by adding one gram of cellulose acetate (Kodak Inc.) to 99 ml of acetic acid. One hundred μl of this solution was added to each well of the standard 96 well tissue culture plates used above, and the acetic acid allowed to evaporate. One hundred μl of 50 mM NaOH was then added to each well and left for 20 minutes to regenerate a cellulose surface. The NaOH was then poured out, and the wells rinsed three times with PBS. Three hundred μl of 70% (v/v) ethanol was then added to each well, the plate lid replaced, and the ethanol allowed to evaporate as a sterilization step.

Activity tests were carried out as previously described except that a cellulose acetate derived surface was used to immobilize SLF/CBD instead of BMCC. Twenty μl protein test samples were put into cellulose coated wells. Fifty μl of H-SFM was then added to the wells, and incubated 12 h prior to the addition of 100 ml of B6SUtA cells for the standard final volume of 170 μl. Activity was measured after 48 h of culture using the M1I test with data points collected in quadruplicate. A control group of cells was added to each of four wells in a cellulose coated plate and to each of four wells in a non-coated plate. These cells were then counted after a 48 hour incubation to determine if the surface exhibited any toxicity.

Cellulose coated plates were loaded with SLF-CBD as described above, and B6SUtA cells were added as before. After the standard 48 hour incubation period, the cells were moved to a separate plate to determine the activity by the MTT test while the wells of old plate were washed with 150 μl of warm H-SFM. After washing, 170 μl of fresh B6SUtA test cells were added to each well and the 48 hour incubation period was repeated. The entire procedure repeated so that the surface was used for cell culture a total of three times. In another experiment, SLF-CBD was bound to a cellulose coated plate and the H-SFM supernatant from these wells was exchanged every 48 hours without the addition of cells. After the third exchange of supernatant, cells were added to the SLF/CBD coated surface and the MTT assay was performed after the 48 h incubation.

Non-tagged SLF was used as a control. In one set of control experiments, SLF was added to cellulose coated tissue culture wells as before, the surface was seeded with fresh cells three times, and the proliferation measured. In another series of control experiments the SLF-CBD protein was added to tissue culture plates not coated with cellulose. These surfaces were seeded with cells three times and the activity measured.

Figure 14A:
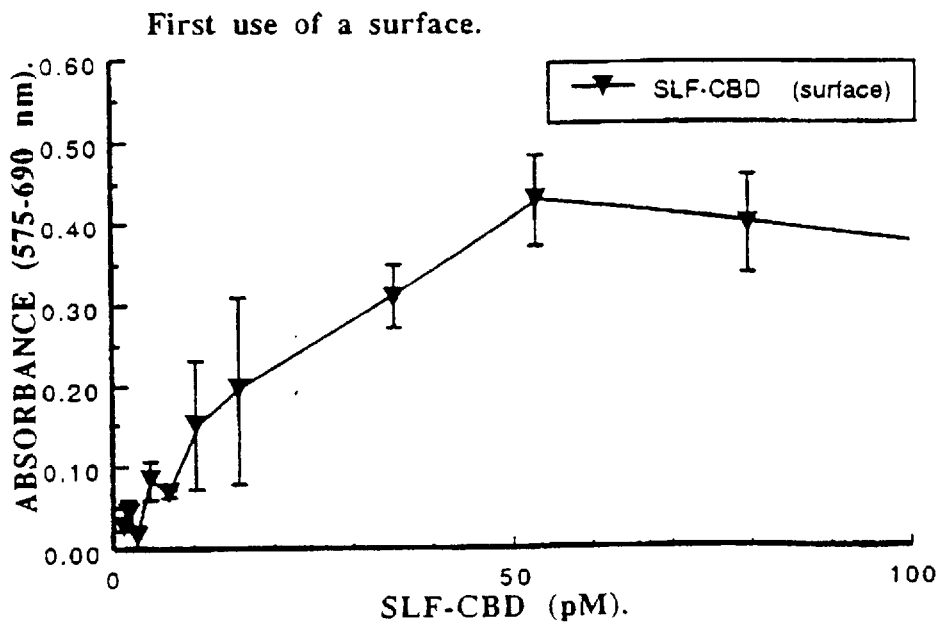
FIG. 14(A–B) shows the activity of SLF-CBD bound to regenerated cellulose. SLF-CBD was bound to a cellulose coated microtiter plate and the supernatant was removed from each well and replaced with medium. Cells were then added to the plate and the activity remaining bound in each well was assayed as before (FIG. 14A). SLF-CBD was bound to cellulose coated microtiter wells as above and the wells were used for three consecutive rounds of cell culture. MTT assays of cultures following the third use indicate no loss in proliferative activity (FIG. 14B). A control plate was treated identically except that cells were not added until the third cycle.
Figure 14B:
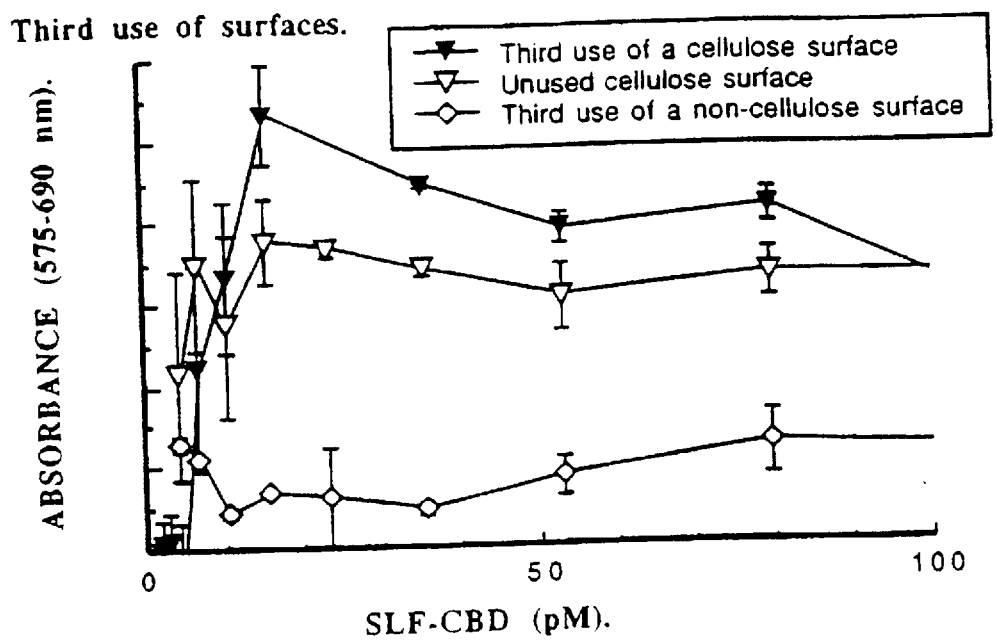

SLF-CBD also bound to a reconstituted cellulose surface applied to the bottom of a microtiter plate. This system facilitated the separation of the cells from the cellulose surface so that the surfaces could be reused for several consecutive rounds of cell culture. Analysis of the activity bound to the plate or remaining in the supernatant indicated that essentially all of the SLF-CBD was bound (FIG. 14A). Repeated use of the same surface showed no loss of proliferative activity during the three rounds of cell growth (FIG. 14B). Similar results were obtained from a separate plate, identically treated except that cells were not added until the third cycle (FIG. 14B).

It is apparent that the immobilized steel is not being consumed by the cells, since SLF-CBD coated plates could be used repeatedly. In contrast, soluble steel factor is internalized and consumed by cells which is likely a homeostatic mechanism to regulate the duration of stimulation (Miyazawa et al. (1995) *Blood* 85: 641–649). Immobilization of SLF would then prevent down regulation by consumption of the growth factor.

Example 5

Isolation of $CBD_{N1}$

*Escherichia coli* JM 101 (SupE, thi-1, Δ(tac-proAB), (F'traD36, proAB, taclqZΔM15) (Yanish-Perron et al. (1985) *Gene* 33:103–119) was used as the host strain for maintenance of the plasmids and for production of recombinant protein. Cultures were grown at 30° C. in liquid tryptone-yeast extract-phosphate medium (TYP) or on Lunia broth (LB agar, supplemented with kanamycin (100 g/ml).

Figure 7:
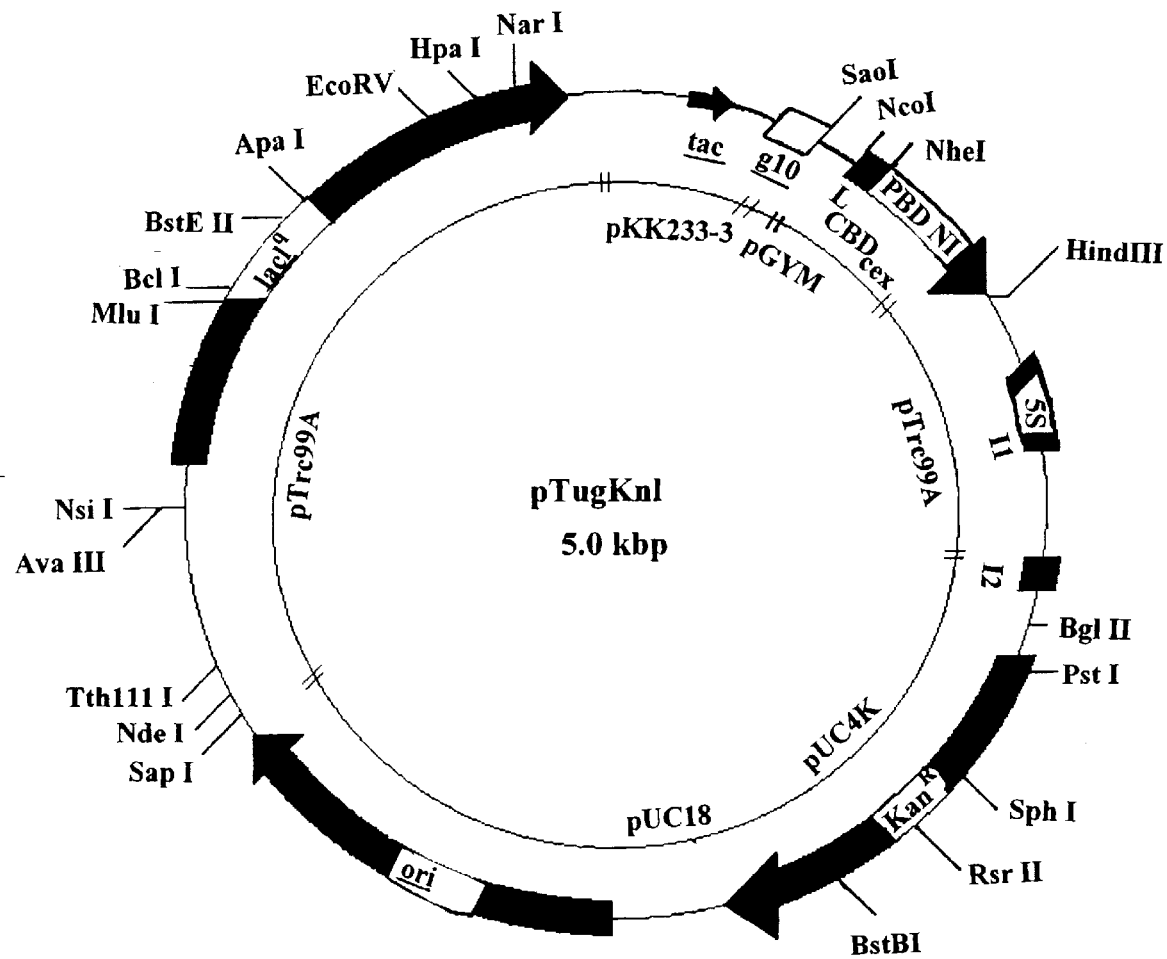
FIG. 7 shows the pTugKN1 vector. The pTugKN1 vector is derived from the pTugA vectors by replacing the selective marker for ampicillin resistance (β-lactamase encoding sequence) with the selective marker for kanamycin resistance. The sequence encoding the leader peptide of the endoglucanase A (CenA) of *C. fimi* was replaced with the encoding sequence for leader peptide of the exoglucanase (Cex) from *C. fimi* (Ong et al. *Biotechnol. Bioeng.* (1993) 42:401–409).
Figure 15:
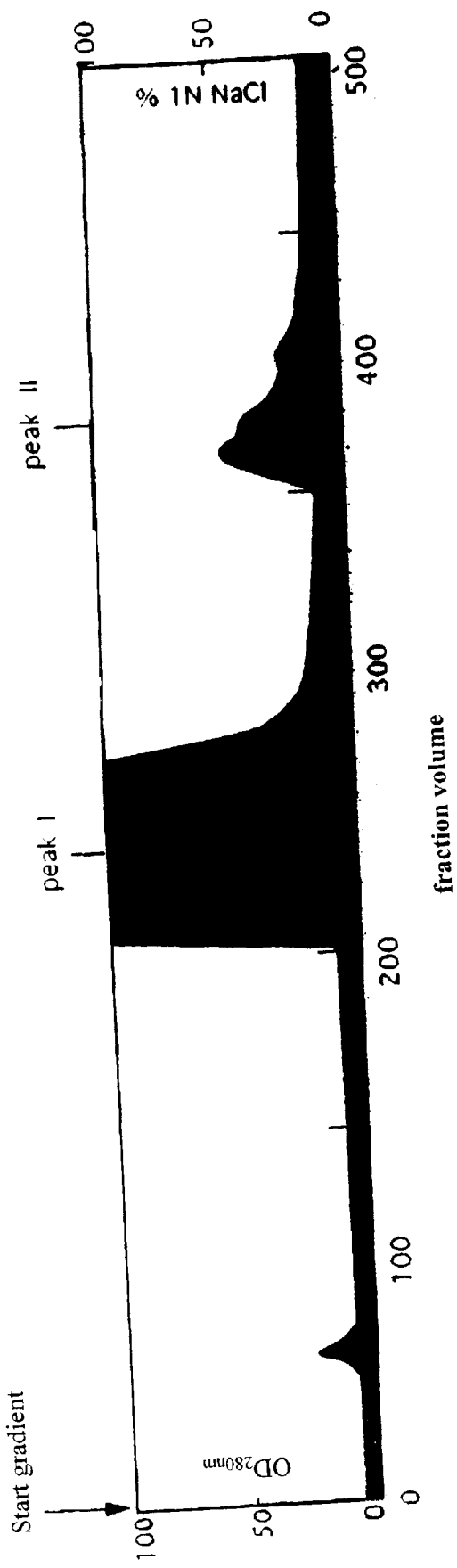
FIG. 15 shows the results of anion exchange chromatography of $PBD_{N1}$. Partially purified $PBD_{N1}$ (150 mg in 200 ml) was loaded (1 ml/min) onto an anion exchange column (MonoQ) equilibrated in 20 mM potassium phosphate buffer, pH 6.0. After washing the column with 200 ml buffer, pH 6.0, bound protein was recovered (8 ml fractions) using a salt gradient (600 ml, 0 to 1M NaCl in 20 mM potassium phosphate buffer, pH 6.0). $PBD_{N1}$ was recovered from the column in 300 mM salt (peak 1). Contaminating proteins bound more tightly and were removed in higher salt (peak 2).
Figure 16:
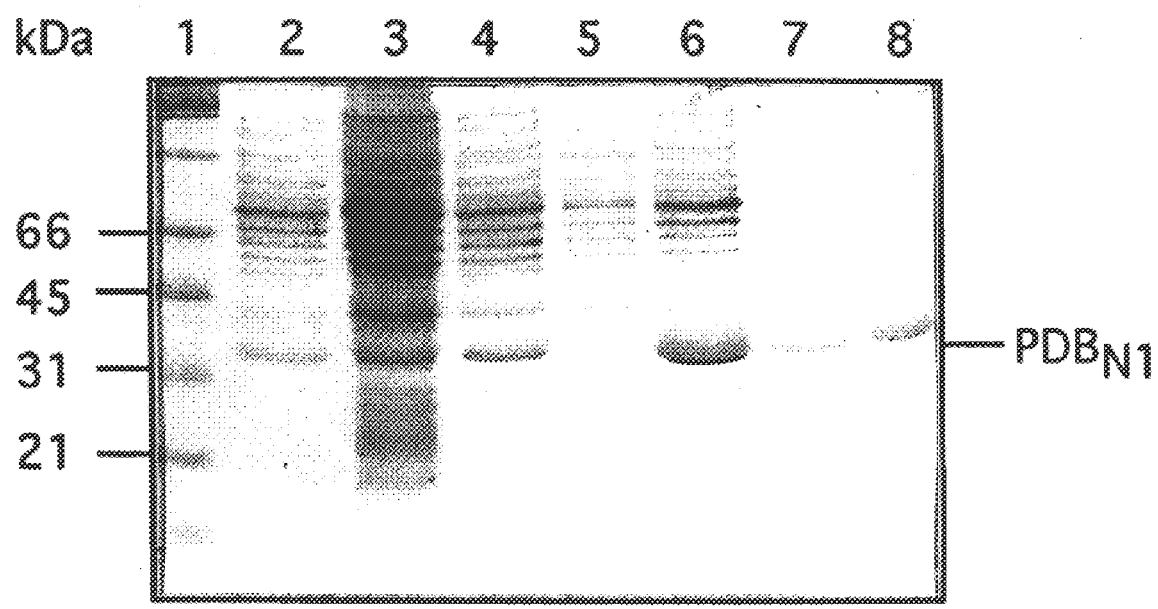
FIG. 16 shows SDS-PAGE analysis of $PBD_{N1}$ during purification from culture supernatants. Culture supernatants from JM101 harboring pTugKN1 (induced) (lane 2), whole culture suspension (cells and broth) (lane 3), Avicel fraction after binding of proteins in culture supernatants (lane 4), flow through fraction after binding supernatants to Avicel (lane 5), fraction eluted with $H_2O$ from Avicel (lane 6) and $PBD_{N1}$ after MonoQ purification (lanes 7 and 8) were analyzed on a gel containing 12.5% acrylamide. Molecular mass standards (lane 1) are as indicated.

Overnight cultures of *E. coli* strain JM11, harboring pTugKN1 (see FIG. 7), were diluted 500-fold in TYP supplemented with 100 μg kanamycin/ml, and grown at 30° C. to an optical density of 2.0–3.0. $PBD_{N1}$ production was induced by the addition of isopropyl-1-thio-β-D-galactopyranoside (IPTG) to a final concentration of 0.1 mM and the bacteria were incubated for a further 18 h at 30° C. Culture supernatants was clarified by centrifugation (4° C.) for 10 min at 13000×g and cells were discarded. Affinity chromatography on cellulose was used to purify $PBD_{N1}$, as follows. The clarified culture supernatant was incubated (4° C.) with microcrystalline cellulose (Avicel) (50 mg. L-1) with occasional stirring to allow $PBD_{N1}$ to bind. The cellulose suspension was filtered on a Buichner funnel through a glass filter (Whatman GF/A) and briefly washed with 1M NaCl in 50 mM potassium phosphate, pH 7.0. Bound $PBD_{N1}$ was desorbed with water and concentrated by ultra filtration. Partially purified $PBD_{N1}$ was then loaded onto an anion-exchange column (MonoQ) equilibrated in 20 mM potassium phosphate-buffer, pH 6.0, operated at a flow rate of 1 ml./min. Proteins bound tightly to the column and were removed with a salt gradient (0-IN NaCl, pH 6.0) (see FIG. 15). $PBD_{N1}$ was recovered in 300 mM salt (peak 1, FIG. 15). Contaminating proteins bound more tightly and were removed in higher salt (peak 2, FIG. 15). FIG. 16 shows an SDS-PAGE analysis of $PBD_{N1}$ during purification.

Example 6

Figure 17:
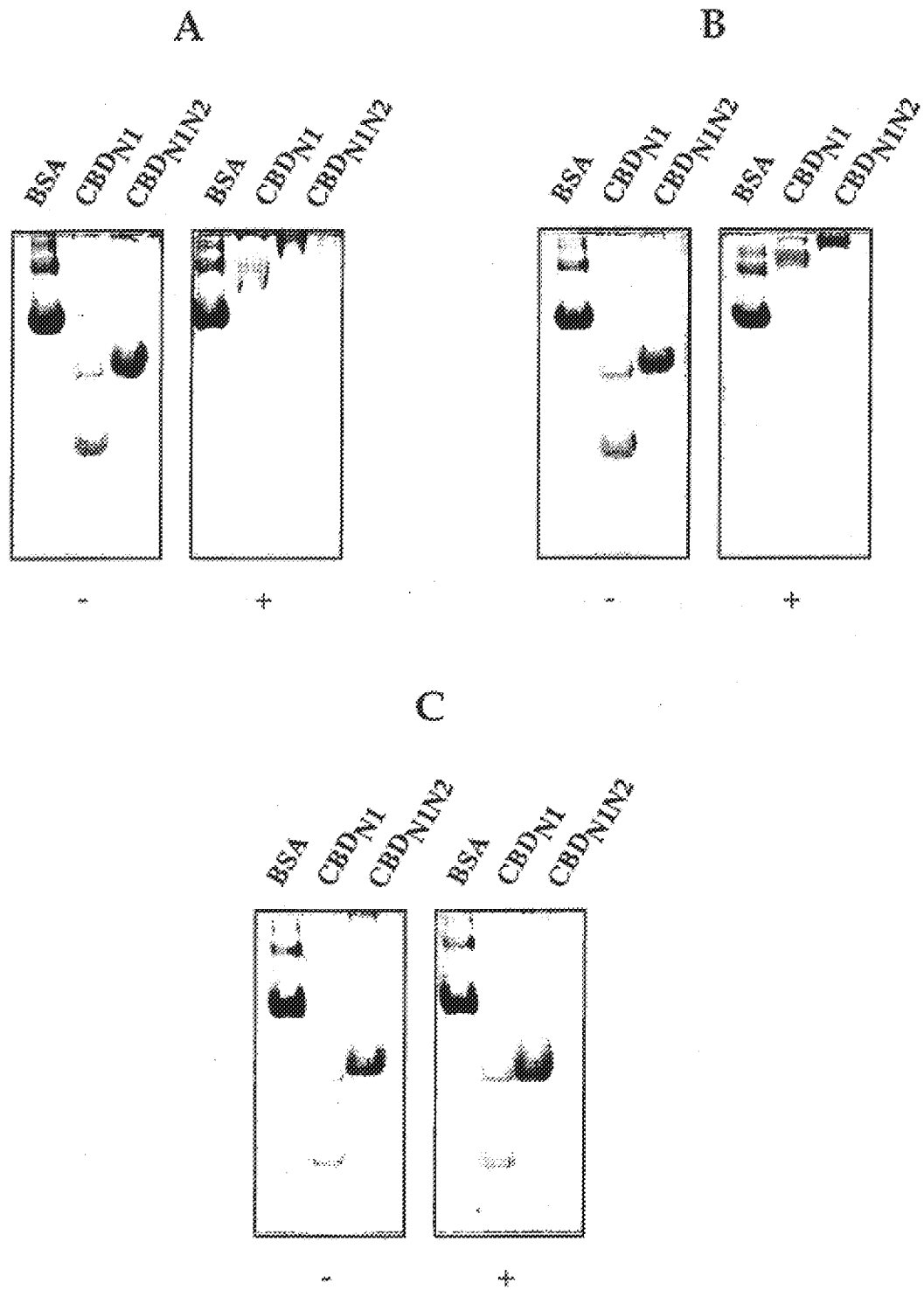
FIG. 17(A–C) shows affinity electrophoresis gels for analysis of PBPs ($PBD_{N1}$ and $PBD_{N1N2}$). Binding of purified bovine serum albumin (BSA) (lane 1), $PBD_{N1}$ (lane 2) and $PBD_{N1N2}$ (lane 3) to soluble oligosaccharides was analyzed in native gels containing 13% acrylamide. Retardation in the gels in the presence (+) of polysaccharide (0.1% w/v hydroxyethyl cellulose (HEC) or barley glucan) relative to their migration in gels in the absence (–) of the oligosaccharides is indicative of binding. Xylan is used as an non-binding polysaccharide. 5 µg of each protein were loaded on each gel.

Analysis of HEC, Barley-β-glucan and Xylan Binding to $CBD_{N1}$ and $CBD_{N1N2}$ by Affinity Electrophoresis Affinity electrophoresis (Mimura et al. (1992) *J. Chromatography* 597:345–350) was used to identify and evaluate the binding of $CBD_{N1}$ and $CBD_{N1N2}$ to soluble polysaccharides with a DP≧15 such as HEC and barley β-glucan. The original continuous disc electrophoresis method was replaced with a discontinuous method. Two native gels, one containing the polysaccharide (0.1% w/v) and one without the ligand, were prepared next to one another in the same plate of a BioRad electrophoresis system. This guaranties that analysis in the presence or absence of soluble polysaccharide is conducted essentially under the same conditions and that the observed effects (retardation in the presence of binding glucan) are not the result of an anomalous electrophoretic migration. BSA was used as a negative control in each gel. Proteins (5 mg each) were loaded onto the gels. Electrophoresis was conducted at 4° C. under native conditions at pH 8.2–8.8 for 2 to 3 h. $CBD_{N1}$ and $CBD_{N1N2}$ interact strongly with HEC and barley β-glucan and as a result, their migration in the gels containing these oligosaccharides (+) is severely retarded as compared to the migration in gels in absence (–) of a β-glucan (see FIGS. 17A and 17B). $CBD_{N1}$ and $CBD_{N1N2}$ do not exhibit any affinity for xylan and no retardation of migration in the gels is observed in the presence of this glycan as compared to migration in its absence (see FIG. 17C). N1 and N1N2 refer to $CBD_{N1}$ and $CBD_{N1N2}$, respectively.

Example 7

Figure 18:
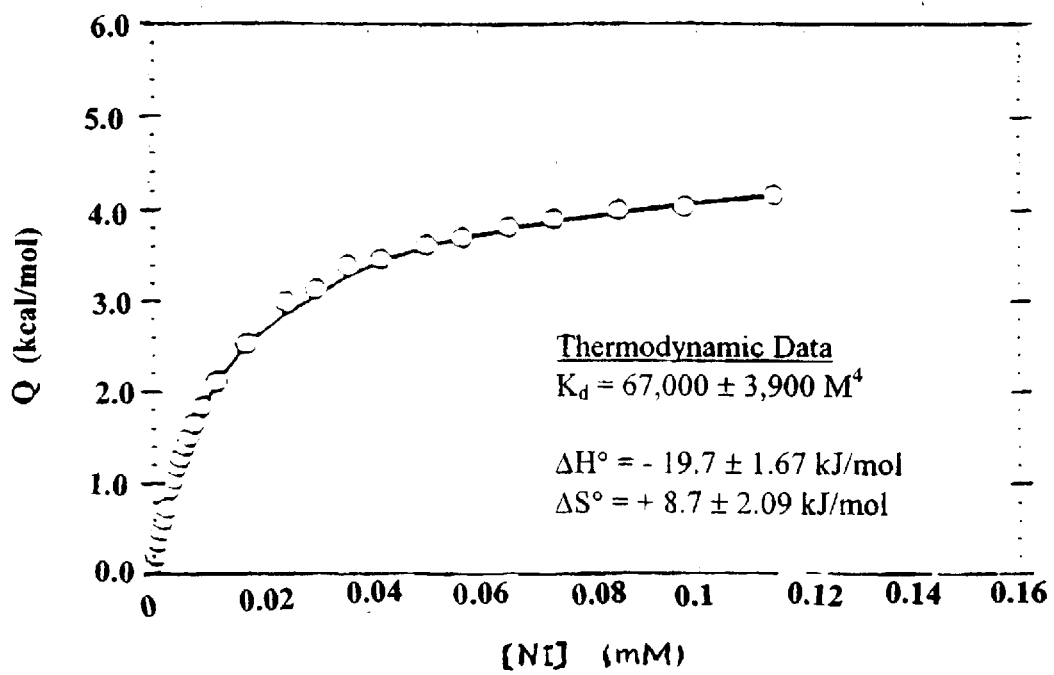
FIG. 18 shows isothermal titration microcalorimetry data for binding of hydroxyethyl cellulose to $CBD_{N1}$ in 50 mM phosphate buffer solution at pH 7 and 35° C.

Isothermal Titration Microcalorimetry Determination of Oligosaccharide Binding Constants for $CBD_{N1}$ and $CBD_{N1}$-Fusion Proteins Microcalorimetry was used to measure binding thermodynamics for $CBD_{N1}$ to a wide range of water-soluble oligosaccharides with the aim of identifying a set of suitable ligands for the affinity partition system. These data are shown in Table 7 below. FIG. 18 shows reversible binding-isotherm data measured with a Calorimetry Sciences Corp. model 4200 ITC for $CBD_{N1}$ binding to hydroxyethyl cellulose (HEC) in 50-mM PBS at 35° C. and pH 7. $CBD_{N1}$ strongly binds HEC with an equilibrium binding constant in the range of weak antibody-antigen interactions. Barley β-glucan binding to $CBD_{N1}$ is even stronger at these conditions (Ka=85,500 M-1). For both oligosaccharides, $CBD_{N1}$binding is as tight or even tighter than nearly all PEG-based affinity ligands (e.g., Cibacron blue-PEG, Procion red-PEG, dinitrophenyl-PEG, diacetic acid-PEG) currently in use in affinity partition systems. This relatively high binding affinity, combined with the potential for a single oligosaccharide chain to bind multiple $CBD_{N1}$-fusion proteins, suggests that both capacity and selectivity will be high in this affinity partition system. A summary of N1 binding thermodynamics is provided in Table 8 below. Binding of $CBD_{N1}$ to both HEC and barley β-glucan is strongly exothermic, indicating that binding will increase at lower temperatures and that temperature decrease can be used in the partition step and temperature elevation in elution steps.

Example 8

Phase-Equilibrium Analysis of Mixtures of HEC and Pluronic P105

Figure 19:
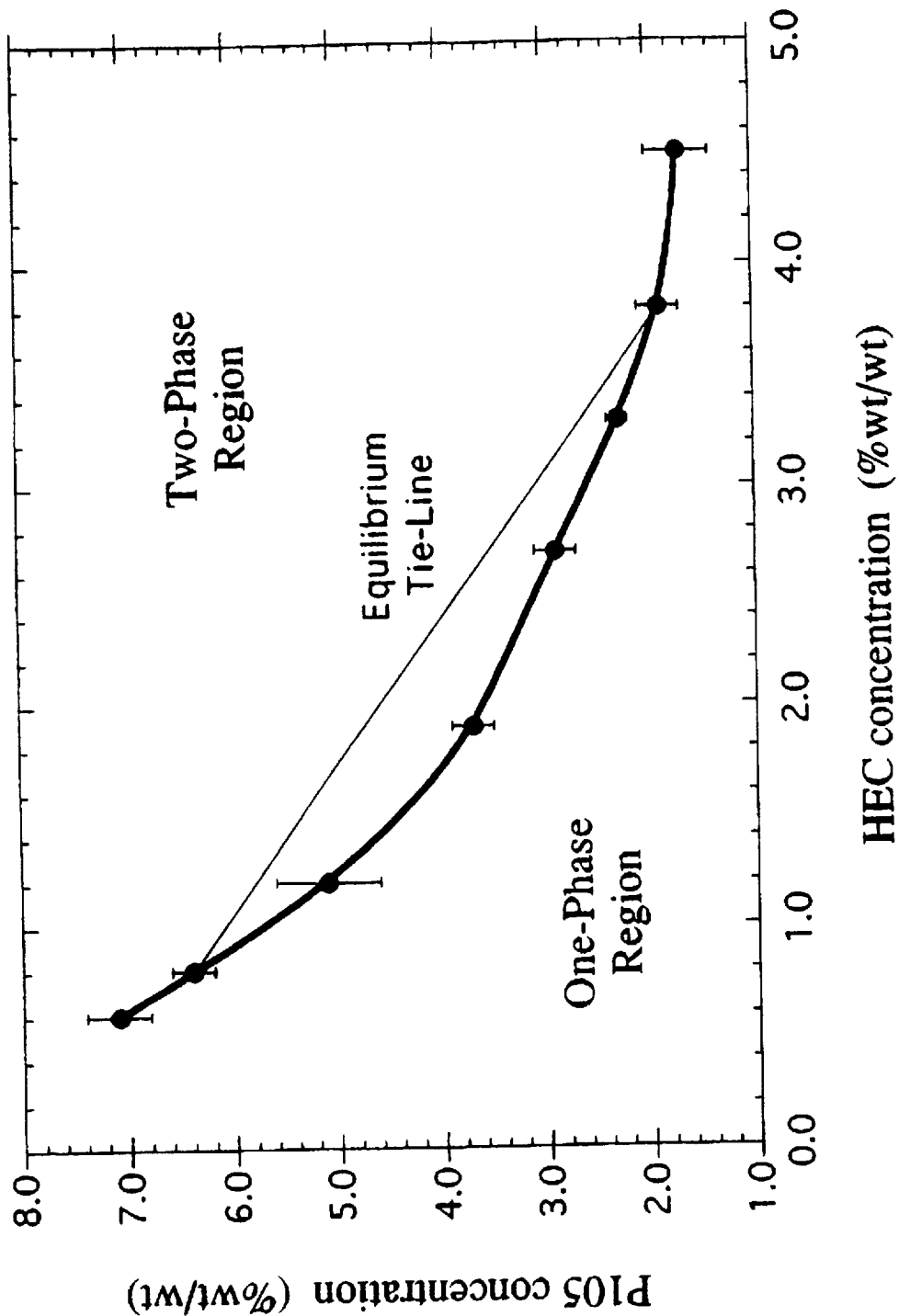
FIG. 19 shows preliminary phase-equilibria data for mixtures of hydroxyethyl cellulose and Pluronic P105 in 50 mM PBS at 35° C. and pH 7.

Phase-equilibria data were obtained using the procedure of Haynes et al. (Fluid Phase Equilibria, (1989) 53:463) for mixtures of HEC and Pluronic P105 (a poly(ethylene glycol) -poly (propylene glycol) copolymer) in 50-mM PBS at 35° C. and pH 7. As shown in FIG. 19, a stable two-phase partition system is formed at any total polymer concentrations above ca. 3% (wt/wt) Pluronic P105 and 2% HEC, giving a fairly large range of two-phase compositions and equilibrium tie-line lengths useful for affinity partitioning.

Example 9

Isothermal Titration Microcalorimetry Determination of Suitable Elution Conditions for $CBD_{N1}$ from an Oligosaccharide Polymer ITC is also used to determine suitable elution conditions by measuring equilibrium dissociation constants as a function of temperature, salt concentration and type, and concentration of cosolvents, such as ethylene glycol or urea, designed to disrupt the favorable hydrogen-bond structure of the $PBP_{N1}$-carbohydrate complex.

CenA and its isolated catalytic domain p30. Specific activity is determined from the amount of soluble reducing sugar produced from a fixed amount of substrate under fixed assay conditions. The reducing sugar is measured by a colorimet-

TABLE 7

Binding Specificity of $CBD_{N1}$ from Endoglucanase C of *Cellulomonas fimi*

| Ligand | Binding to N1(N2)[1] | Detection Method |
| --- | --- | --- |
| Glucose | − | NMR |
| Cellobiose | − | NMR |
| Cellotriose | +/− | NMR/calorimetry |
| Cellotetraose | ++ | NMR/calorimetry |
| Cellopentaose | +++ | NMR/calorimetry |
| Cellohexaose | +++ | NMR/calorimetry |
| Carboxymethylcellulose (CMC) | + | affinity electrophoresis/competition assay |
| Hydroxyethylcellulose (HEC) | +++ | affinity electrophoresis/competition assay |
| Phosphoric acid swollen cellulose (PASC) | +++ | binding isotherms |
| Avicel | + | binding isotherms |
| Bacterial microcrystalline cellulose (BMCC) | − | binding isotherms |
| Tunicin cellulose | +/− | binding isotherms |
| Barley β-glucan | +++ | calorimetry/affinity electrophoresis/competition assay |
| Oat β-glucan | +++ | calorimetry/affinity electrophoresis |
| Glucomannan | + | affinity electrophoresis |
| Pachyman | − | binding isotherms |
| Chitin | +/− | binding isotherms |
| Chitosan | +/− | affinity electrophoresis |
| Xylan | − | affinity electrophoresis/competition assay |
| Amylose | − | binding isotherms |
| Starch (soluble) | − | affinity electrophoresis |
| Sephadex | +/− | binding isotherms |
| Dextran T70 | − | affinity electrophoresis[1] |

[1] +++ represents strong binding; +/− represents weak binding; − represents no binding. ++ and + represent levels of binding between strong and weak binding.

TABLE 8

Summary of N1 Binding Thermodynamics at 35° C.

| | NMR | Isothermal Titration Microcalorimetry | | |
| --- | --- | --- | --- | --- |
| Ligand | $K_a$ ($M^{-1}$) | $K_a$ ($M^{-1}$) | $\Delta H°$ (kcal/mol) | $-T\Delta S°$ (kcal/mol) |
| Cellotriose | 180 ± 50 | n.m. | — | — |
| Cellotetrose | 4200 ± 700 | 4100 ± 500 | −6.4 ± 0.2 | 1.4 ± 0.1 |
| Cellopentose | 34000 ± 7500 | 17900 ± 3100 | −6.8 ± 0.2 | 0.86 ± 0.1 |
| Cellohexose | 51000 ± 18000 | 25200 ± 3900 | −6.9 ± 0.2 | 0.79 ± 0.1 |
| Barley β-Glucan | n.m. | 85500 ± 4400 | −7.3 ± 0.1 | 0.48 ± 0.1 |
| HEC | n.m. | 67000 ± 3900 | −7.2 ± 0.1 | 0.50 ± 0.1 |

Example 10

Figure 20:
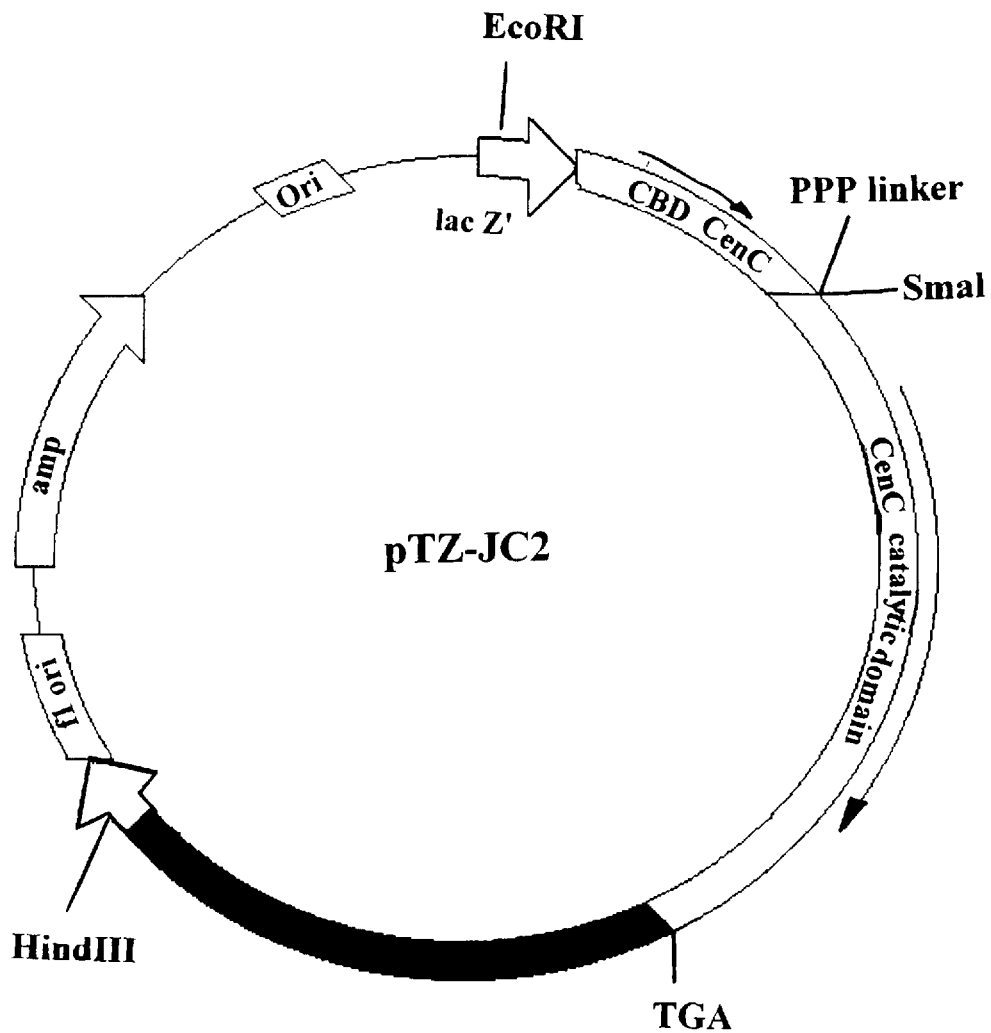
FIG. 20(A–C) shows the vectors used in the construction of pTZ-JC13 (FIG. 20C).
Figure 20:
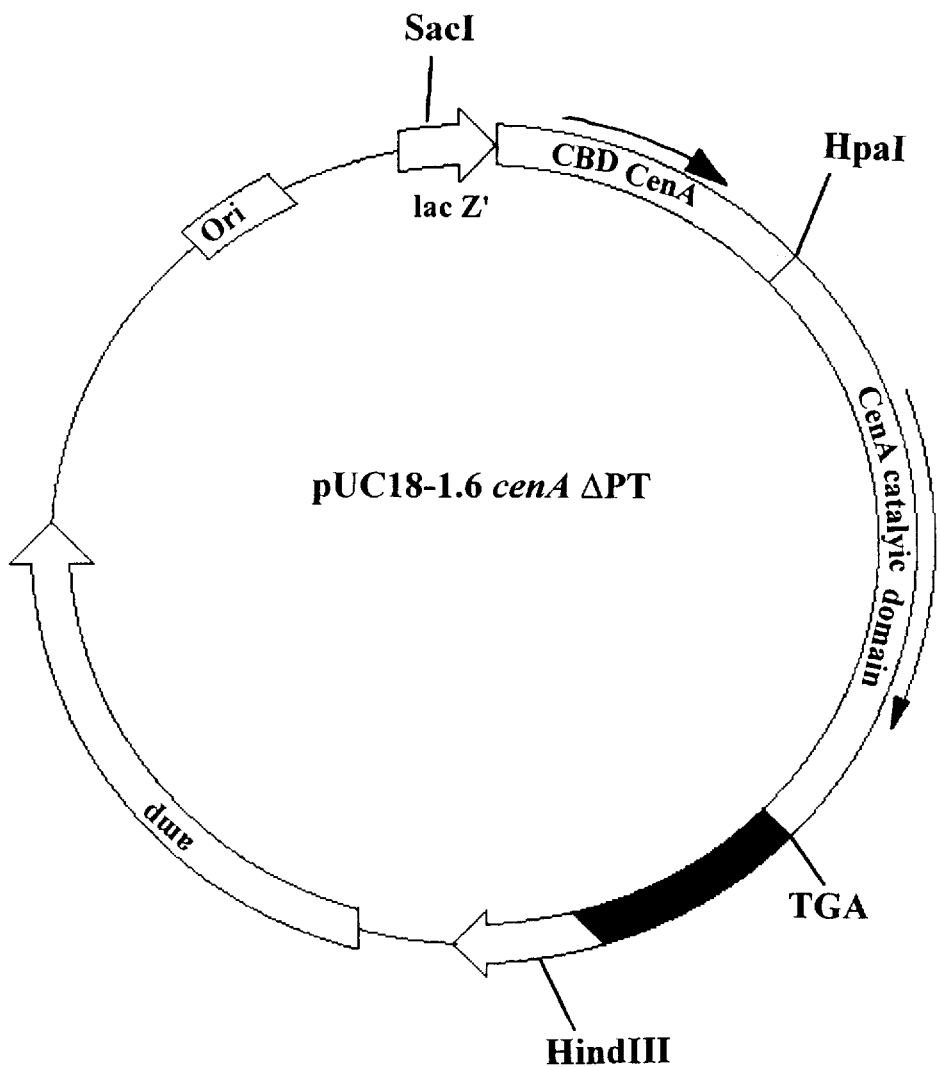
Figure 20:
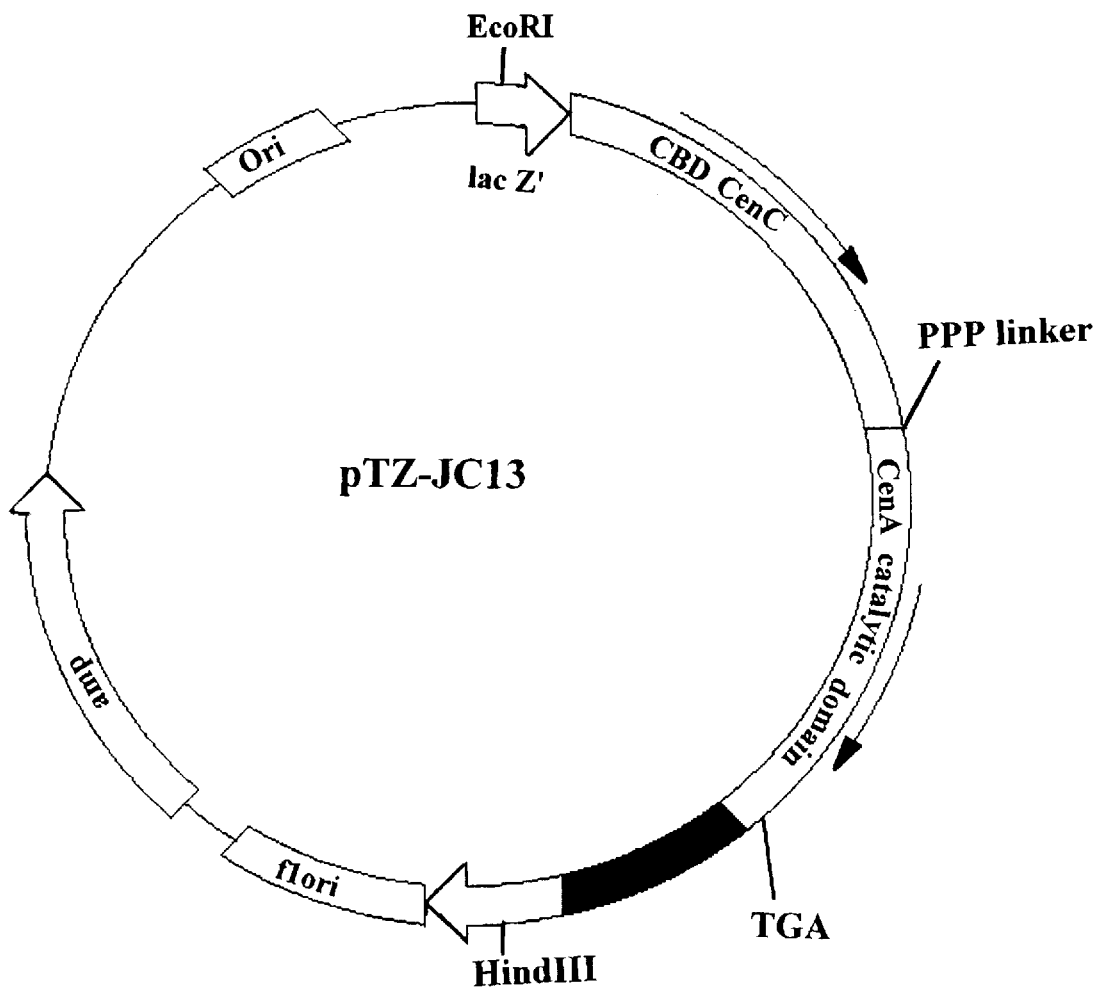

Construction of Expression Vector Containing Fusion of cenC CBD Gene Fragment and the *C. fimi* Endoglucanase A (cenA) Gene Fragment and Characterization of the Fusion Protein Construction of the Vector Plasmid pTZ-JC2 (see FIG. 20A) was digested to completion with SmaI and HindIII. The 3.9 kbp fragment was recovered. Plasmid pUC18–1.6 cenAΔPT (see FIG. 20B) was digested to completion with HpaI and HindIII and the 1.1 kbp fragment was recovered. The 3.9 and 1.1 kbp fragments were than ligated to give pTZ-JC13 (see FIG. 20C). This vector is used to transform *E. coli* JMI01.

Enzymatic characterization of the fusion protein

The expression product (fusion protein) encoded by pTZ-JC13 is characterized for its catalytic activity on Avicel, bacterial microcrystalline cellulose (BMCC) and phosphoric acid swollen cellulose (PASC) compared to the original ric assay and determined using a glucose standard. The concentration of polypeptides is determined by the binding of Coomassie Brilliant Blue G-250 (Gilkes et al. (1988) *J. Biol. Chem.* 263:10401–10407).

Figure 21:
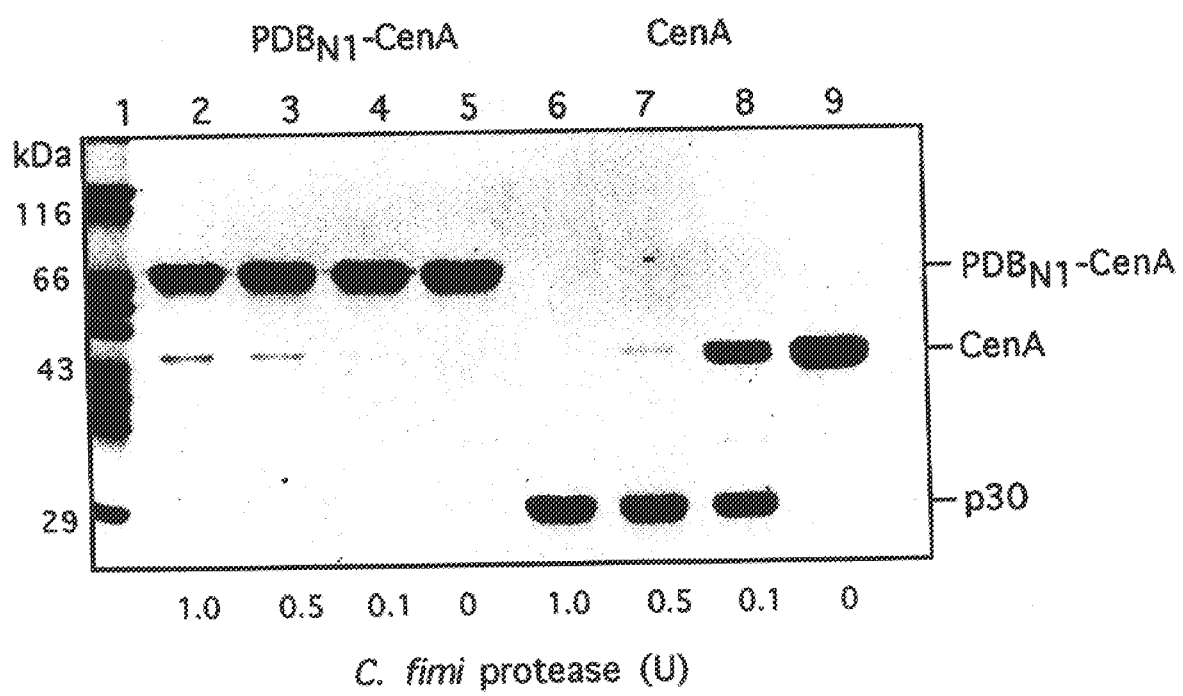
FIG. 21 shows the results of analysis of proteolysis products from CenA and the $PBD_{N1}$-CenA fusion protein using SDS-PAGE analysis. Eight µg of each polypeptide were incubated in 50 µl phosphate-buffer, pH 7.0 (50 mM) with 0 (lanes 5 and 9), 0.1 (lanes 4 and 8) 0.5 (lanes 3 and 7) or 1.0 units (lanes 2 and 6) of *C. fimi* protease for 3 h at 30° C. Reaction products were analyzed on gels containing 12.5% acrylamide. Molecular mass markers (lane 1) are as indicated. P30 corresponds to the catalytic domain of CenA after proteolytic removal of the cellulose-binding domain (Gilkes et al., *J. Biol. Chem* (1988) 263:10401–10407).

Evaluation of the susceptibility of the fusion protein to proteolytic degradation A major consideration in the use of fusion proteins is the stability of the polypeptides under a variety of conditions, including resistance against proteolytic degradation. The sensitivity of the fusion protein to proteolytic degradation in the absence of a linker sequence was evaluated with *C. fimi* protease. Cleavage of the fusion proteins with *C. fimi* protease was monitored by SDS-PAGE (see FIG. 21). The stability of the fusion protein was compared relative to the stability of CenA. The protease concentration and the proteolysis conditions were varied to optimize the results.

Figure 22:
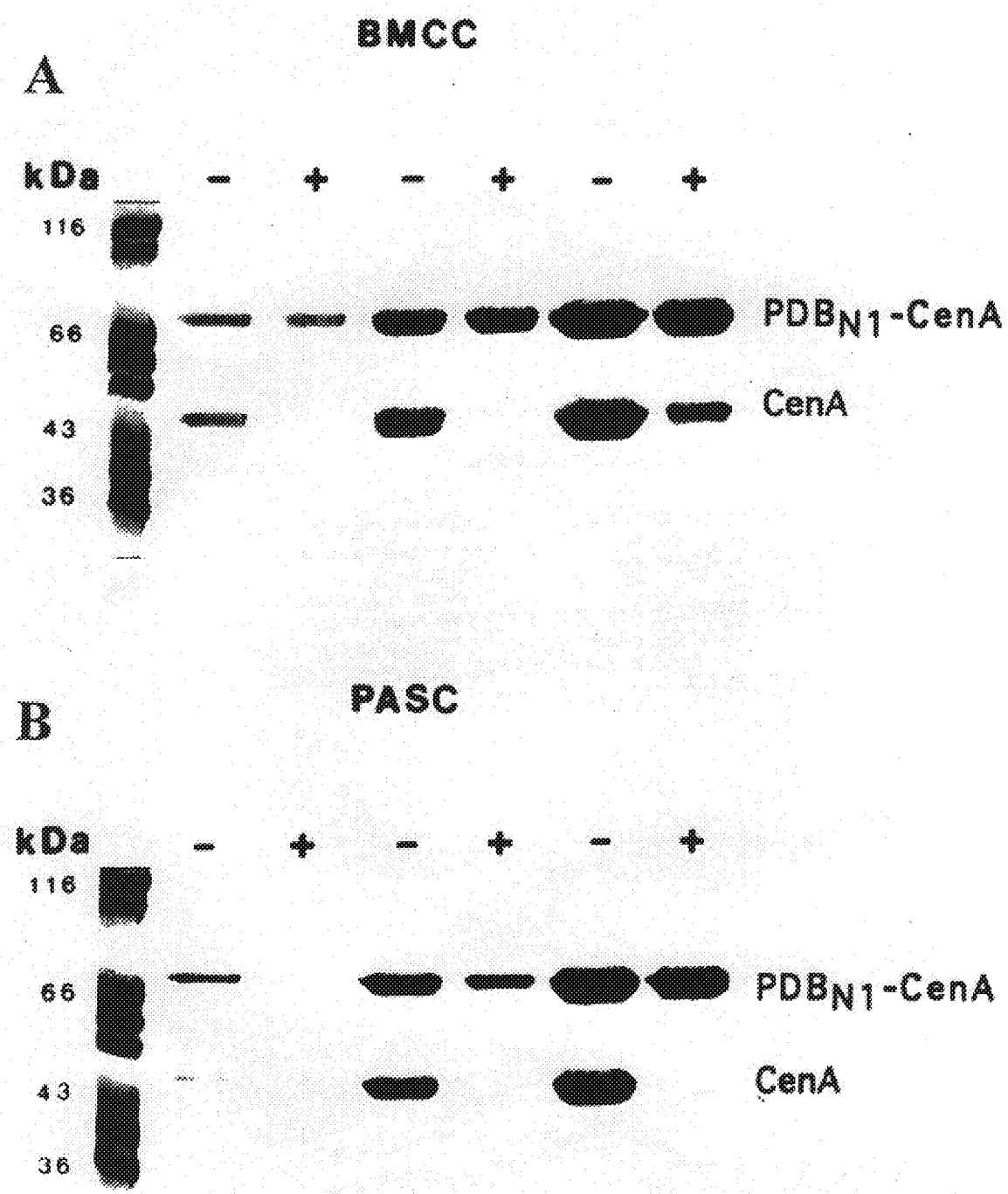
FIG. 22(A–B) shows the results of separation of CenA and $PBD_{N1}$-CenA by differential adsorption to cellulose followed by analysis of unadsorbed polypeptides using SDS-PAGE analysis.
Figure 23:
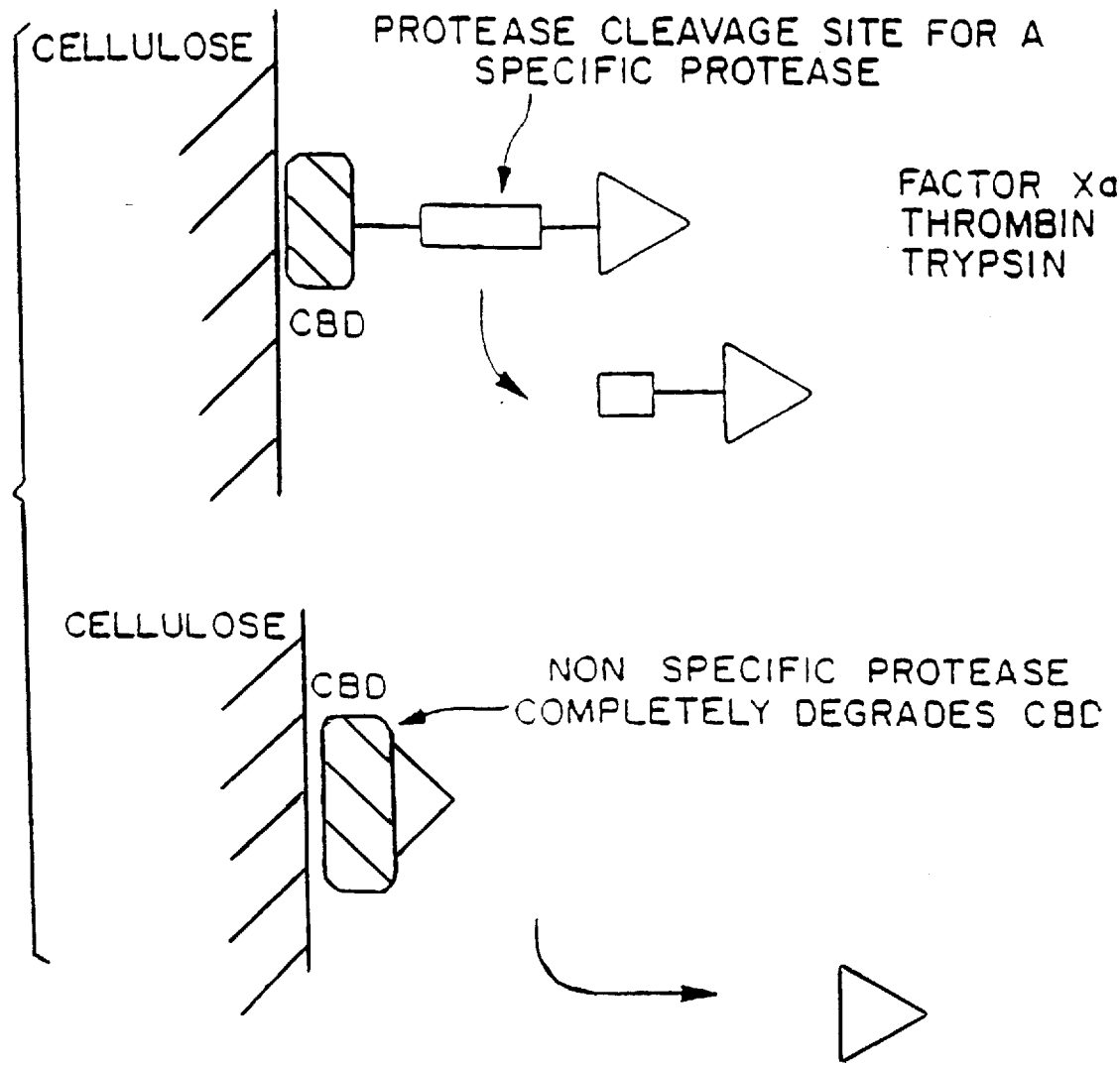
FIG. 23 shows two removable label compositions and means for enzymatically debinding the growth factor conjugate from a cellulose substrate: an arrow indicates a growth factor moiety, an open box indicates a protease cleavage site for a specific protease, and a cross-hatched box indicates a cellulose-binding domain.

Evaluation of the binding characteristics of the fusion protein; differential adsorption analysis To define the affinity of the PBD-fusion proteins for different cellulose allomorphs, binding to various cellulosic matrixes can simply be evaluated by SDS-PAGE analysis of bound fractions. This analysis has shown that PBDN1 binds to amorphous cellulose (PASC) but does not bind to crystalline cellulose (BMCC). The CBDCenA on the other hand has affinity for both cellulosic materials. These different binding characteristics offer the possibility for selective removal of one component in the presence of the other. In the first step BMCC is added to remove CenA. The PBD-fusion protein, left in solution after the first step, was then removed by adsorption to PASC (see FIG. 22). The concentration of the various protein components relative to the cellulose concentration was varied widely during the assay to evaluate the effect of non-saturating, saturating and over-saturating the cellulose.

This selective removal or binding of the different components has important implications for use in processing and purification of fusion proteins. The PBD can be removed proteolytically from the fusion protein while bound to the polysaccharide using a CBD-protease to liberate the compound of interest. The protease is then removed by virtue of its binding to cellulose (e.g., BMCC) leaving a pure compound.

Example 11

Production and Properties of a Bifunctional Fusion Protein that Mediates Separation of Vero Cells Using Oligosaccharide-polymer Based Affinity Phase Partitioning Bacterial Strains, Cell Lines, and Growth Conditions Chemicals were of analytical of HPLC grade. Recombinant DNA experiments were performed in *E. coli* JM 101 grown at 37° C. in LB medium supplemented with ampicillin (Boehringer Mannheim GmbH, Mannheim, Germany) at 100 µg/mL. High-level expression studies and large scale protein production were carried out in *E. coli* R1360 grown at 37° C. in TYP medium (16 g tryptone, 16 g yeast extract, 5 g NaCl, 2.5 g $K_2HPO_4$ per liter) supplemented with ampicillin (100 µg/mL). Bacterial medium components were from Difco Laboratories (Detroit, Mich.). Shaker speed for shaker flask cultures was set at 250 rpm. Cultures were induced with isopropyl-β-D-thiogalactoside (IPTG, Sigma Chemical Co., St. Louis, Mo.) at 0.15 mM. Vero (African green monkey, kidney-ATCC CCL 81) cells used in attachment studies were maintained in T flasks, in DMEM or DMEM/F12 medium (Gibco BRL, Gaithersburg, Md.) supplemented with 10% NCS (Gibco BRL), at 37° C., and 5% $CO_2$.

Recombinant DNA Techniques

All recombinant DNA work was carried out as described previously (Sambrook (1989) supra.). Double-stranded DNA was prepared by the alkaline-lysis method. DNA restriction and modification enzymes were used according to the manufacturer's recommendations. DNA fragments were separated by agarose gel electrophoresis. Large DNA fragments were isolated using GeneClean™ (Bio101, La Jolla, Calif.). Small DNA fragments (less than 100 bp) were isolated by the liquid nitrogen method. Frozen competent *E. coli* cells were used for all transformations. Oligodeoxynucleotides were synthesized with an ABI 380A DNA synthesizer (Applied Biosystems, Foster City, Calif.) and purified by C18 cartridge Chromatography. Annealing of oligodeoxynucleotides was performed at 74° C. for 10 min in sequencing buffer (40 mM Tris-HCl or pH 7.5, 20 mM $MgCl_2$, 50 mM NaCl), followed by slow cooling at 4° C. DNA was sequenced by the dideoxy chain terminating method using modified T7 DNA polymerase (Sanger et al., *Proc. Nat'l Acad. Sci. USA* (1977) 74:5463–5467).

Polypeptide Analysis

Polypeptides were resolved by sodium dodecyl sulfate polyacrylamide gel electrophoresis (SDS-PAGE). The gels were stained with Coomassie Brilliant Blue R250 (BioRad, Richmond, Calif.); bands were quantified using a scanning densitometer (Computing Densitometer, Molecular Dynamics, Sunnyvale, Calif.) equipped with ImageQuant™ software. Pure $CBD_{N1}$/RGD standards were included with each set of gels. Concentrations of pure preparations of $CBD_{N1}$/RGD were determined by absorbance at 280 nm using the extinction coefficient determined for pure CBD/RGD (Scopes (1974) *Anal. Biochem.* 59:277–282). Western blotting was performed using rabbit anti-CenA serum as primary antibody and goat anti-rabbit serum conjugated to horseradish peroxidase (Gibco BRL) as secondary antibody.

Oligosaccharide Binding Assay

This was performed as described in Example 7.

Large-Scale Production and Purification of $CBD_{N1}$/RGD $CBD_{N1}$ is produced as described in Wierzba et al., *Biotechnol. and Bioeng.* (1995) 47:147–154, except that the coding sequence for $CBD_{N1}$ replaces the coding sequence for the cellulase binding domain (CBD) of *Cellulomonas fimi* endoglucanase A (CenA) in the R1360/pTZ18U-CBD/RGD construct. *E. coli* containing the construct are grown at 37° C. in a 12-L fermentor (Chemap AG, Volketswil, Switzerland) in TYP medium supplemented with ampicillin (100 µg/mL), and IPTG (0.15 mM). Cells are separated from the culture medium by centrifugation at 31,000 g (Sharples-Stokes Division, Pennwalt Corp., Warminster, Pa.). $CBD_{N1}$/RGD in the culture medium and in the cellular fraction is purified separately using affinity-phase partitioning using mixtures of HEC and Pluronic P105 as described in Example 8. Culture medium is filtered through a GF/C glass fiber filter (Whatman International, Maidstone, UK) to remove cell debris. The culture medium is added to the phase separation system. According to the methodology for other aqueous two-phase partition systems (e.g., Joshi et al., *Bioseparations*, (1990) 11:311) with the important difference that the separation is greatly enhanced by binding of the $CBD_{N1}$ fusion to the HEC. Affinity extraction of the $CBD_{N1}$-fusion protein from a culture supernatant or a cell extract can occur in either a commercial Graesser-type contactor (employed in most large-scale partitioning systems) or a mixer-settler battery (Haynes, Ph.D. Thesis, University of California at Berkeley (1991)). The carbohydrate-rich extract phase containing the $CBD_{N1}$-fusion protein is pumped to a second mixer-settler battery for back extraction of the product, while the poly(oxy-ether)-rich phase is stripped with an incompatible salt and then recycled to the affinity contactor (Haynes et al., *AIChE J.*, (1991) 37:1401). Addition of sufficient salt, usually a sulfate or citrate salt, to a carbohydrate-rich extract phase containing a bound target protein results in phase separation (see Walter et al., *Partitioning in Aqueous Two-Phase Systems*, Academic Press (1985)). The 2M and higher salt concentrations required for phase separation often leads to dissociation of the ligand-protein complex and thus, a simple means of product recovery. The strongly exothermic binding between $CBD_{N1}$ and HEC indicates that dissociation can also be achieved through either a modest increase in temperature or addition of a hydrogen-bond disrupting cosolvent. Excess salt is removed by diafiltration or other desalting methodology. The suspension is stirred gently at 4° C. overnight. The eluate is concentrated and exchanged with $dH_2O$ (to less than 50 nM GdmC 1) by ultrafiltration using a 1-kD cutoff membrane (Amnicon Division, W.R. Grace & Co., Beverly, Mass.). The $CBD_{N1}$/RGD solution (5 to 12 mg/mL) is filter sterilized (0.2 µm) and stored at −20° C.

*E. coli* cells are washed with 50 mM potassium phosphate buffer (pH 7.0), resuspended in 150 mL of the same buffer supplemented with 3 mM EDTA, and ruptured in a 50-mL French pressure cell (SLM Instruments, Urbana, Ill.). Phenylmethylsulfonylfluoride (1 mM) and pepstatin A (1 µM) are added to the cell extract to minimize proteolysis. Cellular debris is removed by centrifugation at 17,400 g for 30 min at 4° C. Streptomycin sulfate (Sigma) is added to the supernatant (1.5% w/v). After incubation overnight at 4° C., the precipitate is collected by centrifugation at 17,400 g for 30 min at 4° C. The supernatant is added to the affinity partition system and the $CBD_{N1}$/RGD is purified as described above for the culture broth.

Cell Separation Assay

Cells are detached from culture dishes with trypsin and EDTA, washed once with DMEM medium containing 0.01% soybean trypsin inhibitor (Sigma), and twice with DMEM medium without the inhibitor. To a total of $4 \times 10^6$ washed cells is added $CBD_{N1}$ in serum-free culture medium. After incubation for 1 h at 37° C., the cells with $CBD_{N1}$/RGD bound are added to the affinity phase partitioning system. After separation of the HEC phase, trypsin is added to release the cells from the HEC and the cells are collected by centrifugation. Viability of the cells is assessed using trypan blue exclusion.

The above results demonstrate the construction and purification of a growth factor conjugate that consists of a steel factor extracellular domain and a cellulase polysaccharide binding peptide (SLF-CBD). The SLF-CBD, when bound to microcrystalline cellulose, stimulates proliferation of steel-factor responsive cells to a greater extent than non-immobilized steel factor; the immobilized SLF-CBD has both a higher specific activity and a greater maximum proliferative response compared to non-immobilized steel factor. SLF-CBD bound to a cellulose surface can be re-used several times without loss of growth-stimulating activity.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A composition comprising:

a first member of a specific binding pair; and a conjugate comprising a second member of said specific binding pair and an amino acid sequence comprising a substrate binding region derived from a polysaccharidase, wherein said amino acid sequence is essentially lacking in hydrolytic activity of said polysaccharidase, wherein said first member of said specific binding pair is a growth factor receptor, and wherein said second member of said specific binding pair is a polypeptide which modulates cell proliferation.

2. The composition according to claim 1, wherein said polysaccharidase is a β-1,4-glucanase.

3. The composition according to claim 2, wherein said β-1,4-glucanase is a cellulase.

4. The composition according to claim 3, wherein said cellulase is obtainable from *Cellulomonas fimi*.

5. The composition according to claim 1, wherein said amino acid sequence is bound to a substrate for said polysaccharidase.

6. The composition according to claim 5, wherein said substrate is insoluble.

7. The composition according to claim 1, wherein said growth factor receptor is a receptor for a cytokine or a receptor for a lymphokine.

8. The composition according to claim 1, wherein said growth factor receptor is selected from the group consisting of a receptor for a steel factor, an interleukin-2, an interleukin-3, an interleukin-6, a mast cell growth factor, a granulocyte colony stimulating factor, a granulocyte-macrophage colony stimulating factor, a fibroblast growth factor, a platelet derived growth factor, and an epidermal growth factor.

9. A composition comprising:
   a first member of a specific binding pair; and a conjugate comprising a second member of said specific binding pair and an amino acid sequence comprising a substrate binding region derived from a polysaccharidase, wherein said amino acid sequence is essentially lacking in hydrolytic activity of said polysaccharidase, and wherein said first member is selected from the group consisting of a MHC polypeptide, a T-cell receptor, a c-kit gene product, and an immunoglobulin.

10. The composition according to claim 1, wherein said growth factor receptor is derived from cells selected from the group consisting of stem cells, killer T-cells, megakaryocytes and fibroblasts.

11. The composition according to claim 10, wherein said first member is a growth factor receptor on the surface of a cell grown in vitro.

12. A conjugate comprising:
    an amino acid sequence comprising a substrate binding region derived from a polysaccharidase, bound to a first and a second growth factor wherein said amino acid sequence is essentially lacking in hydrolytic activity of said polysaccharidase, and wherein said first and second growth factors are different.

13. The conjugate according to claim 12 wherein said first growth factor is a steel factor and said second growth factor is selected from the group consisting of an interleukin-2, an interleukin-3, an interleukin-6, a mast cell growth factor, a granulocyte colony stimulating factor, a granulocyte-macrophage colony stimulating factor, a fibroblast growth factor, a platelet derived growth factor, and an epidermal growth factor.

14. A method of in vitro expansion of growth factor dependent cells, said method comprising:
    growing said cells in contact with a conjugate comprising a said growth factor and an amino acid sequence comprising a substrate binding region derived from a polysaccharidase immobilized on a substrate of said polysaccharidase, wherein said amino acid sequence is essentially lacking in hydrolytic activity of said polysaccharidase, and wherein said cells are growth-responsive to said growth factor.

15. The method according to claim 14, wherein said cells are hematopoietic.

16. The method according to claim 15, wherein said cells are pluripotent.

17. The method according to claim 15, wherein said cells are stem cells.

18. The method according to claim 14, wherein said cells are megakaryocytes.

19. The method according to claim 15, wherein said cells are from bone marrow or blood.

20. The method according to claim 14, wherein said amino acid sequence is bound to a polysaccharide matrix contained within an extracorporeal device.

21. The method of in vitro expansion of steel factor dependent cells, said method comprising:
    growing said cells in contact with a conjugate comprising said steel factor and an amino acid sequence comprising a substrate binding region derived from a polysaccharidase immobilized on a substrate of said polysaccharidase, wherein said amino acid sequence is essentially lacking in hydrolytic activity of said polysaccharidase.

22. A method of obtaining a population of cells enriched in cells having a growth factor receptor, said method comprising:
    contacting a plurality of cells having a cell surface receptor for said growth factor with a conjugate comprising said growth factor and an amino acid sequence comprising a substrate binding region derived from a polysaccharidase bound to a substrate for said polysaccharidase; and
    removing any cells lacking said cell surface receptor, whereby a population of cells enriched in cells having a growth factor receptor is obtained.

23. The method according to claim 22, wherein said substrate is in the form of a microcarrier.

24. The method according to claim 14, wherein said amino acid sequence is bound to a polysaccharide matrix associated with a solid support.

25. The method according to claim 14 or 22, wherein said substrate is cellulose acetate.

26. The method according to claim 14 or 22, wherein said substrate is in the form of micro-crystalline cellulose.

27. The method according to claim 14 or 22, wherein said substrate is a membrane.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 109 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:1:

```
Ala  Pro  Gly  Cys  Arg  Val  Asp  Tyr  Ala  Val  Thr  Asn  Gln  Trp  Pro  Gly
1                   5                        10                       15

Gly  Phe  Gly  Ala  Asn  Val  Thr  Ile  Thr  Asn  Leu  Gly  Asp  Pro  Val  Ser
               20                       25                       30

Ser  Trp  Lys  Leu  Asp  Trp  Thr  Tyr  Thr  Ala  Gly  Gln  Arg  Ile  Gln  Gln
          35                       40                       45

Leu  Trp  Asn  Gly  Thr  Ala  Ser  Thr  Asn  Gly  Gly  Gln  Val  Ser  Val  Thr
     50                       55                       60

Ser  Leu  Pro  Trp  Asn  Gly  Ser  Ile  Pro  Thr  Gly  Gly  Thr  Ala  Ser  Phe
65                       70                       75                       80

Gly  Phe  Asn  Gly  Ser  Trp  Ala  Gly  Ser  Asn  Pro  Thr  Pro  Ala  Ser  Phe
               85                       90                       95

Ser  Leu  Asn  Gly  Thr  Thr  Cys  Thr  Gly  Thr  Val  Pro  Thr
               100                      105
```

( 2 ) INFORMATION FOR SEQ ID NO:2:

( i ) SEQUENCE CHARACTERISTICS:
        ( A ) LENGTH: 108 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:2:

```
Ser  Gly  Pro  Ala  Gly  Cys  Gln  Val  Leu  Trp  Gly  Val  Asn  Gln  Trp  Asn
1                   5                        10                       15

Thr  Gly  Phe  Thr  Ala  Asn  Val  Thr  Val  Lys  Asn  Thr  Ser  Ser  Ala  Pro
```

|  |  |  | 20 |  |  |  | 25 |  |  |  | 30 |  |  |  |
|---|---|---|---|---|---|---|---|---|---|---|---|---|---|---|
| Val | Asp | Gly | Trp | Thr | Leu | Thr | Phe | Ser | Phe | Pro | Ser | Gly | Gln | Val |
|  |  | 35 |  |  |  |  | 40 |  |  |  |  | 45 |  |  |
| Thr | Gln | Ala | Trp | Ser | Ser | Thr | Val | Thr | Gln | Ser | Gly | Ser | Ala | Val | Thr |
|  | 50 |  |  |  |  | 55 |  |  |  |  | 60 |  |  |  |
| Val | Arg | Asn | Ala | Pro | Trp | Asn | Gly | Ser | Ile | Pro | Ala | Gly | Gly | Thr | Ala |
| 65 |  |  |  |  | 70 |  |  |  |  | 75 |  |  |  |  | 80 |
| Gln | Phe | Gly | Phe | Asn | Gly | Ser | His | Thr | Gly | Thr | Asn | Ala | Ala | Pro | Thr |
|  |  |  |  | 85 |  |  |  |  | 90 |  |  |  |  | 95 |  |
| Ala | Phe | Ser | Leu | Asn | Gly | Thr | Pro | Cys | Thr | Val | Gly |
|  |  |  |  | 100 |  |  |  | 105 |  |  |  |

( 2 ) INFORMATION FOR SEQ ID NO:3:

( i ) SEQUENCE CHARACTERISTICS:
        ( A ) LENGTH: 104 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:3:

| Gln | Pro | Pro | Ala | Gly | Arg | Ala | Cys | Glu | Ala | Thr | Tyr | Ala | Leu | Val | Asn |
| 1 |  |  |  | 5 |  |  |  |  | 10 |  |  |  |  | 15 |  |
| Gln | Trp | Pro | Gly | Gly | Phe | Gln | Ala | Glu | Val | Thr | Val | Lys | Asn | Thr | Gly |
|  |  |  | 20 |  |  |  |  | 25 |  |  |  |  | 30 |  |  |
| Ser | Ser | Pro | Ile | Asn | Gly | Trp | Thr | Val | Gln | Trp | Thr | Leu | Pro | Ser | Gly |
|  |  | 35 |  |  |  |  | 40 |  |  |  |  | 45 |  |  |  |
| Gln | Ser | Ile | Thr | Gln | Leu | Trp | Asn | Gly | Asp | Leu | Ser | Thr | Ser | Gly | Ser |
|  | 50 |  |  |  |  | 55 |  |  |  |  | 60 |  |  |  |  |
| Asn | Val | Thr | Val | Arg | Asn | Val | Ser | Trp | Asn | Gly | Asn | Val | Pro | Ala | Gly |
| 65 |  |  |  |  | 70 |  |  |  |  | 75 |  |  |  |  | 80 |
| Gly | Ser | Thr | Ser | Phe | Gly | Phe | Leu | Gly | Ser | Gly | Thr | Gly | Gln | Leu | Ser |
|  |  |  |  | 85 |  |  |  |  | 90 |  |  |  |  | 95 |  |
| Ser | Ser | Ile | Thr | Cys | Ser | Ala | Ser |
|  |  |  | 100 |  |  |  |  |

( 2 ) INFORMATION FOR SEQ ID NO:4:

( i ) SEQUENCE CHARACTERISTICS:
        ( A ) LENGTH: 106 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:4:

| Thr | Gly | Ser | Cys | Lys | Val | Glu | Tyr | Asn | Ala | Ser | Ser | Trp | Asn | Thr | Gly |
| 1 |  |  |  | 5 |  |  |  |  | 10 |  |  |  |  | 15 |  |
| Phe | Thr | Ala | Ser | Val | Arg | Val | Thr | Asn | Thr | Gly | Thr | Thr | Ala | Leu | Asn |
|  |  |  | 20 |  |  |  |  | 25 |  |  |  |  | 30 |  |  |
| Gly | Trp | Thr | Leu | Thr | Phe | Pro | Phe | Ala | Asn | Gly | Gln | Thr | Val | Gln | Gln |
|  |  | 35 |  |  |  |  | 40 |  |  |  |  | 45 |  |  |  |
| Gly | Trp | Ser | Ala | Asp | Trp | Ser | Gln | Ser | Gly | Thr | Thr | Val | Thr | Ala | Lys |
|  | 50 |  |  |  |  | 55 |  |  |  |  | 60 |  |  |  |  |
| Asn | Ala | Ala | Trp | Asn | Gly | Ser | Leu | Ala | Ala | Gly | Gln | Thr | Val | Asp | Ile |
| 65 |  |  |  |  | 70 |  |  |  |  | 75 |  |  |  |  | 80 |
| Gly | Phe | Asn | Gly | Ala | His | Asn | Gly | Thr | Asn | Asn | Lys | Pro | Ala | Ser | Phe |

85                            90                            95
         Thr  Leu  Asn  Gly  Ala  Thr  Cys  Thr  Val  Gly
                               100                           105

(2) INFORMATION FOR SEQ ID NO:5:

(i) SEQUENCE CHARACTERISTICS:
        (A) LENGTH: 103 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:5:

Ala  Ala  Ser  Gly  Gly  Asn  Cys  Gln  Tyr  Val  Val  Thr  Asn  Gln  Trp  Asn
         1                   5                             10                          15

Asn  Gln  Phe  Thr  Ala  Val  Ile  Arg  Val  Arg  Asn  Asn  Gly  Ser  Ser  Ala
                             20                            25                          30

Ile  Asn  Arg  Trp  Ser  Val  Asn  Trp  Ser  Tyr  Ser  Asp  Gly  Ser  Arg  Ile
                        35                            40                       45

Thr  Asn  Ser  Trp  Asn  Ala  Asn  Val  Thr  Gly  Asn  Asn  Pro  Tyr  Ala  Ala
                   50                       55                       60

Ser  Ala  Leu  Gln  Trp  Asn  Ala  Asn  Ile  Gln  Pro  Gly  Gln  Thr  Ala  Glu
         65                       70                            75                       80

Phe  Gly  Phe  Gln  Gly  Thr  Lys  Gly  Ala  Gly  Ser  Arg  Gln  Val  Pro  Ala
                             85                            90                           95

Val  Thr  Gly  Ser  Val  Cys  Gln
                         100

(2) INFORMATION FOR SEQ ID NO:6:

(i) SEQUENCE CHARACTERISTICS:
        (A) LENGTH: 104 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:6:

Gln  Thr  Ala  Thr  Cys  Ser  Tyr  Asn  Ile  Thr  Asn  Glu  Trp  Asn  Thr  Gly
         1                   5                             10                          15

Tyr  Thr  Gly  Asp  Ile  Thr  Ile  Thr  Asn  Arg  Gly  Ser  Ser  Ala  Ile  Asn
                             20                            25                          30

Gly  Trp  Ser  Val  Asn  Trp  Gln  Tyr  Ala  Thr  Asn  Arg  Leu  Ser  Ser  Ser
                        35                            40                       45

Trp  Asn  Ala  Asn  Val  Ser  Gly  Ser  Asn  Pro  Tyr  Ser  Ala  Ser  Asn  Leu
                   50                       55                       60

Ser  Trp  Asn  Gly  Asn  Ile  Gln  Pro  Gly  Gln  Ser  Val  Ser  Phe  Gly  Phe
         65                       70                            75                       80

Gln  Val  Asn  Lys  Asn  Gly  Gly  Ser  Ala  Glu  Arg  Pro  Ser  Val  Gly  Gly
                             85                            90                           95

Ser  Ile  Cys  Ser  Gly  Ser  Val  Ala
                         100

(2) INFORMATION FOR SEQ ID NO:7:

(i) SEQUENCE CHARACTERISTICS:
        (A) LENGTH: 97 amino acids
        (B) TYPE: amino acid
        (C) STRANDEDNESS: Not Relevant ( D ) TOPOLOGY: Not Relevant ( i i ) MOLECULE TYPE: peptide ( x i ) SEQUENCE DESCRIPTION: SEQ ID NO:7:

| Val | Ser | Gly | Ala | Leu | Lys | Ala | Glu | Tyr | Thr | Ile | Asn | Asn | Trp | Gly | Ser |
|---|---|---|---|---|---|---|---|---|---|---|---|---|---|---|---|
| 1 | | | | 5 | | | | | 10 | | | | | | 15 |

| Gly | Tyr | Gln | Val | Leu | Ile | Lys | Val | Lys | Asn | Asp | Ser | Ala | Ser | Arg | Val |
|---|---|---|---|---|---|---|---|---|---|---|---|---|---|---|---|
| | | | 20 | | | | | 25 | | | | | 30 | | |

| Asp | Gly | Trp | Thr | Leu | Lys | Ile | Ser | Lys | Ser | Glu | Val | Lys | Ile | Asp | Ser |
|---|---|---|---|---|---|---|---|---|---|---|---|---|---|---|---|
| | | 35 | | | | | 40 | | | | | 45 | | | |

| Ser | Trp | Cys | Val | Asn | Ile | Ala | Glu | Glu | Gly | Gly | Tyr | Tyr | Val | Ile | Thr |
|---|---|---|---|---|---|---|---|---|---|---|---|---|---|---|---|
| | 50 | | | | | 55 | | | | | | 60 | | | |

| Pro | Met | Ser | Trp | Asn | Ser | Ser | Leu | Glu | Pro | Ser | Ala | Ser | Val | Asp | Phe |
|---|---|---|---|---|---|---|---|---|---|---|---|---|---|---|---|
| 65 | | | | | 70 | | | | | 75 | | | | | 80 |

| Gly | Ile | Gln | Gly | Ser | Gly | Ser | Ile | Gly | Thr | Ser | Val | Asn | Ile | Ser | Val |
|---|---|---|---|---|---|---|---|---|---|---|---|---|---|---|---|
| | | | | 85 | | | | | 90 | | | | | 95 | |

Gln ( 2 ) INFORMATION FOR SEQ ID NO:8:

( i ) SEQUENCE CHARACTERISTICS:
        ( A ) LENGTH: 103 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

```
ATCTAGAAAT AATTTTGTTT AACTTTAAGA AGGAGATATA TCCATGGAAT TCGAGCTCGG        60
TACCCGGGGA TCCTCTAGAG TCGACCTGCA GGCATGCAAG CTT                        103
```

( 2 ) INFORMATION FOR SEQ ID NO:9:

( i ) SEQUENCE CHARACTERISTICS:
        ( A ) LENGTH: 20 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:9:

| Met | Glu | Phe | Glu | Leu | Gly | Thr | Arg | Gly | Ser | Ser | Arg | Val | Asp | Leu | Gln |
|---|---|---|---|---|---|---|---|---|---|---|---|---|---|---|---|
| 1 | | | | 5 | | | | | 10 | | | | | 15 | |

| Ala | Cys | Lys | Leu |
|---|---|---|---|
| | | | 20 |

( 2 ) INFORMATION FOR SEQ ID NO:10:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
GAAGGAGCTC CTTGATGTCC ACCCGC                                           26
```

( 2 ) INFORMATION FOR SEQ ID NO:11:

(i) SEQUENCE CHARACTERISTICS:
  (A) LENGTH: 72 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:11:

ATCGAGGGCA GGCCTGAATT CCAGCTCGGT ACCCGGGGAT CCTCTAGAGT CGACCTGCAG    60

GCATGCAAGC TT    72

(2) INFORMATION FOR SEQ ID NO:12:

(i) SEQUENCE CHARACTERISTICS:
    (A) LENGTH: 24 amino acids
    (B) TYPE: amino acid
    (C) STRANDEDNESS: Not Relevant
    (D) TOPOLOGY: linear (ii) MOLECULE TYPE: peptide (xi) SEQUENCE DESCRIPTION: SEQ ID NO:12:

Ile Glu Gly Arg Pro Glu Phe Gln Leu Gly Thr Arg Gly Ser Ser Arg
1               5                   10                  15

Val Asp Leu Gln Ala Cys Lys Leu
                20

(2) INFORMATION FOR SEQ ID NO:13:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "oligonucleotide"

(xi) SEQUENCE DESCRIPTION: SEQ ID NO:13:

TTACCTCATA TGGCTAGCCC GATCGGGGAG GGAACG    36

(2) INFORMATION FOR SEQ ID NO:14:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "oligonucleotide"

(xi) SEQUENCE DESCRIPTION: SEQ ID NO:14:

AGAATGAATT CAAGCTTAGA GCTCGACCTC GGAGTC    36